(12) United States Patent
Savelieva et al.

(10) Patent No.: US 11,352,639 B2
(45) Date of Patent: Jun. 7, 2022

(54) GENE THERAPY BASED ON VECTOR VTVAF17

(71) Applicants: OBSCHESTVO S OGRANICHENNOI OTVETSTVENNOSTJU "ALLEL TSENTR INNOVATSIONNYKH BIOTEKHNOLOGY", Moscow (RU); OBSCHESTVO S OGRANICHENNOI OTVETSTVENNOSTJU "PRORYVNYE INNOVATSIONNYE TEKHNOLOGII", Moscow (RU); CELL AND GENE THERAPY LTD, London (GB)

(72) Inventors: Natalia Savelieva, Wienna (AT); Vasily Nikolaevich Lazarev, Moscow (RU); Galina Vasilievna Shmarina, Moscow (RU)

(73) Assignees: OBSCHESTVO S OGRANICHENNOI OTVETSTVENNOSTJU "ALLEL TSENTR INNOVATSIONNYKH BIOTEKHNOLOGY", Moscow (RU); OBSCHESTVO S OGRANICHENNOI OTVETSTVENNOSTJU "PRORYVNYE INNOVATSIONNYE TEKHNOLOGII", Moscow (RU); CELL AND GENE THERAPY LTD, London (GB)

( * ) Notice: Subject to any disclaimer, the term of this patent is extended or adjusted under 35 U.S.C. 154(b) by 0 days.

(21) Appl. No.: 17/272,730

(22) PCT Filed: Aug. 14, 2019

(86) PCT No.: PCT/RU2019/000576
§ 371 (c)(1),
(2) Date: Mar. 2, 2021

(87) PCT Pub. No.: WO2020/050744
PCT Pub. Date: Mar. 12, 2020

(65) Prior Publication Data
US 2021/0310021 A1    Oct. 7, 2021

(30) Foreign Application Priority Data

Sep. 4, 2018   (RU) ............................ 2018131708

(51) Int. Cl.
*C12N 15/85* (2006.01)
*C12N 15/70* (2006.01)
*A61K 48/00* (2006.01)

(52) U.S. Cl.
CPC ............ *C12N 15/85* (2013.01); *C12N 15/70* (2013.01); *A61K 48/00* (2013.01)

(58) Field of Classification Search
CPC ........ C12N 15/85; C12N 15/70; A61K 48/00; A61P 19/08
See application file for complete search history.

(56) References Cited

U.S. PATENT DOCUMENTS 9,550,998 B2   1/2017  Williams
9,644,211 B2   5/2017  Mayrhofer

FOREIGN PATENT DOCUMENTS

| RU | 2011110736 A | 9/2012 | |
|---|---|---|---|
| RU | 2548809 C2 | 4/2015 | |
| RU | 2015140941 A | 3/2017 | |
| WO | WO-2019039962 A1 * | 2/2019 | ............ C12N 15/70 |

OTHER PUBLICATIONS

Kawai et al. Non-surgical model for alveolar bone regeneration by bone morphogenetic protein-2/7 gene therapy. Journal of Periodontology, vol. 89, pp. 85-92, 2018. (Year: 2018).*
Ishihara et al. Autologous implantation of BMP2-expressing dermal fibroblasts to improve bone mineral density and architecture in rabbit long bones. Journal of Orthopaedic Research, vol. 33, No. 10, pp. 1455-1465, Aug. 2015. (Year: 2015).*
Evans et al. Gene delivery to bone. Advanced Drug Delivery Reviews, vol. 64, pp. 1331-1340, Mar. 2012. (Year: 2012).*
Niyibizi et al. (Gene therapy approaches for osteogenesis imperfecta, vol. 11, pp. 408-416, 2004. (Year: 2004).*
Marom et al. Pharmacological and biological therapeutic strategies for osteogenesis imperfecta. American Journal of Medical Genetics Part C (Seminars in Medical Genetics), vol. 172C, pp. 367-383, 2016. (Year: 2016).*

(Continued)

*Primary Examiner* — Jennifer Dunston
(74) *Attorney, Agent, or Firm* — Nadya Reingand; Yan Hankin

(57) ABSTRACT

Produced the gene therapy DNA vectors based on the gene therapy DNA vector for treatment of diseases associated with disorders of osteogenesis, formation and regeneration of bone and cartilage tissues, including, in case of bone fractures, increased brittleness of bones, reduction of bones mineralisation, for improvement in osteoinduction of bone implants. The gene therapy DNA vector contains the coding region of the COL1A1, COL1A2, BMP2 or BMP7 therapeutic genes. Methods of producing or use the gene therapy DNA vector carrying therapeutic genes. *Escherichia coli* strain SCS110-AF/VTvaf17-COL1A1, SCS110-AF/VTvaf17-COL1A2, SCS110-AF/VTvaf17-BMP2 or SCS110-AF/VTvaf17-BMP7 obtains by the method described above carrying gene therapy DNA vector VTvaf17-COL1A1, VTvaf17-COL1A2, VTvaf17-BMP2 or VTvaf17-BMP7. The method of producing the gene therapy DNA vector carrying COL1A1, or COL1A2, or BMP2, or BMP7 therapeutic gene uses on an industrial scale.

5 Claims, 18 Drawing Sheets
Specification includes a Sequence Listing.

(56) References Cited

OTHER PUBLICATIONS

Pelled et al. Direct gene therapy for bone regeneration: Gene delivery, animal models, and outcome measures. Tissue Engineering Part B, vol. 16, No. 1, pp. 13-20, 2010. (Year: 2010).*
SCS110 Competent Cells, Catalog #200247, printed from https://www.chem-agilent.com/pdf/strata/200247.pdf, as pp. 1/2-2/2, Revision #074003, 2004. (Year: 2004).*

* cited by examiner

GENE THERAPY BASED ON VECTOR VTVAF17

FIELD OF THE INVENTION

The invention refers to genetic engineering and can be used in biotechnology, medicine, and agriculture for the manufacture of gene therapy products. I.e. the produced gene therapy DNA vector containing the therapeutic gene can be used to deliver it to the cells of human beings and animals that experience reduced or insufficient expression of that gene, thus ensuring the desired therapeutic effect.

REFERENCE TO A SEQUENCE LISTING

SEQ ID NO: 1 through SEQ ID NO: 20, incorporated fully by reference herein, are provided in ASCII format together in one separately enclosed .TXT file, submitted via EFS-Web—File name: SEQ-LISTING576.txt; Date of Creation: Wednesday, May 26, 2021; File size: 33.7 KB.

BACKGROUND OF THE INVENTION

Gene therapy is an innovative approach in medicine aimed at treating inherited and acquired diseases by means of delivery of new genetic material into a patient's cells, tissues, or organs to compensate for or suppress the function of a mutant gene and/or treat a genetic disorder. The objective of gene therapy in most cases is to inject the organism with genes that provide transcription and further translation of protein molecules encoded by these genes. Within the description of the invention, gene expression refers to the production of a protein molecule with amino acid sequence encoded by this gene.

Genes selected from the group of COL1A1, COL1A2, BMP2, and BMP7 genes are essential in the formation of bone and cartilage tissues in human and animal organisms. The correlations between low/insufficient concentrations of these proteins and various human diseases in some cases confirmed by disturbances in normal gene expression encoding these proteins was demonstrated. For example, mutations in the COL1A1 and COL1A2 genes lead to hereditary diseases of the connective tissue, i.e. osteogenesis imperfecta accompanied by frequent bone fractures (Yahyaeva G. T. et al., Current Pediatrics. 2016; 15 (2): 175-179). The genetic deficiency of BMP2 results in increased brittleness of bones, enchondral osteogenesis disorders, and mineralisation of bone matrix (Chen G., Deng C., Li Y. P. Int. J. Biol. Sci. 2012; 8 (2): 272-88). Thus, an increase in expression of a gene selected from the group of COL1A1, COL1A2, BMP2, and BMP7 genes and introduced into the organism using the gene therapy method is relevant for the correction of conditions of humans and animals associated with the defect of action of the above-mentioned genes.

For the purposes of gene therapy, specially constructed gene therapy vectors divided into viral and non-viral are used. Recently, increasingly more attention is paid to the development of non-viral gene delivery systems with plasmid vectors topping the list. These vectors are free of limitations inherent in viral vectors: in the target cell, they exist as an episome without being integrated into the genome; producing them is quite cheap; there is no immune response or side effects caused by the administration of plasmid vectors, which makes them a convenient tool for gene therapy and prevention of the genetic diseases as DNA vaccination (Li L, Petrovsky N. Molecular mechanisms for enhanced DNA vaccine immunogenicity. Expert Rev Vaccines. 2016; 15(3):313-29).

However, limitations of plasmid vectors use in gene therapy are: 1) presence of antibiotic resistance genes for the production of constructs in carrying strains; 2) the presence of various regulatory elements represented by sequences of viral genomes; 3) size of therapeutic plasmid vector that determines the efficiency of vector delivery to the target cell.

It is known that the European Medicines Agency deems it necessary to refrain from adding antibiotic resistance marker genes to newly engineered plasmid vectors for gene therapy (Reflection paper on design modifications of gene therapy medicinal products during development/14 Dec. 2011 EMA/CAT/GTWP/44236/2009 Committee for advanced therapies) and also recommends avoiding the presence of the regulatory elements in the therapeutic plasmid vectors in order to increase the expression of therapeutic genes (promoters, enhancers, post-translational regulatory elements) that are parts of genomes of various viruses (Guideline on the quality, non-clinical and clinical aspects of gene therapy medicinal products/23 Mar. 2015, EMA/CAT/80183/2014, Committee for Advanced Therapies).

The size of the gene therapy vector is also essential. It is known that modern plasmid vectors often have unnecessary, non-functional sites that increase their length substantially (Mairhofer J, Grabherr R. Rational vector design for efficient non-viral gene delivery: challenges facing the use of plasmid DNA. Mol Biotechnol. 2008.39(2):97-104), which sometimes prevents inserting the therapeutic gene of the desired size into the vector.

A method has been known for accumulating plasmid vectors in *Escherichia coli* strains without using antibiotics (Cranenburgh R M, Hanak J A, Williams S G, Sherratt D J. *Escherichia coli* strains that allow antibiotic-free plasmid selection and maintenance by repressor titration. Nucleic Acids Res. 2001. 29(5):E26). DH1lacdapD and DH1lacP2dapD strains of *Escherichia coli* were constructed, where gene dapD encoding 2,3,4,5-tetrahydropyridine-2,6-dicarboxylate-N-succinyltransferase enzyme involved in the biosynthesis of L-lysine is controlled by the lac promoter. In the absence of the inducer IPTG (Isopropyl-β-D-1-thiogalactopyranoside), these strains are subject to lysis. However, the administration of the pORT multicopy plasmid vector containing the lac operon induces expression of gene dapD, and, therefore, transformed clones may be selected and reproduced. These strains, however, feature low levels and instability of transformation.

An invention is reported in Patent Application No. RU2011152377A for the preparation of an expression plasmid vector without the resistance to antibiotics that contains a polynucleotide sequence encoding the repressor protein. The expression of the said repressor protein regulates the expression of the toxic gene product integrated into the region of the *E. coli* genome. However, like any other method of selection based on the use of repressor proteins, this method features unstable and inefficient transformation.

No. U.S. Pat. No. 9,644,211B2 describes a method for producing a vector of the smallest length. This vector does not contain bacterial genome sequences and is produced by parA-mediated recombination in a cultured *E. coli* strain. The disadvantage of this method of producing the shortest vector is the impossibility to use it on an industrial scale.

Production of gene therapy vectors is known and includes nucleotide sequences encoding human structural proteins or growth factors associated with the repair of bone and cartilage tissues. COL1A1 gene encodes type I collagen alpha 1 chain, and COL1A2 gene encodes type I collagen alpha 2 chain that are potentially important in the development of the genetic predisposition to osteoporosis and fragile bones exposed to the risk of breaking. This is due to the fact that type I collagen is found in bones, tendons, ligaments, skin, and other connective tissues.

Application WO2015035395 describes the use of a therapeutic polynucleotide to produce chondrocytes or cartilaginous cells in an individual's joint, while the polynucleotide is constructed based on viral and non-viral vectors with COL1A1 and COL1A2 genes under the promoter control suitable for activity in a nonvascular, non-neuronal, or low oxygen environment.

Bone morphogenetic proteins (BMPs) are the most important factors in repair of bone and cartilage. Proteins of BMP family affect cell membrane receptors and play an important role in the growth regulation, differentiation, and apoptosis of different types of cells, including osteoblasts, chondroblasts, neurons, and epithelial cells. These proteins stimulate an increase in the number of cells and also cause accelerated differentiation of mesenchymal stem cells into chondroblasts and osteoblasts, increase collagen synthesis, increase alkaline phosphatase activity, increase osteocalcin synthesis, stimulate the synthesis of extracellular matrix and its subsequent mineralisation (Katagiri T, Watabe T. Bone Morphogenetic Proteins. Cold Spring Harb Perspect Biol. 2016, 8(6)).

Currently, some members of BMP family are used in medicine. E.g.

modern biological methods of improvement in osteoinduction of bone implants are focused on the delivery of significant concentrations of BMPs on different types of carriers (Lower J W, Rosen V. Bone Morphogenetic Protein-Based Therapeutic Approaches. Cold Spring Harb Perspect Biol. 2018,10(4)). The use of recombinant BMPs for the induction of osteogenesis in the clinic is limited by the rapid degradation of these proteins at the injection site and in bloodstream, as well as by the risk of heterotopic ossification.

The most studied of this group of proteins are BMP-2 and BMP-7 proteins. Patent RU 2408727 describes 3447 bp recombinant plasmid pCollbd-BMP-2 that is included in *Escherichia coli* strain M15 and provides the expression of the recombinant protein Collbd-BMP-2 consisting of the Collbd collagen-binding domain from the human SPARC calcium-dependent extracellular protein, spacer from residues of glycine, and serine and BMP-2 bone morphogenetic protein. The constructed artificial bacterial operon of fusion proteins is under the control of the promoter region of the early promoter of bacteriophage T5. The resulting recombinant plasmid contains a bacterial bla operon encoding beta-lactamase that constitutes a selection marker for the selection of *E. coli* transformants using the counter-selection method.

Source EP2228071 (A1) describes a recombinant vector constructed based on the commercial plasmid VR1012 (J. Hartikka et al. Human Gene Therapy 1996, 7, 1205-1217) expressing BMP-7 protein (fused to a signal peptide to facilitate the secretion of BMP-7 into the extracellular medium) in host cells, as well as pharmaceutical compositions based on such recombinant vectors for treatment of renal disease in mammals. The described vector contains a polynucleotide encoding mammalian or human BMP-7 protein, operably linked to a promoter element. Promoters and enhancers that can be used in this invention include, but are not limited to the following elements: LTR promoters and enhancers of the Rous sarcoma virus, TK HSV-1 gene, SV40 early or late promoters, adenoviral major late promoter (MLP), phosphoglycerate kinase genes, metallothionein genes, α-1-antitrypsin genes, albumin genes, collagenase genes, elastase I genes, β-actin genes, β-globin genes, γ-globin genes, α-fetoprotein genes and muscle creatine kinase genes. The preferred promoter for BMP-7 protein gene expression is cytomegalovirus (CMV-IE) early promoter of human or mouse origin. Thus, in this invention, the promoter has either viral or cellular origin. The vector in the invention may be any suitable recombinant virus or viral vector, such as a pox virus, adenovirus, herpesvirus, baculovirus, retrovirus, etc., or the vector may be a plasmid.

The prototype of this invention in terms of the use of recombinant DNA vectors for gene therapy is U.S. Pat. No. 9,550,998 (B2) describing the method of producing a recombinant vector for genetic immunisation. The resulting vector is a supercoiled plasmid DNA vector that is used for the expression of cloned genes in human and animal cells. The vector contains an origin of replication (origin), regulatory elements comprising human cytomegalovirus promoter and enhancer, and regulatory sequences from the human T-cell lymphotropic virus. The vector is accumulated in a dedicated *E. coli* strain free of antibiotics through antisense complementation of sacB gene administered into the strain by means of bacteriophage. The use of this DNA vector in gene therapy is limited by the presence of regulatory sequences of viral genomes.

SUMMARY

The purpose of this invention is to construct gene therapy DNA vectors based on a specially constructed gene therapy DNA vector to increase the expression level of a gene selected from the group of genes, namely COL1A1 gene of type I collagen alpha 1 chain, COL1A2 gene of type I collagen alpha 2 chain, bone morphogenetic protein BMP-2 gene, and bone morphogenetic protein BMP-7 gene, as well as to construct strains carrying these gene therapy DNA vectors for their production on an industrial scale.

At the same time, DNA vectors must combine the following properties in the optimal way:

I) possibility of safe use in the gene therapy of human beings and animals due to the absence of antibiotic resistance genes in the gene therapy DNA vector, II) length that ensures efficient gene delivery to the target cell, III) presence of regulatory elements that ensure efficient expression of the therapeutic genes while not being represented by nucleotide sequences of viral genomes, IV) producibility and constructability on an industrial scale.

Items I and III are provided herein in compliance with the requirements of the state regulators for gene therapy medicines and, specifically, the requirement of the European Medicines Agency.

The specified purpose is achieved by using the produced gene therapy DNA vector based on the gene therapy DNA vector VTvaf17 for treatment of diseases associated with disorders of osteogenesis, formation and regeneration of bone and cartilage tissues, caused by deregulation of growth, differentiation, and apoptosis of multiple types of cells, including osteoblasts and chondroblasts, slower differentiation of mesenchymal stem cell into chondroblasts and osteoblasts, decrease of collagen synthesis, alkaline phosphatase activity, osteocalcin synthesis, synthesis of extracellular matrix and its subsequent mineralisation, including, inter alia, in case of bone fractures, increased brittleness of bones, reduction of bones mineralisation, for improvement in osteoinduction of bone implants via the increase of expression of COL1A1, or COL1A2, or BMP2, or BMP7 therapeutic gene in humans and animals.

This gene therapy DNA vector that has the coding region of COL1A1 therapeutic gene cloned to gene therapy DNA vector VTvaf17 resulting in gene therapy DNA vector VTvaf17-COL1A1 that has nucleotide sequence SEQ ID NO: 1, gene therapy DNA vector that has the coding region of COL1A2 therapeutic gene cloned to gene therapy DNA vector VTvaf17 resulting in gene therapy DNA vector VTvaf17-COL1A2 that has nucleotide sequence SEQ ID NO: 2, gene therapy DNA vector that has the coding region of BMP2 therapeutic gene cloned to gene therapy DNA vector VTvaf17 resulting in gene therapy DNA vector VTvaf17-BMP2 that has nucleotide sequence SEQ ID NO: 3, gene therapy DNA vector that has the coding region of BMP7 therapeutic gene cloned to gene therapy DNA vector VTvaf17 resulting in gene therapy DNA vector VTvaf17-BMP7 that has nucleotide sequence SEQ ID NO: 4.

Each of the constructed gene therapy DNA vectors based on gene therapy DNA vector VTvaf17 carrying the COL1A1, COL1A2, BMP2, or BMP7 therapeutic gene namely gene therapy DNA vectors VTvaf17-COL1A1, or VTvaf17-COL1A2, or VTvaf17-BMP2, or VTvaf17-BMP7 due to the limited size of VTvaf17 vector part not exceeding 3200 bp has the ability to efficiently penetrate into human and animal cells and express the therapeutic gene selected from the group of COL1A1, COL1A2, BMP2, or BMP7 genes. At the same time, nucleotide sequences that are not antibiotic resistance genes, virus genes, or regulatory elements of viral genomes are used as structure elements, which ensures its safe use for gene therapy in humans and animals.

A method of gene therapy DNA vector production based on gene therapy DNA vector VTvaf17 carrying the COL1A1, or COL1A2, or BMP2, or BMP7 therapeutic gene has been also developed that involves obtaining each of gene therapy DNA vectors: VTvaf17-COL1A1, or VTvaf17-COL1A2, or VTvaf17-BMP2, or VTvaf17-BMP7 as follows: the coding region of the COL1A1, or COL1A2, or BMP2, or BMP7 therapeutic gene is cloned to DNA vector VTvaf17, and gene therapy DNA vector VTvaf17-COL1A1, SEQ ID NO: 1, or VTvaf17-COL1A2, SEQ ID NO: 2 or VTvaf17-BMP2, SEQ ID NO: 3, or VTvaf17-BMP7, SEQ ID NO: 4, respectively, is obtained.

The method of use of the constructed gene therapy DNA vector based on gene therapy DNA vector VTvaf17 carrying the COL1A1, or COL1A2, or BMP2, or BMP7 therapeutic gene for treatment of diseases associated with disorders of osteogenesis, formation and regeneration of bone and cartilage tissues, caused by deregulation of growth, differentiation, and apoptosis of multiple types of cells, including osteoblasts and chondroblasts, slower differentiation of mesenchymal stem cell into chondroblasts and osteoblasts, decrease of collagen synthesis, alkaline phosphatase activity, osteocalcin synthesis, synthesis of extracellular matrix and its subsequent mineralisation, including, inter alia, in case of bone fractures, increased brittleness of bones, reduction of bones mineralisation, for improvement in osteoinduction of bone implants via the increase of expression of COL1A1, or COL1A2, or BMP2, or BMP7 therapeutic gene in humans and animals is to transfect cells of human or animal organs and tissues with the selected gene therapy DNA vector carrying the therapeutic gene based on gene therapy DNA vector VTvaf17 or several selected gene therapy DNA vectors carrying the therapeutic genes based on gene therapy DNA vector VTvaf17 of the constructed gene therapy DNA vectors carrying therapeutic genes based on gene therapy DNA vector VTvaf17, and/or to inject human or animal autologous cells of said patient or animal transfected with the selected gene therapy DNA vector carrying the therapeutic gene based on gene therapy DNA vector VTvaf17 or several selected gene therapy DNA vectors carrying the therapeutic genes based on gene therapy DNA vector VTvaf17 of the constructed gene therapy DNA vectors carrying therapeutic genes into human or animal organs and tissues, or to use a combination of the indicated methods.

The method of production of strain for construction of a gene therapy DNA vector for treatment of diseases associated with disorders of osteogenesis, formation and regeneration of bone and cartilage tissues, caused by deregulation of growth, differentiation, and apoptosis of multiple types of cells, including osteoblasts and chondroblasts, slower differentiation of mesenchymal stem cell into chondroblasts and osteoblasts, decrease of collagen synthesis, alkaline phosphatase activity, osteocalcin synthesis, synthesis of extracellular matrix and its subsequent mineralisation, including, inter alia, in case of bone fractures, increased brittleness of bones, reduction of bones mineralisation, for improvement in osteoinduction of bone implants via the increase of expression of COL1A1, or COL1A2, or BMP2, or BMP7 therapeutic gene in humans and animals involves making electrocompetent cells of *Escherichia coli* strain SCS110-AF and subjecting these cells to electroporation with the constructed gene therapy DNA vector and subsequent selection of stable clones of the strain using selective medium.

*Escherichia coli* strains SCS110-AF/VTvaf17-COL1A1, or *Escherichia coli* strain CS110-AF/VTvaf17-COL1A2, or *Escherichia coli* strain SCS110-AF/VTvaf17-BMP2, or *Escherichia coli* strain SCS110-AF/VTvaf17-BMP7 carrying gene therapy DNA vectors VTvaf17-COL1A1, or VTvaf17-COL1A2, or VTvaf17-BMP2, or VTvaf17-BMP7, respectively, for production thereof are claimed.

The method of production on an industrial scale of gene therapy DNA vector based on gene therapy DNA vector VTvaf17 carrying the COL1A1, or COL1A2, or BMP2, or BMP7 therapeutic gene for treatment of diseases associated with disorders of osteogenesis, formation and regeneration of bone and cartilage tissues, caused by deregulation of growth, differentiation, and apoptosis of multiple types of cells, including osteoblasts and chondroblasts, slower differentiation of mesenchymal stem cell into chondroblasts and osteoblasts, decrease of collagen synthesis, alkaline phosphatase activity, osteocalcin synthesis, synthesis of extracellular matrix and its subsequent mineralisation, including, inter alia, in case of bone fractures, increased brittleness of bones, reduction of bones mineralisation, for improvement in osteoinduction of bone implants via the increase of expression of COL1A1, or COL1A2, or BMP2, or BMP7 therapeutic gene in humans and animals involves scaling-up the bacterial culture of the strain to the quantities necessary for increasing the bacterial biomass in an industrial fermenter, after which the biomass is used to extract a fraction containing the therapeutic DNA product, i.e. the gene therapy DNA vector VTvaf17-COL1A1, or VTvaf17-COL1A2, or VTvaf17-BMP2, or VTvaf17-BMP7, and then multi-stage filtered, and purified by chromatographic methods.

BRIEF DESCRIPTION OF THE DRAWINGS

The essence of the invention is explained in the drawings, where

FIGS. 1A-1D show the structures corresponding to:
1A—gene therapy DNA vector VTvaf17-COL1A1,
1B—gene therapy DNA vector VTvaf17-COL1A2,
1C—gene therapy DNA vector VTvaf17-BMP2,
1D—gene therapy DNA vector VTvaf17-BMP7.

The following structural elements of the vector are indicated in the structures:

EF1a—the promoter region of human elongation factor EF1A with an intrinsic enhancer contained in the first intron of the gene. It ensures efficient transcription of the recombinant gene in most human tissues.

The reading frame of the therapeutic gene corresponding to the coding region of the COL1A1 gene (FIG. 1A), or COL1A2 (FIG. 1B), or BMP2 (FIG. 1C), or BMP7 (FIG. 1D), respectively, hGH-TA—the transcription terminator and the polyadenylation site of the human growth factor gene, (4) RNA-out—the regulatory element RNA-OUT of transposon Tn 10 allowing for antibiotic-free positive selection in case of the use of *Escherichia coli* strain SCS 110-AF, ori—the origin of replication, the site for autonomous replication with a single nucleotide substitution to increase plasmid production in the cells of most *Escherichia coli* strains.

Unique restriction sites of *Escherichia coli* are marked.

Figure 2:
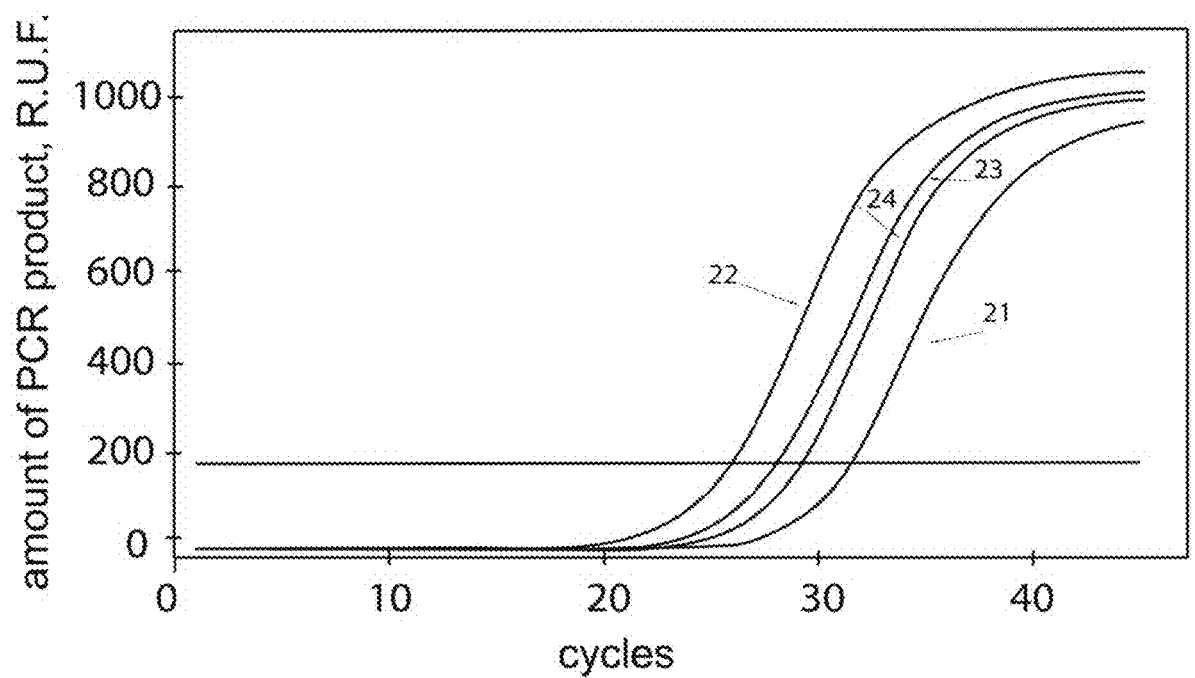

FIG. 2 shows diagrams of mRNA accumulation of the therapeutic gene, namely the human COL1A1 gene in HDFa human primary dermal fibroblast cells (ATCC PCS-201-012) before their transfection and 48 hours after transfection of these cells with the DNA vector VTvaf17-COL1A1 in order to confirm the efficiency of gene therapy DNA vector VTvaf17-COL1A1 carrying the COL1A1 therapeutic gene, where 21—cDNA of COL1A1 gene before transfection with gene therapy DNA vector VTvaf17-COL1A1,
22—cDNA of COL1A1 gene after transfection with gene therapy DNA vector VTvaf17-COL1A1,
23—cDNA of B2M gene before transfection with gene therapy DNA vector VTvaf17-COL1A1,
24—cDNA of B2M gene after transfection with gene therapy DNA vector VTvaf17-COL1A1.

B2M (beta-2-microglobuline) gene listed in the GENBANK database under number NM 004048.2 was used as a reference gene.

Figure 3:
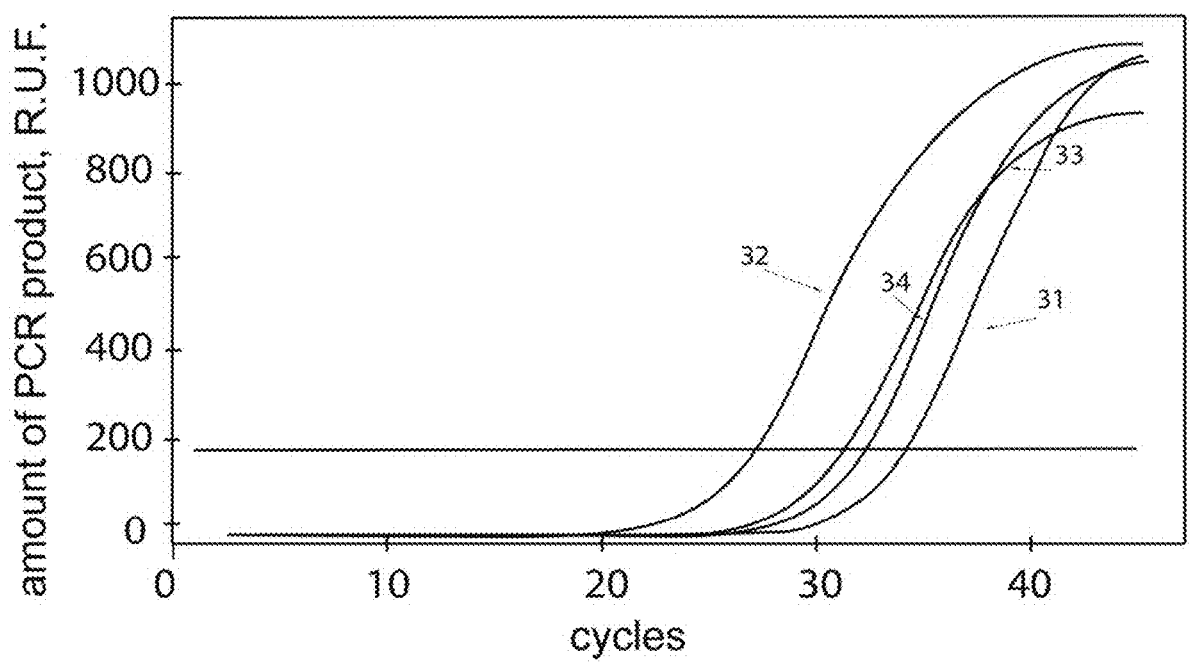

FIG. 3 shows diagrams of mRNA accumulation of the therapeutic gene, namely the human COL1A2 gene in human dermal fibroblast cells before their transfection and 48 hours after transfection of these cells with the DNA vector VTvaf17-COL1A2 in order to confirm the efficiency of gene therapy DNA vector VTvaf17-COL1A2 carrying the COL1A2 therapeutic gene, where 31—cDNA of COL1A2 gene before transfection with gene therapy DNA vector VTvaf17-COL1A2,
32—cDNA of COL1A2 gene after transfection with gene therapy DNA vector VTvaf17-COL1A2,
33—cDNA of B2M gene before transfection with gene therapy DNA vector VTvaf17-COL1A2,
34—cDNA of B2M gene after transfection with gene therapy DNA vector VTvaf17-COL1A2.

Figure 4:
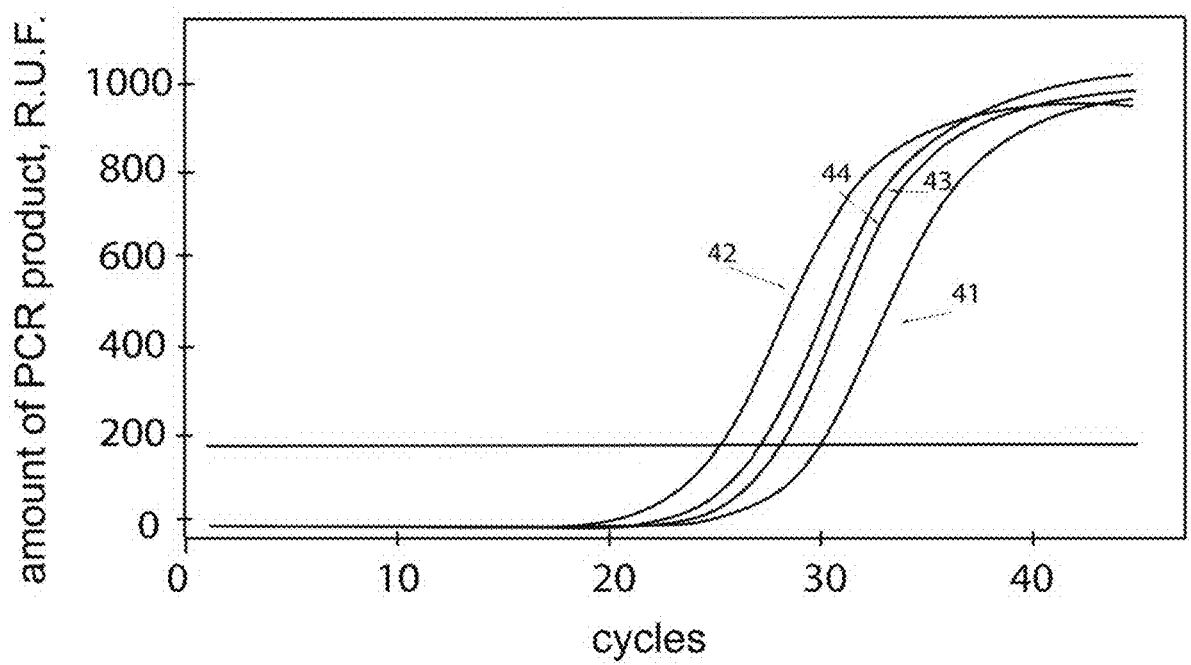

B2M (beta-2-microglobuline) gene listed in the GENBANK database under number NM 004048.2 was used as a reference gene, where FIG. 4 shows diagrams of mRNA accumulation of the therapeutic gene, namely the human BMP2 gene in MG-63 human osteosarcoma cells (ATCC CRL-1427) before their transfection and 48 hours after transfection of these cells with the DNA vector VTvaf17-BMP2 in order to confirm the efficiency of gene therapy DNA vector VTvaf17-BMP2 carrying the BMP2 therapeutic gene, where 41—cDNA of BMP2 gene before transfection with gene therapy DNA vector VTvaf17-BMP2,
42—cDNA of BMP2 gene after transfection with gene therapy DNA vector VTvaf17-BMP2,
43—cDNA of B2M gene before transfection with gene therapy DNA vector VTvaf17-BMP2,
44—cDNA of B2M gene after transfection with gene therapy DNA vector VTvaf17-BMP2.

B2M (beta-2-microglobuline) gene listed in the GENBANK database under number NM 004048.2 was used as a reference gene.

Figure 5:
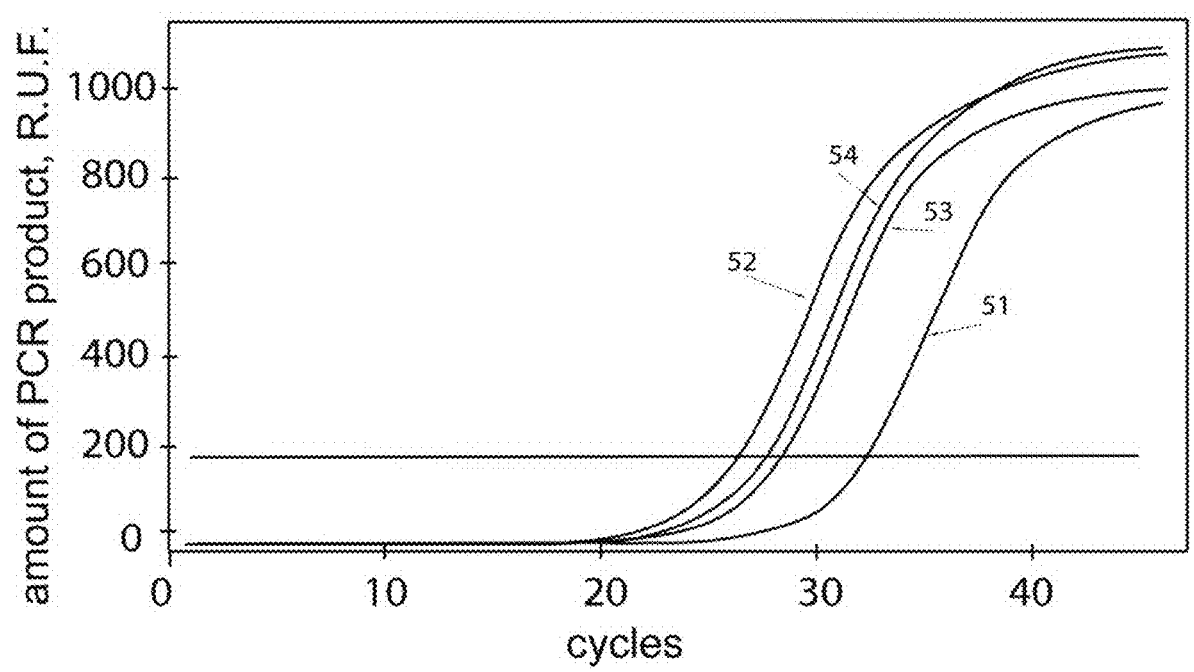

FIG. 5 shows diagrams of mRNA accumulation of the therapeutic gene, namely the human BMP7 gene in hFOB 1.19 human osteoblast cells (ATCC CRL-11372) before their transfection and 48 hours after transfection of these cells with the DNA vector VTvaf17-BMP7 in order to confirm the efficiency of gene therapy DNA vector VTvaf17-BMP7 carrying the BMP7 therapeutic gene, where 51—cDNA of BMP7 gene before transfection with gene therapy DNA vector VTvaf17-BMP7,
52—cDNA of BMP7 gene after transfection with gene therapy DNA vector VTvaf17-BMP7,
53—cDNA of B2M gene before transfection with gene therapy DNA vector VTvaf17-BMP7,
54—cDNA of B2M gene in cells after transfection with gene therapy DNA vector VTvaf17-BMP7.

B2M (beta-2-microglobuline) gene listed in the GENBANK database under number NM 004048.2 was used as a reference gene.

Figure 6:
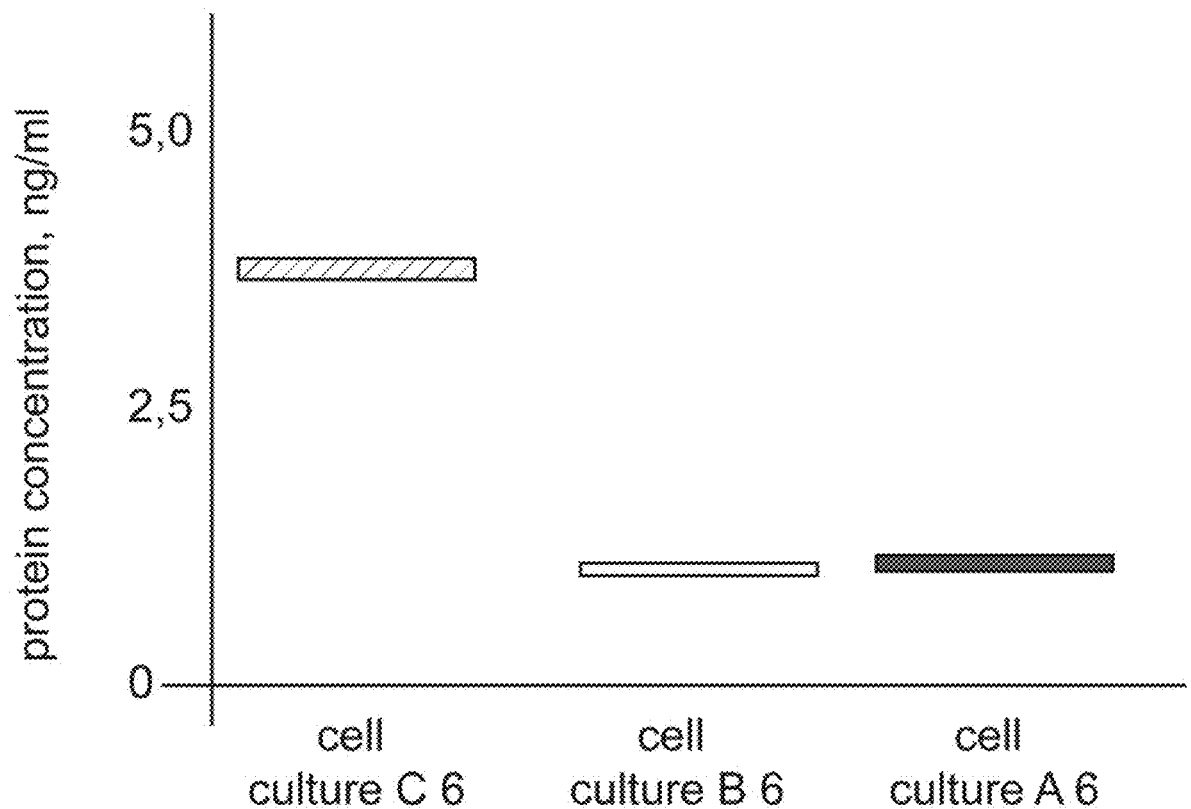

FIG. 6 shows the plot of type I collagen alpha 1 chain protein concentration in the culture medium of HDFa human primary dermal fibroblast cells (ATCC PCS-201-012) after transfection of these cells with the DNA vector VTvaf17-COL1A1 in order to assess changes in the type I collagen alpha 1 chain protein concentration in the culture medium of HDFa human primary dermal fibroblast cells upon transfection of these cells with DNA vector VTvaf17-COL1A1 carrying the COL1A1 gene, where culture A6—HDFa human primary dermal fibroblast cells transfected with aqueous dendrimer solution without plasmid DNA (reference), culture B6—HDFa human primary dermal fibroblast cells transfected with DNA vector VTvaf17, culture C6—HDFa human primary dermal fibroblast cells transfected with DNA vector VTvaf17-COL1A1 carrying the COL1A1 gene.

Figure 7:
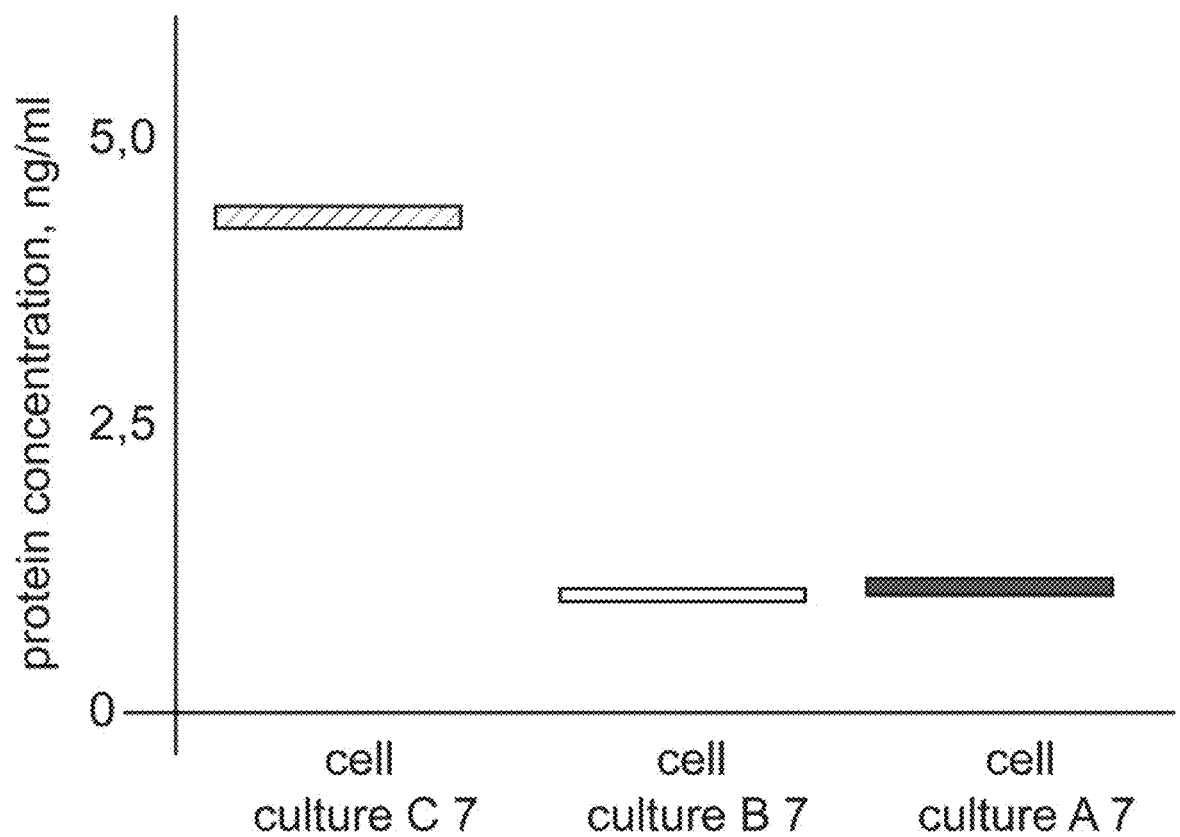

FIG. 7 shows the plot of type I collagen alpha 2 chain protein concentration in the culture medium of human dermal fibroblast cells after transfection of these cells with the DNA vector VTvaf17-COL1A2 in order to assess changes in the type I collagen alpha 2 chain protein concentration in the culture medium of primary human dermal fibroblast cells upon transfection of these cells with DNA vector VTvaf17-COL1A2 carrying the COL1A2 gene, where culture A7—human dermal fibroblasts transfected with aqueous dendrimer solution without plasmid DNA (reference), culture B7—human dermal fibroblasts transfected with DNA vector VTvaf17, culture C7—human dermal fibroblasts transfected with DNA vector VTvaf17-COL1A2 carrying the COL1A2 gene.

Figure 8:
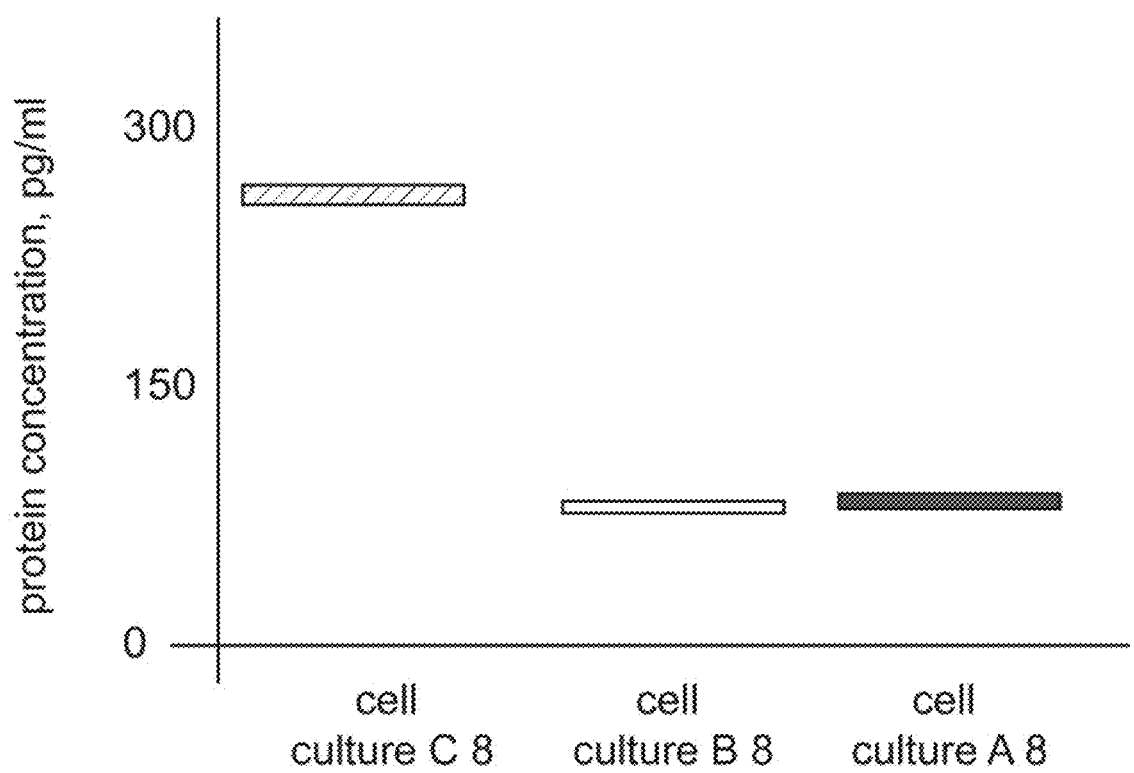

FIG. 8 shows the plot of bone morphogenetic protein 2 concentration in the culture medium of MG-63 human osteosarcoma cells (ATCC CRL-1427) after transfection of these cells with DNA vector VTvaf17-BMP2 in order to assess changes in the bone morphogenetic protein 2 concentration in the culture medium of MG-63 human osteosarcoma cells (ATCC CRL-1427) upon transfection of these cells with DNA vector VTvaf17-BMP2 carrying the BMP2 gene, where culture A8—culture of MG-63 human osteosarcoma cells transfected with aqueous dendrimer solution without plasmid DNA (reference), culture B8—culture of MG-63 human osteosarcoma cells transfected with DNA vector VTvaf17, culture C8—culture of MG-63 human osteosarcoma cells transfected with DNA vector VTvaf17-BMP2 carrying the BMP2 gene.

Figure 9:
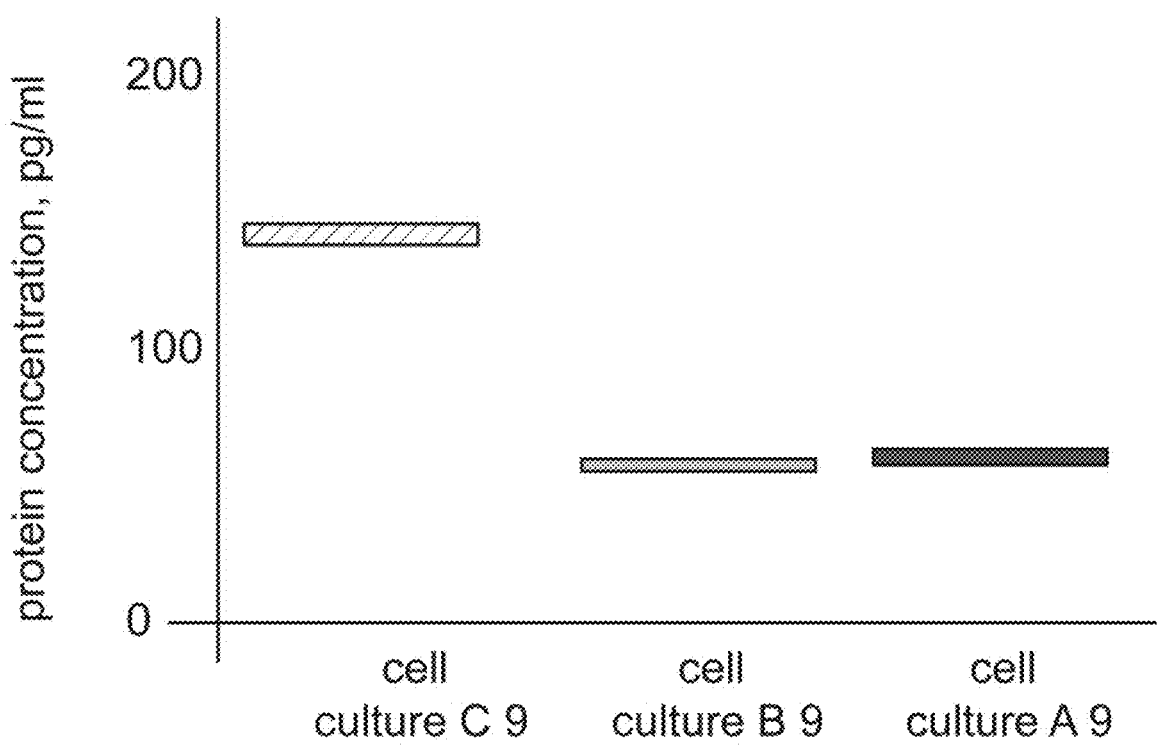

FIG. 9 shows the plot of bone morphogenetic protein 7 concentration in the culture medium of hFOB 1.19 human osteoblast cells (ATCC CRL-11372) after transfection of these cells with DNA vector VTvaf17-BMP7 in order to assess changes in the bone morphogenetic protein 7 concentration in the culture medium of hFOB 1.19 human osteoblast cells (ATCC CRL-11372) upon transfection of these cells with DNA vector VTvaf17-BMP7 carrying the BMP7 gene, where culture A9—culture of hFOB 1.19 human osteoblast cells transfected with aqueous dendrimer solution without plasmid DNA (reference), culture B9—culture of hFOB 1.19 human osteoblast cells transfected with DNA vector VTvaf17, culture C9—culture of hFOB 1.19 human osteoblast cells transfected with DNA vector VTvaf17-BMP7 carrying the BMP7 gene.

Figure 10:
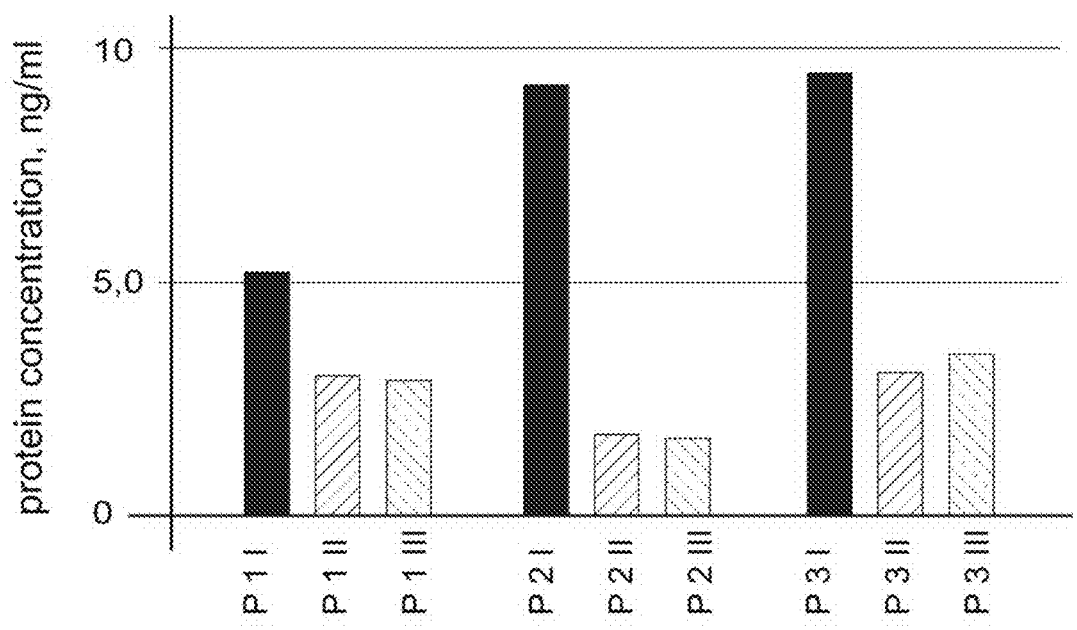

FIG. 10 shows the plot of COL1A2 protein concentration in the skin biopsy specimens of three patients after injection of gene therapy DNA vector VTvaf17-COL1A2 into the skin of these patients in order to assess the functional activity, i.e. the expression of the therapeutic gene at the protein level, and the possibility of increasing the level of protein expression using gene therapy DNA vector based on gene therapy vector VTvaf17 carrying the COL1A2 therapeutic gene.

The following elements are indicated in FIG. 10:
P1I—patient P1 skin biopsy in the region of injection of gene therapy DNA vector VTvaf17-COL1A2,
P1II—patient P1 skin biopsy in the region of injection of gene therapy DNA vector VTvaf17 (placebo),
P1III—patient P1 skin biopsy from intact site,
P2I—patient P2 skin biopsy in the region of injection of gene therapy DNA vector VTvaf17-COL1A2,
P2II—patient P2 skin biopsy in the region of injection of gene therapy DNA vector VTvaf17 (placebo),
P2III—patient P2 skin biopsy from intact site,
P3I—patient P3 skin biopsy in the region of injection of gene therapy DNA vector VTvaf17-COL1A2,
P3II—patient P3 skin biopsy in the region of injection of gene therapy DNA vector VTvaf17 (placebo),
P3III—patient P3 skin biopsy from intact site.

Figure 11:
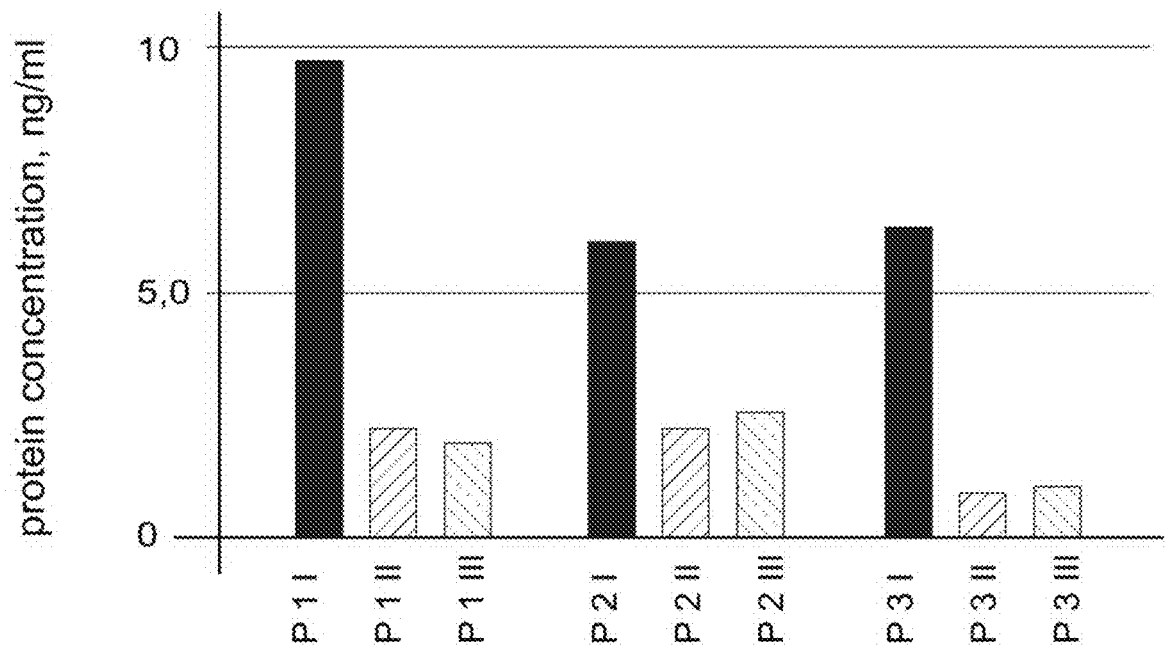

FIG. 11 shows the plot of COL1A1 protein concentration in the cartilage biopsy specimens of three patients after injection of gene therapy DNA vector VTvaf17-COL1A1 into the cartilage tissue of these patients in order to assess the functional activity, i.e. the expression of the therapeutic gene at the protein level, and the possibility of increasing the level of protein expression using gene therapy DNA vector based on gene therapy vector VTvaf17 carrying the COL1A1 therapeutic gene.

The following elements are indicated in FIG. 11:
P1I—patient P1 cartilage biopsy in the region of injection of gene therapy DNA vector VTvaf17-COL1A1,
P1II—patient P1 cartilage biopsy in the region of injection of gene therapy DNA vector VTvaf17 (placebo),
P1III—patient P1 cartilage biopsy from intact site,
P2I—patient P2 cartilage biopsy in the region of injection of gene therapy DNA vector VTvaf17-COL1A1,
P2II—patient P2 cartilage biopsy in the region of injection of gene therapy DNA vector VTvaf17 (placebo),
P2III—patient P2 cartilage biopsy from intact site,
P3I—patient P3 cartilage biopsy in the region of injection of gene therapy DNA vector VTvaf17-COL1A1,
P3II—patient P3 cartilage biopsy in the region of injection of gene therapy DNA vector VTvaf17 (placebo),
P3III—patient P3 cartilage biopsy from intact site.

Figure 12:
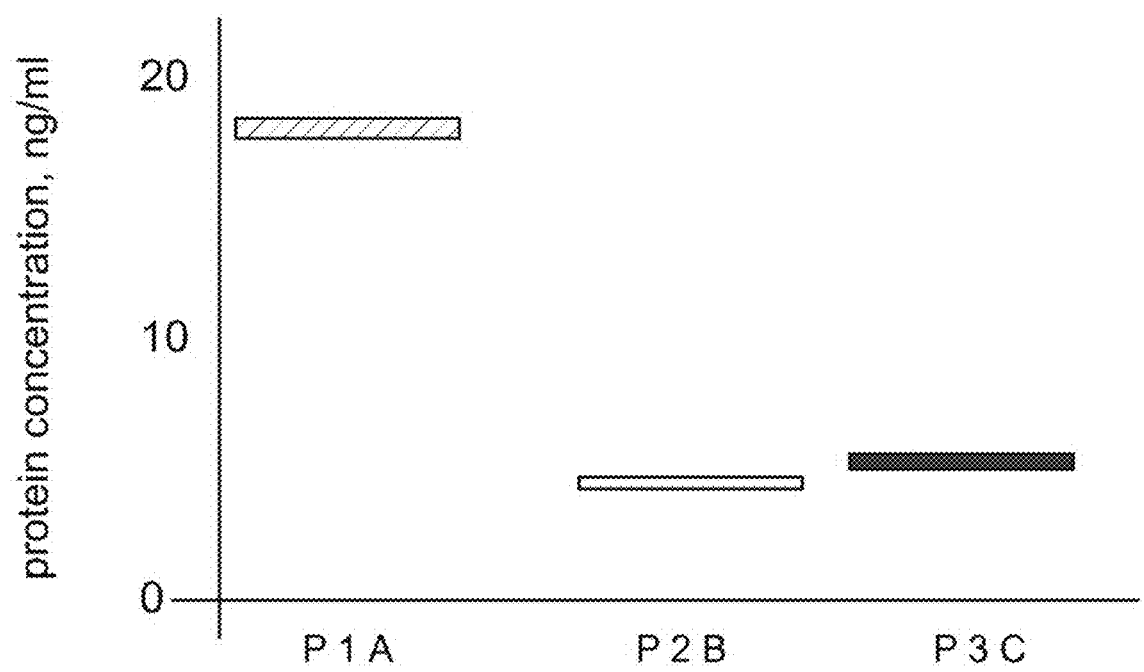

FIG. 12 shows the plot of COL1A1 protein concentration in human skin biopsy specimens after injection of the skin with autologous fibroblast cell culture transfected with the gene therapy DNA vector VTvaf17-COL1A1 in order to demonstrate the method of usage by introducing autologous cells transfected with the gene therapy DNA vector VTvaf17-COL1A1, The following elements are indicated in FIG. 12:
P1A—patient P1 skin biopsy in the region of injection of autologous fibroblast culture of the patient transfected with gene therapy DNA vector VTvaf17-COL1A1,
P1B—patient P1 skin biopsy in the region of injection of autologous fibroblasts of the patient transfected with gene therapy DNA vector VTvaf17,
P1C—patient P1 skin biopsy from intact site.

Figure 13A:
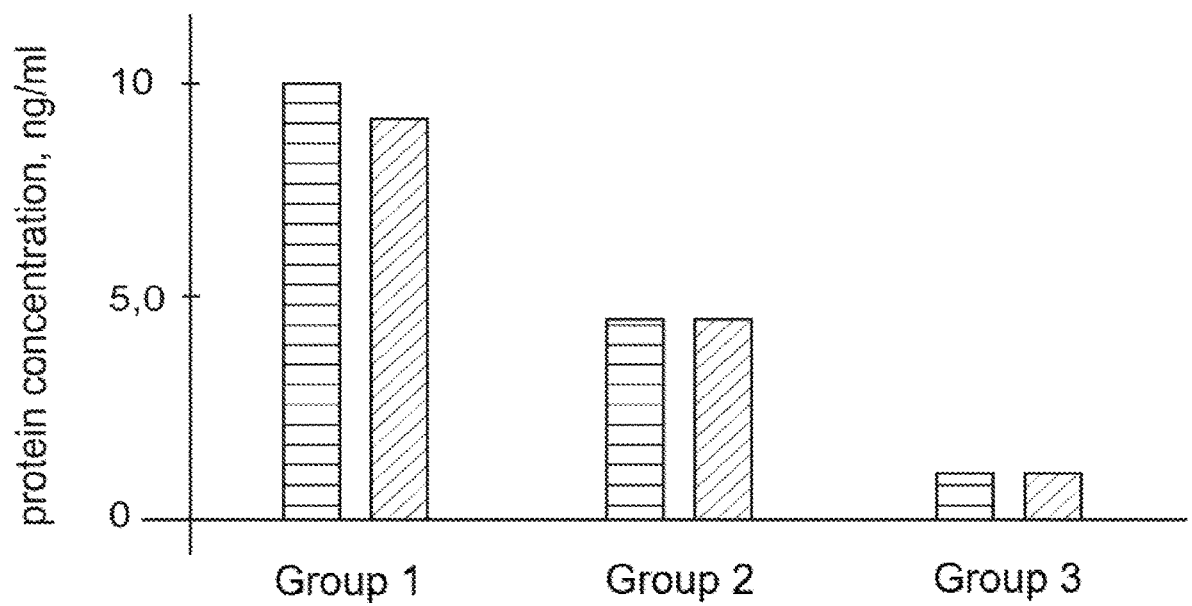

FIG. 13A shows the plot of change in the concentration of type I collagen alpha 1 chain (COL1A1) protein and type I collagen alpha 2 chain (COL1A2) protein in rat bone biopsy specimens in the surgically modelled injury area after injection of the injured area of the rat:
in group 1—with a mixture of gene therapy DNA vectors VTvaf17-COL1A1, VTvaf17-COL1A2, VTvaf17-BMP2, and VTvaf17-BMP7,
in group 2—with crude calcium phosphate precipitate of gene therapy DNA vectors VTvaf17-COL1A1, VTvaf17-COL1A2, VTvaf17-BMP2, and VTvaf17-BMP7,
in group 3 (control)—with saline.

| LEGEND | |
|---|---|
|  | COL1A1 |
|  | COL1A2 |

Figure 13B:
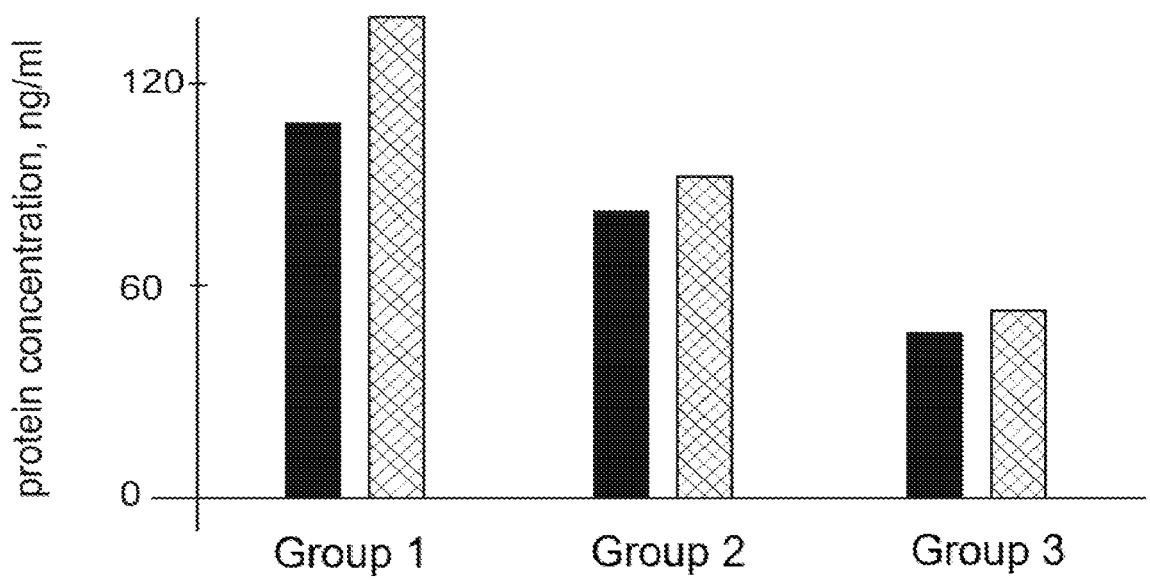

FIG. 13B shows the plot of change in the concentration of bone morphogenetic protein 2 (BMP2) and bone morphogenetic protein 7 (BMP7) in rat bone biopsy specimens in the surgically modelled injury area after injection of the injured area of the rat:
in group 1—with a mixture of gene therapy DNA vectors VTvaf17-COL1A1, VTvaf17-COL1A2, VTvaf17-BMP2, and VTvaf17-BMP7,
in group 2—with crude calcium phosphate precipitate of gene therapy DNA vectors VTvaf17-COL1A1, VTvaf17-COL1A2, VTvaf17-BMP2, and VTvaf17-BMP7,
in group 3 (control)—with saline.

LEGEND

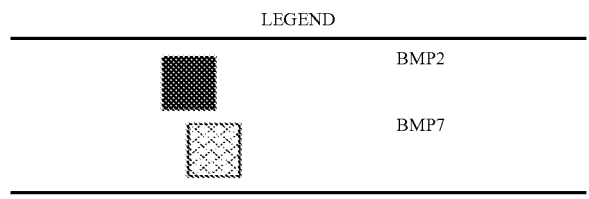

BMP2

BMP7

Figure 14:
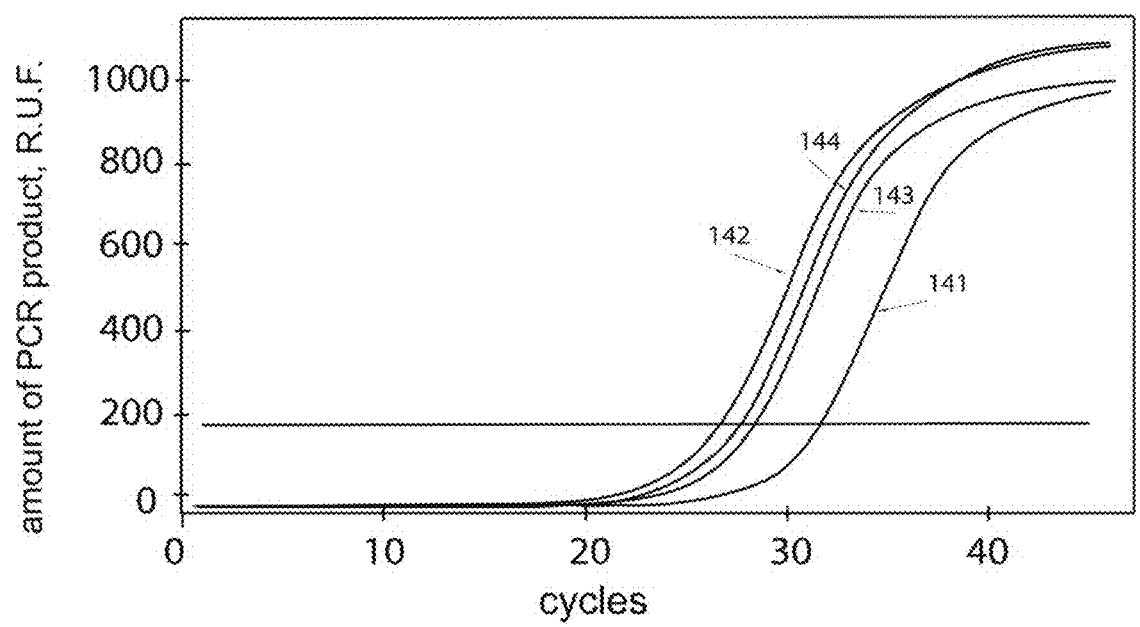

FIG. 14 shows diagrams of accumulation of mRNA of the BMP2 therapeutic gene in the culture medium of CnOb canine osteoblasts before transfection with DNA vector VTvaf17-BMP2 and 48 hours after transfection of these cells with DNA vector VTvaf17-BMP2, where
141—cDNA of BMP2 gene in CnOb canine osteoblasts before transfection with DNA vector VTvaf17-BMP2,
142—cDNA of BMP2 gene in CnOb canine osteoblasts after transfection with DNA vector VTvaf17-BMP2,
143—cDNA of ACT gene in CnOb canine osteoblasts before transfection with DNA vector VTvaf17-BMP2,
144—cDNA of ACT gene in CnOb canine osteoblasts after transfection with DNA vector VTvaf17-BMP2.

Canine actin gene (ACT) listed in the GENBANK database under number DQ131478.1 was used as a reference gene.

EMBODIMENT OF THE INVENTION

Gene therapy DNA vectors carrying the following therapeutic human genes—type I collagen alpha 1 chain COL1A1 gene, or type I collagen alpha 2 chain COL1A2 gene, or bone morphogenetic protein BMP-2 gene, or bone morphogenetic protein BMP-7 gene were constructed based on 3165 bp gene therapy DNA vector VTvaf17 designed to increase the expression level of these therapeutic genes in human and animal tissues. The method of production of each gene therapy DNA vector carrying human therapeutic genes involves cloning of the protein coding sequence of the therapeutic gene to the polylinker of the gene therapy DNA vector VTvaf17 selected from the group of the following genes: COL1A1, COL1A2, BMP2, and BMP7.

The method of production of gene therapy DNA vector based on gene therapy DNA vector VTvaf17 carrying the therapeutic gene selected from the group of COL1A1, COL1A2, BMP2, and BMP7 is performed as follows:
1. the coding region of COL1A1 gene (4422 bp), or COL1A2 gene (4128 bp), or BMP2 gene (1219 bp), or BMP7 gene (1322 bp) is obtained by isolating total RNA from a biological sample of normal tissue, followed by a reverse transcription reaction and PCR amplification using the oligonucleotides obtained by the chemical synthesis method for this purpose, followed by the cleavage of amplification product by restriction endonucleases NheI and HindiII,
2. the coding region of COL1A1, or COL1A2, or BMP2, or BMP7 therapeutic genes is cloned to the polylinker of gene therapy DNA vector VTvaf17 by NheI and HindIII sites to produce gene therapy DNA vector VTvaf17-COL1A1, SEQ ID NO: 1, or VTvaf17-COL1A2, SEQ ID NO: 2, or VTvaf17-BMP2, SEQ ID NO: 3, or VTvaf17-BMP7, SEQ ID NO: 4. The obtained gene therapy DNA vector VTvaf17 carrying the therapeutic gene selected from the group of COL1A1, COL1A2, BMP2, and BMP7 genes was transformed by electroporation of *Escherichia coli* strain SCS110-AF, with antibiotic-free selection of the obtained clones.
3. in order to confirm the efficiency of the constructed gene therapy DNA vector VTvaf17-COL1A1, SEQ ID NO: 1, or VTvaf17-COL1A2, SEQ ID NO: 2, or VTvaf17-BMP2, SEQ ID NO: 3, or VTvaf17-BMP7, SEQ ID NO: 4 the following was assessed:
    a. change in mRNA accumulation of therapeutic genes in the human cells after transfection of different cell lines with gene therapy DNA vectors (by real-time PCR-RT-PCR),
    b. change in the quantitative level of therapeutic proteins in the human cell culture medium after transfection of different cell lines with gene therapy DNA vectors (using enzyme-linked immunosorbent assay ELISA),
    c. change in the quantitative level of therapeutic proteins in the supernatant of human and animals tissue biopsy specimens after the injection of gene therapy DNA vectors into these tissues (using ELISA),
    d. change in the quantitative level of therapeutic proteins in the supernatant of human tissue biopsies after the injection of these tissues with autologous cells of this human transfected with gene therapy DNA vectors (using ELISA).
4. In order to confirm the practicability of use of the constructed gene therapy DNA vector VTvaf17-COL1A1, SEQ ID NO: 1, or VTvaf17-COL1A2, SEQ ID NO: 2, or VTvaf17-BMP2, SEQ ID NO: 3, or VTvaf17-BMP7, SEQ ID NO: 4, the following was performed:
    a. transfection of different human cell lines with gene therapy DNA vectors,
    b. injection of gene therapy DNA vectors into different human and animal tissues,
    c. injection of a mixture of gene therapy DNA vectors into animal tissues,
    d. injection of autologous cells transfected with gene therapy DNA vectors into human tissues.
5. In order to confirm the production of *Escherichia coli* strain SCS110-AF/VTvaf17-COL1A1, or *Escherichia coli* strain SCS110-AF/VTvaf17-COL1A2, or *Escherichia coli* strain SCS110-AF/VTvaf17-BMP2, or *Escherichia coli* strain SCS110-AF/VTvaf17-BMP7, transformation, selection, and subsequent biomass growth with extraction of plasmid DNA were performed.
6. To confirm the producibility and constructability on an industrial scale of gene therapy DNA vector VTvaf17-COL1A1, SEQ ID NO: 1, or VTvaf17-COL1A2, SEQ ID NO: 2, or VTvaf17-BMP2, SEQ ID NO: 3, or VTvaf17-BMP7, SEQ ID NO: 4, the following was performed:
    a. fermentation on an industrial scale of *Escherichia coli* strain SCS110-AF/VTvaf17-COL1A1, or *Escherichia coli* strain SCS110-AF/VTvaf17-COL1A2, or *Escherichia coli* strain SCS110-AF/VTvaf17-BMP2, or *Escherichia coli* strain SCS110-AF/VTvaf17-BMP7 each containing gene therapy DNA vector VTvaf17 carrying a protein-coding sequence of the therapeutic gene selected from the group of COL1A1, COL1A2, BMP2, and BMP7 genes.

Example 1

Production of gene therapy DNA vector VTvaf17-COL1A1 carrying the COL1A1 therapeutic gene.

Gene therapy DNA vector VTvaf17-COL1A1 was constructed by cloning the coding region of the COL1A1 gene to the DNA vector VTvaf17 by NheI and HindIII restriction sites. The coding region of COL1A1 gene (4422 bp) was obtained by isolating total RNA from the biological human tissue sample followed by reverse transcription reaction using commercial kit Mint-2 (Evrogen, Russia) and constructed oligonucleotides

```
COL1A1_F CCAGCTAGCGTCTAGGGTCTAGACATGTTC,

COL1A1_R TATAAGCTTCTACAGGAAGCAGACAGGGCCAAC
```

And PCR amplification using the commercially available kit Phusion® High-Fidelity DNA Polymerase (New England Biolabs, USA) and constructed oligonucleotides

```
COL1A1_SF TGACGAGACCAAGAACTGCC,

COL1A1_SR GCACCATCATTTCCACGAGC,
```

The amplification product of the coding region of COL1A1 gene and DNA vector VTvaf17 was cleaved by NheI and HindIII restriction endonucleases (New England Biolabs, USA).

Figure 1A:
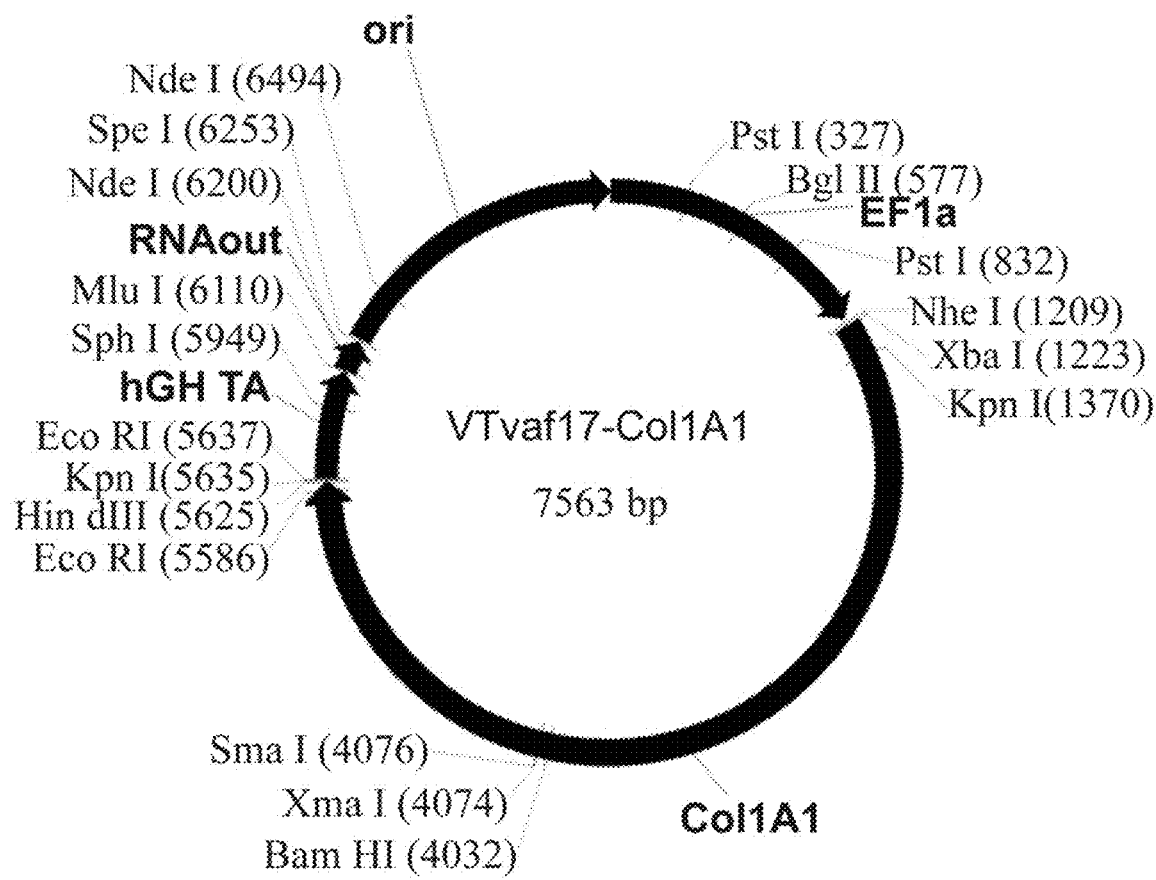
FIGS. 1A-1D show the structure of gene therapy DNA vector VTvaf17 carrying cDNA of the therapeutic human gene selected from the group of COL1A1, COL1A2, BMP2, and BMP7 genes that constitutes a circular double-stranded DNA molecule capable of autonomous replication in *Escherichia coli* cells.
Figure 1B:
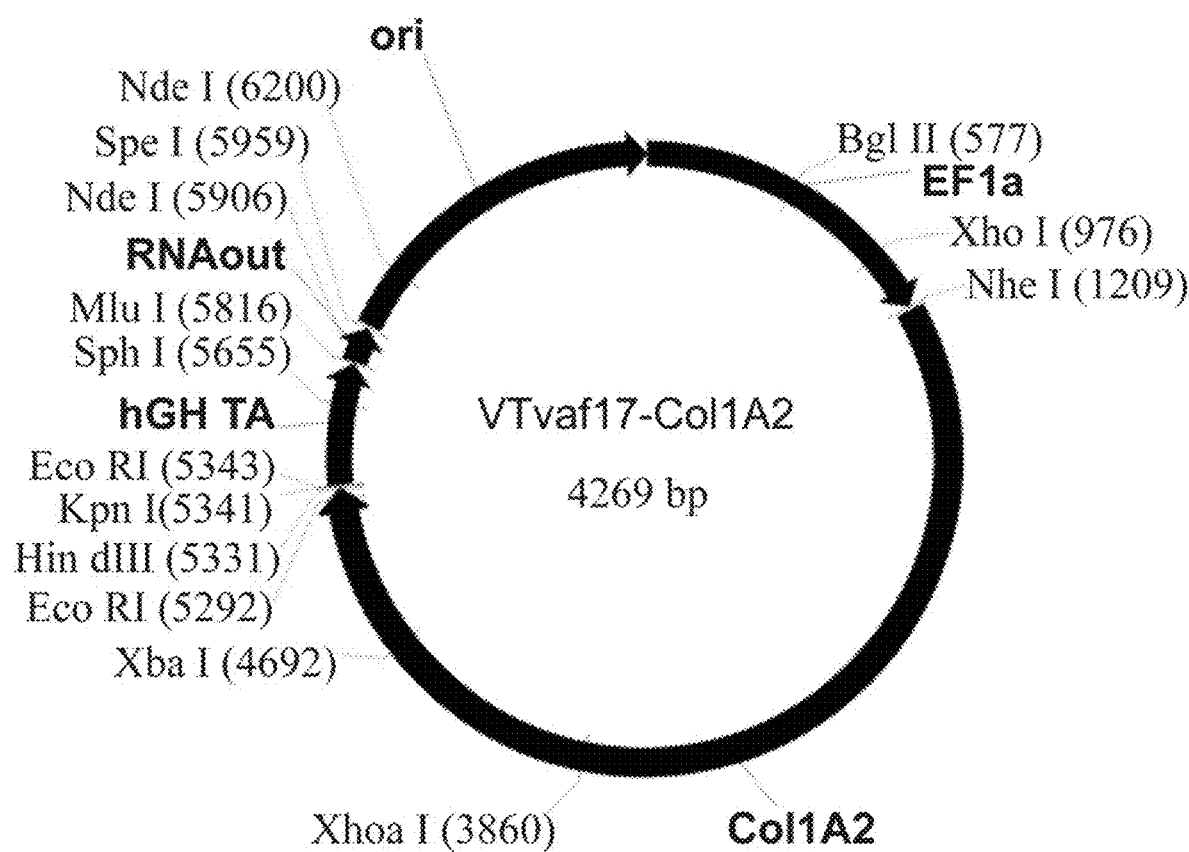
Figure 1C:
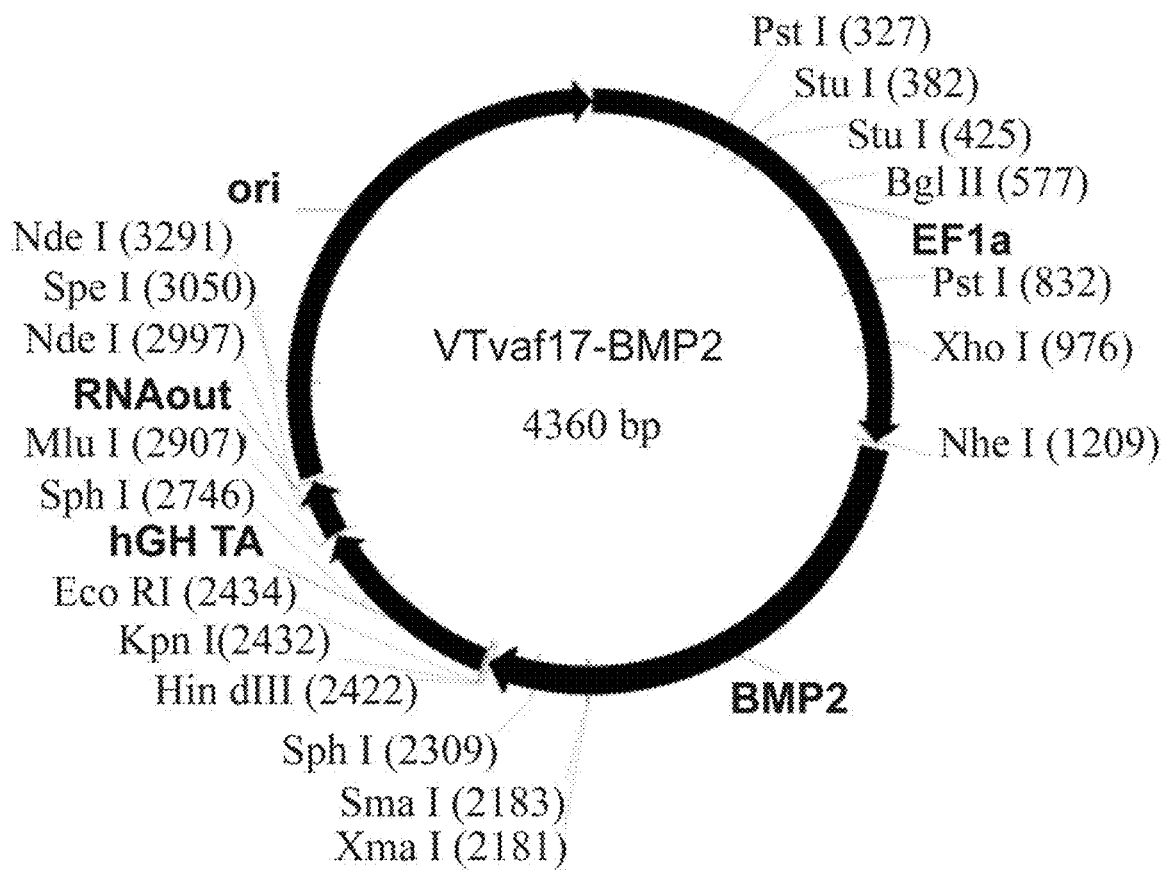
Figure 1D:
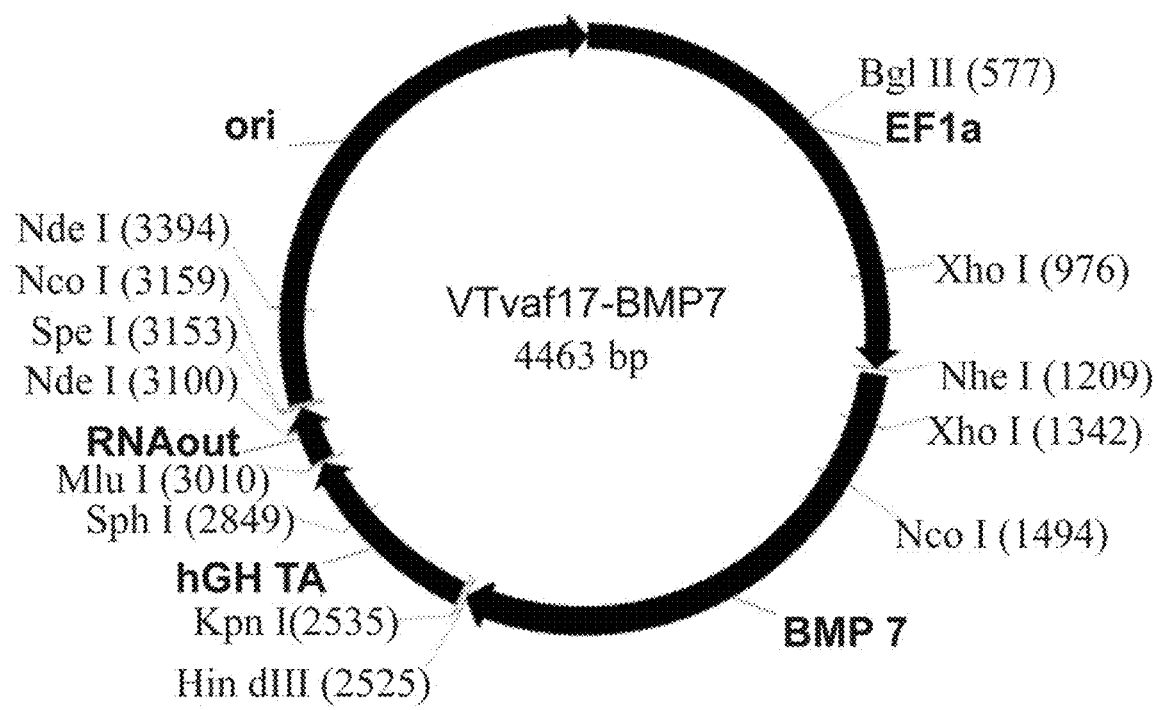

This resulted in DNA vector VTvaf17-COL1A1 containing nucleotide sequence SEQ ID NO: 1 carrying the therapeutic gene, namely a 4422 bp COL1A1 gene, allowing for antibiotic-free selection with the structure shown in FIG. 1A.

Gene therapy DNA vector VTvaf17 was constructed by consolidating six fragments of DNA derived from different sources:
- (a) the origin of replication (ori) was produced by PCR amplification of a region of commercially available plasmid pBR322 with a point mutation,
- (b) EF1a promoter region was produced by PCR amplification of a site of human genomic DNA,
- (c) hGH-TA transcription terminator was produced by PCR amplification of a site of human genomic DNA,
- (d) the RNA-OUT regulatory site of transposon Tn10 was synthesised from oligonucleotides
- (e) kanamycin resistance gene was produced by PCR amplification of a site of commercially available human plasmid pET-28,
- (f) the polylinker was produced by annealing two synthetic oligonucleotides.

PCR amplification was performed using the commercially available kit Phusion® High-Fidelity DNA Polymerase (New England Biolabs) as per the manufacturer's instructions. The fragments have overlapping regions allowing for their consolidation with subsequent PCR amplification. Fragments (a) and (b) were consolidated using oligonucleotides Ori-F and EF1-R, and fragments (c), (d), and (e) were consolidated using oligonucleotides hGH-F and Kan-R. Afterwards, the produced fragments were consolidated by restriction with subsequent ligation by sites BamHI and NcoI. This resulted in a plasmid still devoid of the polylinker. To add it, the plasmid was cleaved by BamHI and EcoRI sites followed by ligation with fragment (f). Therefore, a 3165 bp vector was constructed carrying the kanamycin resistance gene flanked by SpeI restriction sites. Then this gene was cleaved by SpeI restriction sites and the remaining fragment was ligated to itself. This resulted in a 3165 bp gene therapy DNA vector VTvaf17 that is recombinant and allows for antibiotic-free selection.

Example 2

```
COL1A2_F CCAGCTAGCGTCTAAGTGCTAGACATGCTC,

COL1A2_R CGAAGCTTTTATTTGAAACAGACTGGGCCA
``` and PCR amplification using the commercially available kit Phusion® High-Fidelity DNA Polymerase (New England Biolabs, USA) and constructed oligonucleotides

```
COL1A2_SF CTGGTGAAGCTGGTCGTGAT,

COL1A2_SR CGGATACAGGTTTCGCCAGT.
```

The amplification product of the coding region of COL1A1 gene and DNA vector VTvaf17 was cleaved by NheI and HindIII restriction endonucleases (New England Biolabs, USA).

This resulted in a 7269 bp DNA vector VTvaf17-COL1A2 containing nucleotide sequence SEQ ID NO: 2 carrying the therapeutic gene, namely a 4128 bp COL1A2 gene, allowing for antibiotic-free selection with the structure shown in FIG. 1.B.

Gene therapy DNA vector VTvaf17 was constructed as described in Example 1.

Example 3

Production of DNA vector VTvaf17-BMP2 carrying the human BMP2 therapeutic gene.

Gene therapy DNA vector VTvaf17-BMP2 was constructed by cloning the coding region of the BMP2 gene to the DNA vector VTvaf17 by NheI and HindIII restriction sites. The coding region of BMP2 gene (1219 bp) was obtained by isolating total RNA from the human tissue biopsy sample followed by reverse transcription reaction using commercial kit Mint-2 (Evrogen, Russia) and constructed oligonucleotides

```
BMP2_F ACAGCTAGCCTCCTAAAGGTCCACCATGGT,

BMP2_R TATAAGCTTCTAGCGACACCCACAACCCT
``` and PCR amplification was performed using the commercially available kit Phusion® High-Fidelity DNA Polymerase (New England Biolabs, USA) and constructed oligonucleotides

```
BMP2_SF ATGCAAGCAGGTGGGAAAGT,

BMP2_SR GGGAGCCACAATCCAGTCAT.
```

The amplification product of the coding region of COL1A1 gene and DNA vector VTvaf17 was cleaved by NheI and HindIII restriction endonucleases (New England Biolabs, USA).

This resulted in a 4360 bp gene therapy DNA vector VTvaf17-BMP2 containing nucleotide sequence SEQ ID NO: 3 carrying a 1219 bp BMP2 therapeutic gene allowing for antibiotic-free selection with the structure shown in FIG. 1.C.

Gene therapy DNA vector VTvaf17 was constructed as described in Example 1.

Example 4

Production of gene therapy DNA vector VTvaf17-BMP7 carrying the BMP7 therapeutic gene.

Gene therapy DNA vector VTvaf17-BMP7 was constructed by cloning the coding region of BMP7 gene to the DNA vector VTvaf17 by NheI and HindIII restriction sites. The coding region of BMP7 gene (1322 bp) was obtained by isolating total RNA from the human tissue biopsy sample followed by reverse transcription reaction using commercial kit Mint-2 (Evrogen, Russia) and constructed oligonucleotides

BMP7_F TCAGCTAGCGTAGAGCCGGCGCGATGCA,

BMP7_R TATAAGCTTCTAGTGGCAGCCACAGGC and PCR amplification was performed using the commercially available kit Phusion® High-Fidelity DNA Polymerase (New England Biolabs, USA) and constructed oligonucleotides

BMP7_SF GCTGGCTGGTGTTTGACATC,

BMP7_SR TGGTGGCGTTCATGTAGGAG, the amplification product of the coding region of COL1A1 gene and DNA vector VTvaf17 was cleaved by NheI and HindIII restriction endonucleases (New England Biolabs, USA).

This resulted in a 4463 bp DNA vector VTvaf17-BMP7 containing nucleotide sequence SEQ ID NO: 4 carrying the therapeutic gene, namely a 1322 bp BMP7 gene, allowing for antibiotic-free selection with the structure shown in FIG. 1.D.

Gene therapy DNA vector VTvaf17 was constructed as described in Example 1.

Example 5

Proof of the efficiency of gene therapy DNA vector VTvaf17-COL1A1 carrying COL1A1 therapeutic gene. This example also demonstrates practicability of use of gene therapy DNA vector carrying COL1A1 therapeutic gene.

To confirm the efficiency of gene therapy DNA vector VTvaf17-COL1A1, changes in mRNA accumulation of COL1A1 therapeutic gene in HDFa human primary dermal fibroblast cells (ATCC PCS-201-012) 48 hours after their transfection with gene therapy DNA vector VTvaf17-COL1A1 were assessed.

HDFa human primary dermal fibroblast cells were grown in Fibroblast Basal Medium (ATCC PCS-201-030) with the addition of components included in the Fibroblast Growth Kit-Serum-Free (ATCC PCS-201-040) at 37° C. in the presence of 5% CO2. To achieve 90% confluence, 24 hours before the transfection procedure, the cells were seeded into a 24-well plate in the quantity of $5 \times 10^4$ cells per well.

LIPOFECTAMINE 3000 (ThermoFisher Scientific, USA) was used as a transfection reagent. The transfection with gene therapy DNA vector VTvaf17-COL1A1 was performed as follows. In test tube 1, 1 µl of DNA vector VTvaf17-COL1A1 solution (concentration 500 ng/µl) and 1 µl of reagent P3000 was added to 25 µl of medium Opti-MEM (Gibco). The preparation was mixed by gentle shaking. In test tube 2, 1 µl of LIPOFECTAMINE 3000 solution was added to 25 µl of medium Opti-MEM (Gibco). The preparation was mixed by gentle shaking. The contents from test tube 1 were added to the contents of test tube 2, and the mixture was incubated at room temperature for 5 minutes. The resulting solution was added dropwise to the cells in the volume of 40 µl.

HDFa human primary dermal fibroblast cells transfected with the gene therapy DNA vector VTvaf17 devoid of the inserted therapeutic gene (cDNA of COL1A1 gene before and after transfection with gene therapy DNA vector VTvaf17 devoid of the inserted therapeutic gene is not shown in the figures to simplify visualisation) were used as a reference. Reference vector VTvaf17 for transfection was prepared as described above.

Extraction of total RNA from the transfected cells was performed as follows. 1 ml of TRIZOL Reagent (ThermoFisher Scientific) was added to the well with cells, homogenised and heated for 5 minutes at 65° C. The sample was centrifuged at 14,000 g for 10 minutes and heated again for 10 minutes at 65° C. Then 200 µl of chloroform was added, and the mixture was gently stirred and centrifuged at 14,000 g for 10 minutes. Then the water phase was isolated and mixed with $\frac{1}{10}$ of the volume of 3M sodium acetate, pH 5.2, and an equal volume of isopropyl alcohol. The sample was incubated at −20° C. for 10 minutes and then centrifuged at 14,000 g for 10 minutes. The precipitated RNA were rinsed in 1 ml of 70% ethyl alcohol, air-dried, and dissolved in 10 µl of RNase-free water. To measure the level of expression of COL1A1 gene mRNA after transfection, real-time PCR method (SYBR Green Real Time PCR) was used. For the amplification of human COL1A1-specific cDNA, COL1A1_SF and COL1A1_SR oligonucleotides were used according to the procedure described in Example 1. The length of amplification product is 756 bp. Beta-2 microglobulin (B2M) was used as a reference gene.

PCR amplification was performed using SYBR Green-QUANTITECT RT-PCR Kit (Qiagen, USA) in real-time in 20 µl of the amplification mixture containing: 25 µl of QUANTITECT SYBR Green RT-PCR Master Mix, 2.5 mM of magnesium chloride, 0.5 µM of each primer, and 5 µl of total RNA. For the reaction, CFX96 amplifier (Bio-Rad, USA) was used under the following conditions: 1 cycle of reverse transcription at 42° C. for 30 minutes, denaturation at 98° C. for 15 minutes followed by 40 cycles comprising denaturation at 94° C. for 15 s, annealing of primers at 60° C. for 30 s and elongation at 72° C. for 120 s. Positive control included amplicons from PCR on matrices represented by plasmids in known concentrations containing cDNA sequences of COL1A1 and B2M genes. Negative control included deionised water. Real-time quantification of the PCR products, i.e. COL1A1 and B2M gene cDNAs obtained by amplification, was conducted using the Bio-Rad CFX Manager 2.1 software.

To confirm increased expression of the COL1A1 gene in HDFa human primary dermal fibroblast cells after transfection of these cells with gene therapy DNA vector VTvaf17-COL1A1, FIG. 2 shows diagrams of accumulation of PCR products that indicate that due to the transfection of HDFa human primary dermal fibroblast cells with gene therapy DNA vector VTvaf17-COL1A1, the level of specific mRNA of the human COL1A1 gene has grown massively. This demonstrates the efficiency of gene therapy DNA vector VTvaf17-COL1A1. The presented results also confirm the practicability of use of gene therapy DNA vector VTvaf17-

COL1A1 in order to increase the expression level of COL1A1 gene in eukaryotic cells.

Example 6

Proof of the efficiency of gene therapy DNA vector VTvaf17-COL1A2 carrying COL1A2 therapeutic gene. This example also demonstrates practicability of use of gene therapy DNA vector carrying COL1A2 therapeutic gene.

To confirm the efficiency of gene therapy DNA vector VTvaf17-COL1A2 carrying the COL1A2 therapeutic gene, changes in mRNA accumulation of the COL1A2 therapeutic gene in human dermal fibroblasts 48 hours after their transfection with gene therapy DNA vector VTvaf17-COL1A2 were assessed.

Human dermal fibroblast culture was grown as follows. A biopsy specimen was taken behind the lobe of the patient's ear using DERMO PUNCH skin biopsy device (Medax, USA). The skin of patient in the biopsy site was preliminarily disinfected with 70% ethanol solution, rinsed with sterile saline, and anaesthetised with a lidocaine solution. The biopsy sample size was ca. 10 mm3, and the weight was approximately 11 mg. The sample was placed in a buffer solution containing 0.05% trypsin (Gibco) and 10 mM of EDTA. Cells were incubated with stirring in the magnetic stirrer at 37° C. Then the cell suspension was filtered using 100 μm pore size filters (Nalgen, USA), centrifuged for 10 minutes 130 g, the precipitated cells were re-suspended in 15 ml of Fibroblast Basal Medium (ATCC PCS-201-030) with the addition of components included in the Fibroblast Growth Kit—Serum-Free (ATCC PCS-201-040), placed in 75 cm$^2$ flask (Eppendorf), and incubated for 36-72 hours at 37° C. in the presence of 5% $CO_2$. To achieve 90% confluence, 24 hours before the transfection procedure, the cells were seeded into a 24-well plate in the quantity of $4 \times 10^4$ cells per well in the medium of the same composition. LIPOFECTAMINE 3000 (ThermoFisher Scientific, USA) was used as a transfection reagent. The transfection with gene therapy DNA vector VTvaf17-COL1A2 expressing the human COL1A2 gene was performed according to the procedure described in Example 5. The same cells transfected with the gene therapy DNA vector VTvaf17 (cDNA of COL1A2 gene before and after transfection with gene therapy DNA vector VTvaf17 devoid of the inserted therapeutic gene is not shown in the figures to simplify visualisation) were used as a reference. Extraction of total RNA from the transfected cells and synthesis of the first cDNA strand was performed according to the procedure described in Example 5. To measure the level of expression of COL1A2 gene mRNA after transfection, real-time PCR method (SYBR Green Real Time PCR) was used. For the amplification of COL1A2-specific cDNA, COL1A2_SF and COL1A2_SR oligonucleotides were used according to the procedure described in Example 2. The length of amplification product is 853 bp. Beta-2 microglobulin (B2M) was used as a reference gene.

PCR amplification was performed using SYBR Green-QUANTITECT RT-PCR Kit (Qiagen, USA) in real-time in 20 μl of the amplification mixture containing: 25 μl of QUANTITECT SYBR Green RT-PCR Master Mix, 2.5 mM of magnesium chloride, 0.5 μM of each primer, and 5 μl of total RNA. For the reaction, CFX96 amplifier (Bio-Rad, USA) was used under the following conditions: 1 cycle of reverse transcription at 42° C. for 30 minutes, denaturation at 98° C. for 15 minutes followed by 40 cycles comprising denaturation at 94° C. for 15 s, annealing of primers at 60° C. for 30 s and elongation at 72° C. for 120 s. Positive control included amplicons from PCR on matrices represented by plasmids in known concentrations containing cDNA sequences of COL1A2 and B2M genes. Negative control included deionised water. Real-time quantification of the PCR products, i.e. COL1A2 and B2M gene cDNAs obtained by amplification, was conducted using the Bio-Rad CFX Manager 2.1 software.

To confirm increased expression of the COL1A2 gene in human dermal fibroblast culture after transfection of these cells with gene therapy DNA vector VTvaf17-COL1A2, FIG. 3 shows diagrams of accumulation of PCR products that indicate that due to the transfection of human dermal fibroblast cells with gene therapy DNA vector VTvaf17-COL1A2 carrying the human COL1A2 therapeutic gene, the level of specific mRNA of COL1A2 human gene has grown massively. This demonstrates the efficiency of gene therapy DNA vector VTvaf17-COL1A2. The presented results also confirm the practicability of use of gene therapy DNA vector VTvaf17-COL1A2 in order to increase the expression level of COL1A2 gene in eukaryotic cells.

Example 7

Proof of the efficiency of gene therapy DNA vector VTvaf17-BMP2 carrying BMP2 therapeutic gene. This example also demonstrates practicability of use of gene therapy DNA vector carrying BMP2 therapeutic gene.

To confirm the efficiency of gene therapy DNA vector VTvaf17-BMP2 carrying BMP2 therapeutic gene, changes in mRNA accumulation of BMP2 therapeutic gene in MG-63 human osteosarcoma cells (ATCC CRL-1427) 48 hours after their transfection with gene therapy DNA vector VTvaf17-BMP2 were assessed.

MG-63 human osteosarcoma cells were cultured in DMEM (Gibco) medium with the addition of 10% fetal bovine serum (Gibco) and 10 μg/ml of gentamicin at 37° C. in the presence of 5% CO2. To achieve 90% confluence, 24 hours before the transfection procedure, the cells were seeded into a 24-well plate in the quantity of $5 \times 10^4$ cells per well. LIPOFECTAMINE 3000 (ThermoFisher Scientific, USA) was used as a transfection reagent. The transfection with gene therapy DNA vector VTvaf17-BMP2 expressing the human BMP2 gene was performed according to the procedure described in Example 5. MG-63 human osteosarcoma cells transfected with the gene therapy DNA vector VTvaf17 (cDNA of BMP2 gene before and after transfection with gene therapy DNA vector VTvaf17 devoid of the inserted therapeutic gene is not shown in the figures to simplify visualisation) were used as a reference. Extraction of total RNA from the transfected cells and synthesis of the first cDNA strand was performed according to the procedure described in Example 5. To measure the mRNA expression level of BMP2 gene after transfection, real-time PCR method (SYBR Green Real Time PCR) was used. For the amplification of human BMP2-specific cDNA, BMP2_SF and BMP2_SR oligonucleotides were used according to the procedure described in Example 3. The length of amplification product is 353 bp. Beta-2 microglobulin (B2M) was used as a reference gene.

PCR amplification was performed using SYBR Green-QUANTITECT RT-PCR Kit (Qiagen, USA) in real-time in 20 μl of the amplification mixture containing: 25 μl of QUANTITECT SYBR Green RT-PCR Master Mix, 2.5 mM of magnesium chloride, 0.5 μM of each primer, and 5 μl of total RNA. For the reaction, CFX96 amplifier (Bio-Rad, USA) was used under the following conditions: 1 cycle of reverse transcription at 42° C. for 30 minutes, denaturation at 98° C. for 15 minutes followed by 40 cycles comprising denaturation at 94° C. for 15 s, annealing of primers at 60° C. for 30 s and elongation at 72° C. for 30 s. Positive control included amplicons from PCR on matrices represented by plasmids in known concentrations containing cDNA sequences of BMP2 and B2M genes. Negative control included deionised water. Real-time quantification of the PCR products, i.e. BMP2 and B2M gene cDNAs obtained by amplification, was conducted using the Bio-Rad CFX Manager 2.1 software.

To confirm increased expression of the BMP2 gene in MG-63 human osteosarcoma cells after transfection of these cells with gene therapy DNA vector VTvaf17-BMP2, FIG. 4 shows diagrams of PCR products accumulation that indicate that due to the transfection of MG-63 human osteosarcoma cells with gene therapy DNA vector VTvaf17-BMP2 carrying the human BMP2 therapeutic gene, the level of specific mRNA of the human BMP2 gene has grown massively. This demonstrates the efficiency of gene therapy DNA vector VTvaf17-BMP2. The presented results also confirm the practicability of use of gene therapy DNA vector VTvaf17-BMP2 in order to increase the expression level of BMP2 gene in eukaryotic cells.

Example 8

Proof of the efficiency of gene therapy DNA vector VTvaf17-BMP7 carrying the therapeutic gene. This example also demonstrates practicability of use of gene therapy DNA vector carrying the BMP7 therapeutic gene.

To confirm the efficiency of gene therapy DNA vector VTvaf17-BMP7, changes in mRNA accumulation of the BMP7 therapeutic gene in primary culture of hFOB 1.19 human osteoblast cells (ATCC CRL-11372) 48 hours after their transfection with gene therapy DNA vector VTvaf17-BMP7 were assessed.

The hFOB 1.19 primary human osteoblast cell line is grown in a mixture of F12 (Gibco, USA) and DMEM (Gibco, USA) (1:1) media containing 2 mM of L-glutamine, 0.3 mg/ml of G418 and 10% fetal bovine serum (Gibco, USA) at 37° C. in the presence of 5% CO2. To achieve 90% confluence, 24 hours before the transfection procedure, the cells were seeded into a 24-well plate in the quantity of $5 \times 10^4$ cells per well.

LIPOFECTAMINE 3000 (ThermoFisher Scientific, USA) was used as a transfection reagent. The transfection with gene therapy DNA vector VTvaf17-BMP7 expressing the human BMP7 gene was performed according to the procedure described in Example 5. hFOB 1.19 human osteoblast cells transfected with the gene therapy DNA vector VTvaf17 (cDNA of BMP7 gene before and after transfection with gene therapy DNA vector VTvaf17 devoid of the inserted therapeutic gene is not shown in the figures to simplify visualisation) were used as a reference. Extraction of total RNA from the transfected cells and synthesis of the first cDNA strand was performed according to the procedure described in Example 5. To measure the mRNA expression level of BMP7 gene after transfection, real-time PCR method (SYBR Green Real Time PCR) was used. For the amplification of human BMP7-specific cDNA, BMP7_SF and BMP7_SR oligonucleotides were used according to the procedure described in Example 4. The length of amplification product is 459 bp. Beta-2 microglobulin (B2M) was used as a reference gene.

PCR amplification was performed using SYBR Green-QUANTITECT RT-PCR Kit (Qiagen, USA) in real-time in 20 μl of the amplification mixture containing: 25 μl of QUANTITECT SYBR Green RT-PCR Master Mix, 2.5 mM of magnesium chloride, 0.5 μM of each primer, and 5 μl of total RNA. For the reaction, CFX96 amplifier (Bio-Rad, USA) was used under the following conditions: 1 cycle of reverse transcription at 42° C. for 30 minutes, denaturation at 98° C. for 15 minutes followed by 40 cycles comprising denaturation at 94° C. for 15 s, annealing of primers at 60° C. for 30 s and elongation at 72° C. for 30 s. Positive control included amplicons from PCR on matrices represented by plasmids in known concentrations containing cDNA sequences of BMP7 and B2M genes. Negative control included deionised water. Real-time quantification of the PCR products, i.e. BMP7 and B2M gene cDNAs obtained by amplification, was conducted using the Bio-Rad CFX Manager 2.1 software.

To confirm increased expression of the BMP7 gene in hFOB 1.19 human osteoblast cells after transfection of these cells with gene therapy DNA vector VTvaf17-BMP7 carrying the BMP7 therapeutic gene, FIG. 5 shows diagrams of accumulation of PCR products that indicate that due to the transfection of primary culture of hFOB 1.19 human osteoblast cells with gene therapy DNA vector VTvaf17-BMP7 carrying the human BMP7 therapeutic gene, the level of specific mRNA of BMP7 human gene has grown massively. This demonstrates the efficiency of gene therapy DNA vector VTvaf17-BMP7 and practicability of its use. The presented results also confirm the practicability of use of gene therapy DNA vector VTvaf17-BMP7 in order to increase the expression level of BMP7 gene in eukaryotic cells.

Example 9

Proof of the efficiency of gene therapy DNA vector VTvaf17-COL1A1 carrying the therapeutic gene, namely the COL1A1 gene, and practicability of its use.

To confirm the efficiency of gene therapy DNA vector VTvaf17-COL1A1 carrying the therapeutic gene, namely the COL1A1 gene, and practicability of its use, changes in protein concentration of type I collagen alpha 1 chain in cell culture medium of HDFa human primary dermal fibroblast cells (ATCC PCS-201-012) were assessed after transfection of these cells with gene therapy DNA vector VTvaf17-COL1A1 carrying the human COL1A1 gene.

HDFa human primary dermal fibroblast cells grown as described in Example 5 were used to assess changes in protein concentration of type I collagen alpha 1 chain.

Dendrimers of the 6th generation SUPERFECT Transfection Reagent (Qiagen, Germany) were used as transport molecule, aqueous dendrimer solution without DNA vector (A) and DNA vector VTvaf17 devoid of cDNA of the COL1A1 gene (B) as a reference, and DNA vector VTvaf17-COL1A1 carrying a region of the human COL1A1 gene SEQ ID NO: 1 (C) as transfected agents. The DNA-dendrimer complex was prepared according to the manufacturer's procedure (QIAGEN, SUPERFECT Transfection Reagent Handbook, 2002) with some modifications. For cell transfection in one well of a 24-well plate, antibiotic-free DMEM medium was added to 1 μg of DNA vector dissolved in TE buffer to a final volume of 60 μl, then 5 μl of SUPERFECT Transfection Reagent was added and gently mixed by pipetting five times. The complex was incubated at room temperature for 10-15 minutes. Then the culture medium was taken from the wells, the wells were rinsed with 1 ml of PBS buffer. 350 μl of DMEM complete medium containing 10 μg/ml of gentamicin was added to the resulting complex, mixed gently, and added to the cells. The cells were incubated with the complexes for 2-3 hours at 37° C. in the presence of 5% CO2.

The medium was then removed carefully, and the live cell array was rinsed with 1 ml of PBS buffer. Then, DMEM complete medium containing 10 μg/ml of gentamicin was added and incubated for 24-48 hours at 37° C. in the presence of 5% CO2.

After transfection, 0.1 ml of 1N HCl were added to 0.5 ml of the culture broth, mixed thoroughly, and incubated for 10 minutes at room temperature. Then, the mixture was neutralised by adding 0.1 ml of 1.2N NaOH/0.5M HEPES (pH 7-7.6) and stirred thoroughly. Supernatant was collected and used to assay the therapeutic protein. The COL1A1 protein was assayed by enzyme-linked immunosorbent assay (ELISA) using the Human collagen, type I, alpha 1 (COL1A1) ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of the type I collagen alpha 1 chain protein was used. R-3.0.2 was used for the statistical treatment of the results and data visualization (www.r-project.org/).

The diagram resulting from the assay is presented in FIG. 6 that indicates that the transfection of HDFa human primary dermal fibroblast cells with gene therapy DNA vector VTvaf17-COL1A1 carrying the COL1A1 gene results in an increase of type I collagen alpha 1 chain protein concentration compared to reference samples, which indicates the efficiency of gene therapy DNA vector VTvaf17-COL1A1 and confirms the ability of the vector to penetrate eukaryotic cells and express the COL1A1 gene at the protein level. The presented results also confirm the practicability of use of gene therapy DNA vector VTvaf17-COL1A1 in order to increase the expression level of the COL1A1 gene in eukaryotic cells.

Example 10

Proof of the efficiency of gene therapy DNA vector VTvaf17-COL1A2 carrying the therapeutic gene, namely the COL1A2 gene, and practicability of its use.

To confirm the efficiency of gene therapy DNA vector VTvaf17-COL1A2 carrying the therapeutic gene, namely the COL1A2 gene, and practicability of its use, changes in protein concentration of type I collagen alpha 2 chain in the cell culture medium of human dermal fibroblast cells were assessed after transfection of these cells with gene therapy DNA vector VTvaf17-COL1A2 carrying the human COL1A2 gene.

HDFa human primary dermal fibroblast cells were grown as described in Example 6 to assess changes in protein concentration of type I collagen alpha 2 chain. Dendrimers of the 6th generation SUPERFECT Transfection Reagent (Qiagen, Germany) were used as transport molecule, aqueous dendrimer solution without DNA vector (A) and DNA vector VTvaf17 devoid of cDNA of the COL1A2 gene (B) as a reference, and DNA vector VTvaf17-COL1A2 carrying a region of the human COL1A2 gene SEQ ID NO: 2 (C) as transfected agents. Preparation of the DNA dendrimer complex and transfection of human dermal fibroblast cells were performed according to the procedure described in Example 9.

After transfection, cells were rinsed three times with PBS, and then 1 ml of PBS was added to the cells and the cells were subjected to freezing/thawing three times. Then the suspension was centrifuged for 15 minutes at 15,000 rpm, and supernatant was collected and used for the quantification and assay of the therapeutic protein.

The COL1A2 gene product was assayed by enzyme-linked immunosorbent assay (ELISA) using the Human Collagen, Type I Alpha 2 (COL1A2) ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of the type I collagen alpha 2 chain protein was used.

R-3.0.2 was used for the statistical treatment of the results and data visualization (www.r-project.org/).

The diagram resulting from the assay is presented in FIG. 7 that indicates that the transfection of human fibroblast cells with gene therapy DNA vector VTvaf17-COL1A2 carrying the COL1A2 gene results in an increase of type I collagen alpha 2 chain protein concentration compared to reference samples, which indicates the efficiency of gene therapy DNA vector VTvaf17-COL1A2 and confirms the ability of the vector to penetrate eukaryotic cells and express the COL1A2 gene at the protein level. The presented results also confirm the practicability of use of gene therapy DNA vector VTvaf17-COL1A2 in order to increase the expression level of COL1A2 in eukaryotic cells.

Example 11

Proof of the efficiency of gene therapy DNA vector VTvaf17-BMP2 carrying the therapeutic gene, namely the BMP2 gene, and practicability of its use.

To confirm the efficiency of gene therapy DNA vector VTvaf17-BMP2 carrying the BMP2 therapeutic gene and practicability of its use, changes in bone morphogenetic protein 2 concentration in the culture medium of MG-63 human osteosarcoma cells (ATCC CRL-1427) were assessed after transfection of these cells with gene therapy DNA vector VTvaf17-BMP2 carrying the human BMP2 gene.

MG-63 human osteosarcoma cells were grown as described in Example 7 to assess changes in bone morphogenetic protein 2 concentration. Dendrimers of the 6th generation SUPERFECT Transfection Reagent (Qiagen, Germany) were used as transport molecule, aqueous dendrimer solution without DNA vector (A) and DNA vector VTvaf17 devoid of cDNA of the BMP2 gene (B) as a reference, and DNA vector VTvaf17-BMP2 carrying the human BMP2 therapeutic gene SEQ ID NO: 3 (C) as transfected agents. The DNA-dendrimer complex was prepared and MG-63 human osteosarcoma cells were transfected according to the procedure described in Example 9.

After transfection, cells were rinsed three times with PBS, and then 1 ml of PBS was added to the cells and the cells were subjected to freezing/thawing three times. Then the suspension was centrifuged for 15 minutes at 15,000 rpm, and supernatant was collected and used for the quantification and assay of the therapeutic protein.

The BMP-2 gene product was assayed by enzyme-linked immunosorbent assay (ELISA) using the Human BMP-2, ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of bone morphogenetic protein 2 was used.

The diagram resulting from the assay is presented in FIG. 8 that indicates that the transfection of MG-63 human osteosarcoma cells with gene therapy DNA vector VTvaf17-BMP2 carrying the BMP2 gene results in an increase of bone morphogenetic protein 2 concentration compared to reference samples, which indicates the efficiency of gene therapy DNA vector VTvaf17-BMP2 and confirms the ability of the vector to penetrate eukaryotic cells and express the BMP2 gene at the protein level. The presented results also confirm the practicability of use of gene therapy DNA vector VTvaf17-BMP2 in order to increase the expression level of BMP2 in eukaryotic cells.

Example 12

Proof of the efficiency of gene therapy DNA vector VTvaf17-BMP7 carrying the therapeutic gene, namely the BMP7 gene, and practicability of its use.

To confirm the efficiency of gene therapy DNA vector VTvaf17-BMP7 carrying the BMP7 therapeutic gene and practicability of its use, changes in bone morphogenetic protein 7 concentration in the culture medium of hFOB 1.19 human osteoblast cells (ATCC CRL-11372) were assessed after transfection of these cells with gene therapy DNA vector VTvaf17-BMP7 carrying the human BMP7 gene.

hFOB 1.19 human osteoblast cells were grown as described in Example 8 to assess changes in bone morphogenetic protein 7 concentration. Dendrimers of the 6th generation SUPERFECT Transfection Reagent (Qiagen, Germany) were used as transport molecule, aqueous dendrimer solution without DNA vector (A) and DNA vector VTvaf17 devoid of cDNA of the BMP7 gene (B) as a reference, and DNA vector VTvaf17-BMP7 carrying the human BMP7 therapeutic gene SEQ ID NO: 4 (C) as transfected agents. The DNA-dendrimer complex was prepared and hFOB 1.19 human osteoblast cells were transfected according to the procedure described in Example 9.

After transfection, cells were rinsed three times with PBS, and then 1 ml of PBS was added to the cells and the cells were subjected to freezing/thawing three times. Then the suspension was centrifuged for 15 minutes at 15,000 rpm, and supernatant was collected and used for the quantification and assay of the therapeutic protein.

The BMP-7 gene product was assayed by enzyme-linked immunosorbent assay (ELISA) using the Human BMP-7, ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of bone morphogenetic protein 7 was used.

The diagram resulting from the assay is presented in FIG. 9 that indicates that the transfection of hFOB 1.19 human osteoblast cells with gene therapy DNA vector VTvaf17-BMP7 carrying the BMP7 gene results in an increase of bone morphogenetic protein 7 concentration compared to reference samples, which indicates the efficiency of gene therapy DNA vector VTvaf17-BMP7 and confirms the ability of the vector to penetrate eukaryotic cells and express the BMP7 gene at the protein level. The presented results also confirm the practicability of use of gene therapy DNA vector VTvaf17-BMP7 in order to increase the expression level of BMP7 in eukaryotic cells.

Example 13

Proof of the efficiency and practicability of use of gene therapy DNA vector VTvaf17-COL1A2 carrying the COL1A2 gene in order to increase the expression of COL1A2 protein in human tissues.

To analyse changes in the concentration of the type I collagen alpha 2 chain protein, gene therapy DNA vector VTvaf17-COL1A2 carrying the COL1A2 gene was injected into the forearm skin of three patients with concurrent injection of a placebo being gene therapy DNA vector VTvaf17 devoid of the COL1A2 gene.

Patient 1, man, 65 y.o. (P1); Patient 2, woman, 67 y.o. (P2); Patient 3, man, 62 y.o. (P3). Polyethyleneimine Transfection reagent cGMP grade in-vivo-jetPEI (Polyplus Transfection, France) was used as a transport system. Gene therapy DNA vector VTvaf17-COL1A2 containing the COL1A2 gene and gene therapy DNA vector VTvaf17 used as a placebo were dissolved in sterile nuclease-free water. DNA-cGMP grade in-vivo-jetPEI complexes were prepared according to the manufacturer recommendations.

Gene therapy DNA vector VTvaf17 (placebo) and gene therapy DNA vector VTvaf17-COL1A2 were injected in the quantity of 1 mg for each genetic construct using the tunnel method with a 30 G needle to the depth of 3 mm. The injectate volume of gene therapy DNA vector VTvaf17 (placebo) and gene therapy DNA vector VTvaf17-COL1A2 was 0.3 ml for each genetic construct. The points of injection of each genetic construct were located at 8 to 10 cm intervals at the forearm site.

The biopsy samples were taken on the 2nd day after the injection of the genetic constructs of gene therapy DNA vectors. The biopsy samples were taken from the patients' skin in the site of injection of gene therapy DNA vector VTvaf17-COL1A2 carrying the COL1A2 gene (I), gene therapy DNA vector VTvaf17 (placebo) (II), and from intact skin (III) using the skin biopsy device Epitheasy 3.5 (Medax SRL, Italy). The skin of patients in the biopsy site was preliminarily rinsed with sterile saline and anaesthetised with a lidocaine solution. The biopsy sample size was ca. 10 mm3, and the weight was approximately 11 mg. The sample was placed in a buffer solution containing 50 mM of Tris-HCl, pH 7.6, 100 mM of NaCl, 1 mM of EDTA, and 1 mM of phenylmethylsulfonyl fluoride, and homogenised to obtain a homogenised suspension. The suspension was then centrifuged for 10 minutes at 14,000 g. Supernatant was collected and used to assay the type I collagen alpha 2 chain therapeutic protein by enzyme-linked immunosorbent assay (ELISA) using the Human Collagen, Type I Alpha 2 (COL1A2) ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of the type I collagen alpha 2 chain protein was used. Diagrams resulting from the assay are shown in FIG. 10.

FIG. 10 shows that the concentration of collagen type I alpha 2 chain protein was increased in the skin of all three patients in the injection site of gene therapy DNA vector VTvaf17-COL1A2 carrying the human COL1A2 therapeutic gene compared to the concentration of type I collagen alpha 2 chain protein in the injection site of gene therapy DNA vector VTvaf17 (placebo) devoid of the human COL1A2 gene, which indicates the efficiency of gene therapy DNA vector VTvaf17-COL1A2 and confirms the practicability of its use, in particular upon injection of gene therapy DNA vector in human tissues/organs.

Example 14

Proof of the efficiency and practicability of use of gene therapy DNA vector VTvaf17-COL1A1 carrying the COL1A1 gene in order to increase the expression of COL1A1 protein in human tissues To analyse changes in the concentration of the type I collagen alpha 1 chain protein, gene therapy DNA vector VTvaf17-COL1A1 carrying the COL1A1 gene was injected into the cartilaginous tissue from backside of earflaps of three patients with concurrent injection of a placebo being gene therapy DNA vector VTvaf17 devoid of the COL1A1 gene.

Patient 1, man, 65 y.o. (P1); Patient 2, woman, 67 y.o. (P2); Patient 3, man, 62 y.o. (P3). Polyethyleneimine Transfection reagent cGMP grade in-vivo-jetPEI (Polyplus Transfection, France) was used as a transport system. Gene therapy DNA vector VTvaf17-COL1A1 containing the COL1A1 gene and gene therapy DNA vector VTvaf17 used as a placebo were dissolved in sterile nuclease-free water. DNA-cGMP grade in-vivo-jetPEI complexes were prepared according to the manufacturer recommendations.

Gene therapy DNA vector VTvaf17 (placebo) and gene therapy DNA vector VTvaf17-COL1A1 were injected into the cartilaginous tissue from backside of earflaps in the quantity of 1 mg for each genetic construct using the tunnel method with a 30 G needle to the depth of 1-2 mm. The injectate volume of gene therapy DNA vector VTvaf17 (placebo) and gene therapy DNA vector VTvaf17-COL1A1 was 0.2 ml for each genetic construct. The points of injection of the biologically active gene therapy substance and placebo were located at 2 to 3 cm intervals.

The biopsy samples were taken on the 3rd day after the injection of gene therapy DNA vectors. The biopsy samples were taken from the patients' skin in the site of injection of gene therapy DNA vector VTvaf17-COL1A1 carrying the COL1A1 gene (I), gene therapy DNA vector VTvaf17 (placebo) (II), and from intact skin (III) by percutaneous biopsy using a disposable manual biopsy needle, and then procedures were performed as described in Example 13.

The type I collagen alpha 1 chain protein level was assayed in the supernatants of patient cartilage biopsy specimens by enzyme-linked immunosorbent assay (ELISA) using the Human Collagen, Type I Alpha 1 (COL1A1) ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of the type I collagen alpha 1 chain protein was used. Diagrams resulting from the assay are shown in FIG. 11.

FIG. 11 shows that the concentration of collagen type I alpha 1 chain protein was increased in the cartilaginous tissue of all three patients in the site of injection of gene therapy DNA vector VTvaf17-COL1A1 carrying the human COL1A1 therapeutic gene compared to the concentration of type I collagen alpha 1 chain protein in the site of injection of gene therapy DNA vector VTvaf17 (placebo) devoid of the human COL1A1 gene, which indicates the efficiency of gene therapy DNA vector VTvaf17-COL1A1 and confirms the practicability of its use, in particular upon injection of gene therapy DNA vector in human cartilaginous tissue.

Example 15

Proof of the efficiency of gene therapy DNA vector VTvaf17-COL1A1 carrying the COL1A1 gene and practicability of its use in order to increase the expression level of the COL1A1 protein in human tissues by introducing autologous fibroblasts transfected with gene therapy DNA vector VTvaf17-COL1A1.

To confirm the efficiency of gene therapy DNA vector VTvaf17-COL1A1 carrying the COL1A1 gene and practicability of its use, changes in the COL1A1 protein level in human skin upon injection of patient's skin with autologous fibroblast culture of the same patient transfected with gene therapy DNA vector VTvaf17-COL1A1 were assessed.

The appropriate autologous fibroblast culture transfected with the gene therapy DNA vector VTvaf17-COL1A1 carrying the COL1A1 gene was injected into the patient's forearm skin with concurrent injection of a placebo in the form of autologous fibroblast culture transfected with gene therapy DNA vector VTvaf17 not carrying the COL1A1 gene.

The human primary fibroblast culture was isolated from the patient skin biopsy specimens. Biopsy specimens of the skin from the area protected by ultraviolet, namely behind the ear or on the inner lateral side of the elbow, were taken using the skin biopsy device Epitheasy 3.5 (Medax SRL, Italy). The biopsy sample was ca. 10 mm and ca. 11 mg. The patient's skin was preliminarily rinsed with sterile saline and anaesthetised with a lidocaine solution. The primary cell culture was cultivated at 37° C. in the presence of 5% CO2, in the DMEM medium with 10% fetal bovine serum and 100 U/ml of ampicillin. The passage and change of culture medium was performed every 2 days. Total duration of culture growth did not exceed 25-30 days. Then an aliquot of 5×104 cells was taken from the cell culture. The patient's fibroblast culture was transfected with the gene therapy DNA vector VTvaf17-COL1A1 carrying the COL1A1 gene or placebo, i.e. vector VTvaf17 not carrying the COL1A1 therapeutic gene.

The transfection was carried out using a cationic polymer such as polyethyleneimine JETPEI (Polyplus transfection, France), according to the manufacturer's instructions. The cells were cultured for 72 hours and then injected into the patient. Injection of autologous fibroblast culture of the patient transfected with gene therapy DNA vector VTvaf17-COL1A1, and autologous fibroblast culture of the patient non-transfected with gene therapy DNA vector VTvaf17 as a placebo was performed in the forearm using the tunnel method with a 13 mm long 30 G needle to the depth of approximately 3 mm. The concentration of the modified autologous fibroblasts in the introduced suspension was approximately 5 mln cells per 1 ml of the suspension, the dose of the injected cells did not exceed 15 mln. The points of injection of the autologous fibroblast culture were located at 8 to 10 cm intervals.

Biopsy specimens were taken on the 4th day after the injection of autologous fibroblast culture transfected with the gene therapy DNA vector VTvaf17-COL1A1 carrying the therapeutic gene, namely COL1A1 gene, and placebo. Biopsy was taken from the patient's skin in the site of injection of autologous fibroblast culture transfected with gene therapy DNA vector VTvaf17-COL1A1 carrying the COL1A1 therapeutic gene (C), autologous fibroblast culture non-transfected with gene therapy DNA vector VTvaf17 not carrying the COL1A1 therapeutic gene (placebo) (B), as well as from intact skin site (A) using the skin biopsy device Epitheasy 3.5 (Medax SRL, Italy), and then procedures were performed as described in Example 13.

The type I collagen alpha 1 chain protein level was assayed in the supernatants of patient's skin biopsy samples by enzyme-linked immunosorbent assay (ELISA) using the Human Collagen, Type I Alpha 1 (COL1A1) ELISA Kit (MyBioSource, USA) according to the manufacturer's method with optical density detection at 450 nm wavelength using CHEMWELL Automated EIA and Chemistry Analyser (Awareness Technology Inc., USA).

To measure the numerical value of concentration, the calibration curve constructed using the reference samples from the kit with known concentrations of the type I collagen alpha 1 chain protein was used. Diagrams resulting from the assay are shown in FIG. 12.

FIG. 12 shows an increase in the concentration of COL1A1 protein in the area of the patient's skin in the injection site of autologous fibroblast culture transfected with the gene therapy DNA vector VTvaf17-COL1A1 carrying the COL1A1 gene compared to the COL1A1 protein concentration in the injection site of autologous fibroblast culture transfected with the gene therapy DNA vector VTvaf17 that does not carry the COL1A1 gene (placebo), which indicates the efficiency of gene therapy DNA vector VTvaf17-COL1A1 and practicability of its use in order to increase the expression level of COL1A1 in human tissues/organs, in particular upon injection of autologous fibroblasts transfected with the gene therapy DNA vector VTvaf17-COL1A1 into the skin.

Example 16

Proof of the efficiency and practicability of combined use of gene therapy DNA vector VTvaf17-COL1A1 carrying the COL1A1 therapeutic gene, gene therapy DNA vector VTvaf17-COL1A2 carrying the COL1A2 therapeutic gene, gene therapy DNA vector VTvaf17-BMP2 carrying the BMP2 therapeutic gene, gene therapy DNA vector VTvaf17-BMP7 carrying the BMP7 therapeutic gene in order to increase the expression level of the COL1A1, COL1A2, BMP2, and BMP7 proteins in mammalian tissues.

To confirm the efficiency of gene therapy DNA vector VTvaf17-COL1A1 carrying the COL1A1 therapeutic gene, DNA vector VTvaf17-COL1A2 carrying the COL1A2 therapeutic gene, DNA vector VTvaf17-BMP2 carrying the BMP2 therapeutic gene, and DNA vector VTvaf17-BMP7 carrying the BMP7 therapeutic gene and practicability of use of these vectors, the change in the concentration of type I collagen alpha 1 chain protein, type I collagen alpha 2 chain protein, bone morphogenetic protein 2, and bone morphogenetic protein 7, respectively, in the previously surgically modelled injury site of Wistar Rat shin bone (males, 22-24 weeks old) was assessed.

3 groups, 11 animals each were formed.

All animals underwent surgery under anaesthesia for shin bone defect. In particular, a skin incision up to 3.0 cm long was made on the outer surface of the right lower leg. Then the muscles were opened allowing access to the shin bone. The osteotomy was performed manually using a 2 mm drill to the bone canal in the diaphyseal region. Then a defect about 10 mm deep was perforated towards the knee epiphysis using a steel mandrel—needle featuring a diameter of 1.6 mm. The defect was filled through PE-50 catheter using a Hamilton syringe:

in group 1—with a mixture of gene therapy DNA vectors VTvaf17-COL1A1, VTvaf17-COL1A2, VTvaf17-BMP2, and VTvaf17-BMP7 in a volume of 20 µl (50 µg), the solution was prepared from a DNA lyophilisate and saline mixture, in group 2—with crude calcium phosphate precipitate of gene therapy DNA vectors VTvaf17-COL1A1, VTvaf17-COL1A2, VTvaf17-BMP2, and VTvaf17-BMP7 in a volume of 20 µl. (50 µg), in group 3 (control)—saline in a volume of 20 µl.

After the shin bone defect modelling and the injection of tested DNA vectors and saline, the defect was sealed with box wax.

The biopsy samples were taken 72 hours after the injection of the mixture of gene therapy DNA vectors and placebo. Biopsy was taken after necropsy of animals from the injury sites in the area of injection of a mixture of four gene therapy DNA vectors carrying the therapeutic genes COL1A1, COL1A2, BMP2, and BMP7 (group 1), in the area of injection of crude calcium phosphate precipitate mixture of four gene therapy DNA vectors carrying the COL1A1, COL1A2, BMP2, and BMP7 therapeutic genes (group 2), in the area of injection of saline (group 3). Mass of each biopsy sample was about 20 mg. Then procedures were performed as described in Example 13.

The COL1A1, COL1A2, BMP2, and BMP7 gene products were assayed by enzyme-linked immunosorbent assay (ELISA) using the Human collagen, type I, alpha 1 (COL1A1) ELISA Kit (MyBioSource, USA), Human Collagen, Type I Alpha 2 (COL1A2) ELISA Kit (MyBioSource, USA), Human BMP-2, ELISA Kit (MyBioSource, USA), Human BMP-7, ELISA Kit (MyBioSource, USA). Preparation of test samples, measurement and processing of results were performed as described in Example 9, 10, 11, and 12.

Diagrams resulting from the assay are shown in FIGS. 13A and 13B that indicate that in the injured area of animals in the injection site of precipitate of the mixture of four gene therapy DNA vectors: VTvaf17-COL1A1 carrying the human COL1A1 therapeutic gene, VTvaf17-COL1A2 carrying the human COL1A2 therapeutic gene, VTvaf17-BMP2 carrying the human BMP2 therapeutic gene, and VTvaf17-BMP7 carrying the human BMP7 therapeutic gene in group 1 of animals, the concentrations of the following proteins: type I collagen alpha 1 chain protein, type I collagen alpha 2 chain protein, bone morphogenetic protein 2, and bone morphogenetic protein 7 has significantly increased compared to the concentrations of COL1A1 type I collagen alpha 1 chain protein, type I collagen alpha 2 chain protein, bone morphogenetic protein 2, and bone morphogenetic protein 7 in the control group 3. It was also demonstrated that in the injured area of animals in the injection site of the mixture of four gene therapy DNA vectors: VTvaf17-COL1A1 carrying the human COL1A1 therapeutic gene, VTvaf17-COL1A2 carrying the human COL1A2 therapeutic gene, VTvaf17-BMP2 carrying the human BMP2 therapeutic gene, and VTvaf17-BMP7 carrying the human BMP7 therapeutic gene in group 2 of animals, the concentrations of the following proteins: type I collagen alpha 1 chain protein, type I collagen alpha 2 chain protein, bone morphogenetic protein 2, and bone morphogenetic protein 7 has moderately increased, respectively, compared to the concentrations of COL1A1 type I collagen alpha 1 chain protein, type I collagen alpha 2 chain protein, bone morphogenetic protein 2, and bone morphogenetic protein 7 in the control group 3. The presented results confirm the practicability of use of gene therapy DNA vector VTvaf17-COL1A1 carrying the COL1A1 therapeutic gene, gene therapy DNA vector VTvaf17-COL1A2 carrying the COL1A2 therapeutic gene, gene therapy DNA vector VTvaf17-BMP2 carrying the BMP2 therapeutic gene, and gene therapy DNA vector VTvaf17-BMP7 carrying the BMP7 therapeutic gene in order to increase the expression level of COL1A1, COL1A2, BMP2, and BMP7 proteins in animal tissues, in particular upon injection of these gene therapy DNA vectors into the bone tissue of mammals, and demonstrate the efficiency of gene therapy DNA vector VTvaf17-COL1A1, gene therapy DNA vector VTvaf17-COL1A2, gene therapy DNA vector VTvaf17-BMP2, and gene therapy DNA vector VTvaf17-BMP7.

Example 17

Proof of the efficiency of gene therapy DNA vector VTvaf17-BMP2 carrying the BMP2 therapeutic gene and practicability of its use in order to increase the expression level of bone morphogenetic protein 2 in mammalian cells.

To confirm the efficiency of gene therapy DNA vector VTvaf17-BMP2 carrying the human BMP2 therapeutic gene, changes in mRNA accumulation of the BMP2 therapeutic gene in CnOb canine osteoblast cells (Cell Applications, Inc., USA) 48 hours after their transfection with gene therapy DNA vector VTvaf17-BMP2 were assessed.

Canine osteoblast cell line (CnOb) was grown according to the manufacturer's method (www.cellapplications.com/canine-osteoblasts-cnob). The transfection with gene therapy DNA vector VTvaf17-BMP2 carrying the human BMP2 therapeutic gene and the DNA vector VTvaf17 not carrying the human BMP2 gene (control) was performed as described in Example 8. Extraction of total RNA from the transfected cells and synthesis of the first cDNA strand was performed according to the procedure described in Example 5. To measure the expression level of mRNA of BMP2 gene after transfection, real-time PCR method (SYBR Green Real Time PCR) was used as described in Example 3. Canine actin gene (ACT) was used as a reference gene.

Positive control included amplicons from PCR on matrices represented by plasmids in known concentrations containing cDNA sequences of BMP2 and ACT genes. Negative control included deionised water. Real-time quantification of the PCR products, i.e. BMP2 and ACT gene cDNAs obtained by amplification, was conducted using the Bio-Rad CFX Manager 2.1 software (Bio-Rad, USA).

Diagrams of accumulation of PCR products resulting from the assay are presented in FIG. 14 and indicate that the level of the specific mRNA of BMP2 gene has grown massively as a result of transfection of CnOb canine osteoblasts with gene therapy DNA vector VTvaf17-BMP2 carrying the human BMP2 therapeutic gene, which indicates the efficiency of gene therapy DNA vector VTvaf17-BMP2. The presented results also confirm the practicability of use of gene therapy DNA vector VTvaf17-BMP2 in order to increase the expression level of BMP2 gene in mammalian cells.

Example 18

*Escherichia coli* strain SCS110-AF/VTvaf17-COL1A1, or *Escherichia coli* strain SCS110-AF/VTvaf17-COL1A2, or *Escherichia coli* strain SCS110-AF/VTvaf17-BMP2, or *Escherichia coli* strain SCS110-AF/VTvaf17-BMP7 carrying gene therapy DNA vector, method of production thereof.

The strain construction for the production of gene therapy DNA vector based on gene therapy DNA vector VTvaf17 carrying COL1A1, or COL1A2, or BMP2, or BMP7 therapeutic gene on an industrial scale: namely *Escherichia coli* strain SCS110-AF/VTvaf17-COL1A1, or *Escherichia coli* strain SCS110-AF/VTvaf17-COL1A2, or *Escherichia coli* strain SCS110-AF/VTvaf17-BMP2, or *Escherichia coli* strain SCS110-AF/VTvaf17-BMP7 carrying gene therapy DNA vector VTvaf17-COL1A1, or VTvaf17-COL1A2, or VTvaf17-BMP2, or VTvaf17-BMP7, respectively, for its production allowing for antibiotic-free selection involves making electrocompetent cells of *Escherichia coli* strain SCS110-AF and subjecting these cells to electroporation with gene therapy DNA vector VTvaf17-COL1A1, or DNA vector VTvaf17-COL1A2, or DNA vector VTvaf17-BMP2, or DNA vector VTvaf17-BMP7. After that, the cells were poured into agar plates (Petri dishes) with a selective medium containing yeastrel, peptone, 6% sucrose, and 10 µg/ml of chloramphenicol. At the same time, production of *Escherichia coli* strain SCS110-AF for the production of gene therapy DNA vector VTvaf17 or gene therapy DNA vectors based on it allowing for antibiotic-free positive selection involves constructing a 64 bp linear DNA fragment that contains regulatory element RNA-IN of transposon Tn10 allowing for antibiotic-free positive selection, a 1422 bp levansucrase gene sacB, the product of which ensures selection within a sucrose-containing medium, a 763 bp chloramphenicol resistance gene catR required for the selection of strain clones in which homologous recombination occurs, and two homologous sequences, 329 bp and 233 bp, ensuring homologous recombination in the region of gene recA concurrent with gene inactivation, and then the *Escherichia coli* cells are transformed by electroporation, and clones surviving in a medium containing 10 µg/ml of chloramphenicol are selected.

Example 19

A method of production of gene therapy DNA vector based on gene therapy DNA vector VTvaf17 carrying the therapeutic gene selected from the group of COL1A1, COL1A2, BMP2, and BMP7 genes on an industrial scale.

To confirm the producibility and constructability on an industrial scale of gene therapy DNA vector VTvaf17-COL1A1 (SEQ ID NO: 1), or VTvaf17-COL1A2 (SEQ ID NO: 2), or VTvaf17-BMP2 (SEQ ID NO: 3), or VTvaf17-BMP7 (SEQ ID NO: 4), each carrying the therapeutic gene, namely COL1A1, or COL1A2, or BMP2, or BMP7, large-scale fermentation of *Escherichia coli* strain SCS110-AF/VTvaf17-COL1A1 (registered at the Russian National Collection of Industrial Microorganisms under number B-13165, located in Russia, 142290, Moscow Region, Pushchino, pr. Nauki, 5, IBPM, deposited on May 11, 2018, and described as "cellular organisms; Bacteria; Proteobacteria; Gammaproteobacteria; Enterobacterales; Enterobacteriaceae; *Escherichia*; *Escherichia coli*", INTERNATIONAL DEPOSITARY AUTHORITY No. NCIMB 43033), or *Escherichia coli* strain SCS110-AF/VTvaf17-COL1A2 (registered at the Russian National Collection of Industrial Microorganisms (Address: Russia, 142290, Moscow Region, Pushchino, pr. Nauki, 5, IBPM) under number B-13164, located in Russia, 142290, Moscow Region, Pushchino, pr. Nauki, 5, IBPM, deposited on May 11, 2018, and described as "cellular organisms; Bacteria; Proteobacteria; Gammaproteobacteria; Enterobacterales; Enterobacteriaceae; *Escherichia*; *Escherichia coli*", INTERNATIONAL DEPOSITARY AUTHORITY No. NCIMB 43035), or

*Escherichia coli* strain SCS110-AF/VTvaf17-BMP2 (registered at the Russian National Collection of Industrial Microorganisms under number B-13167, located in Russia, 142290, Moscow Region, Pushchino, pr. Nauki, 5, IBPM, deposited on May 11, 2018, and described as "cellular organisms; Bacteria; Proteobacteria; Gammaproteobacteria; Enterobacterales; Enterobacteriaceae; *Escherichia; Escherichia coli*", INTERNATIONAL DEPOSITARY AUTHORITY No. NCIMB 43034), or *Escherichia coli* strain SCS110-AF/VTvaf17-BMP7 (registered at the Russian National Collection of Industrial Microorganisms under number B-13166, located in Russia, 142290, Moscow Region, Pushchino, pr. Nauki, 5, IBPM, deposited on May 11, 2018, and described as "cellular organisms; Bacteria; Proteobacteria; Gammaproteobacteria; Enterobacterales; Enterobacteriaceae; *Escherichia; Escherichia coli*", INTERNATIONAL DEPOSITARY AUTHORITY No. NCIMB 43036), each containing gene therapy DNA vector VTvaf17 carrying the therapeutic gene, namely COL1A1, or COL1A2, or BMP2, or BMP7, was performed. Each *Escherichia coli* strain SCS110-AF/VTvaf17-COL1A1, or *Escherichia coli* strain SCS110-AF/VTvaf17-COL1A2, or *Escherichia coli* strain SCS110-AF/VTvaf17-BMP2, or *Escherichia coli* strain SCS110-AF/VTvaf17-BMP7 was produced based on *Escherichia coli* strain SCS110-AF (Cell and Gene Therapy LLC, PIT Ltd) as described in Example 18 by electroporation of competent cells of this strain with the gene therapy DNA vector VTvaf17-COL1A1, or VTvaf17-COL1A2, or VTvaf17-BMP2, or VTvaf17-BMP7 carrying the therapeutic gene, namely COL1A1, or COL1A2, or BMP2, or BMP7 with further inoculation of transformed cells into agar plates (Petri dishes) with a selective medium containing yeastrel, peptone, and 6% sucrose, and selection of individual clones.

Fermentation of *Escherichia coli* strain SCS110-AF/VTvaf17-COL1A1 carrying gene therapy DNA vector VTvaf17-COL1A1 was performed in a 10l fermenter with subsequent extraction of gene therapy DNA vector VTvaf17-COL1A1.

For the fermentation of *Escherichia coli* strain SCS110-AF/VTvaf17-COL1A1, medium containing the following ingredients per 10l of volume was prepared: 100 g of tryptone, 50 g of yeastrel (Becton Dickinson), then the medium was diluted with water to 8800 ml and autoclaved at 121° C. for 20 minutes, and then 1200 ml of 50% (w/v) sucrose was added. After that, the seed culture of *Escherichia coli* strain SCS110-AF/VTvaf17-COL1A1 was inoculated into a culture flask in the volume of 100 ml. The culture was incubated in an incubator shaker for 16 hours at 30° C. The seed culture was transferred to the Techfors S bioreactor (Infors HT, Switzerland) and grown to a stationary phase. The process was controlled by measuring optical density of the culture at 600 nm. The cells were pelleted for 30 minutes at 5,000-10,000 g. Supernatant was removed, and the cell pellet was re-suspended in 10% (by volume) phosphate buffered saline. The cells were centrifuged again for 30 minutes at 5,000-10,000 g. Supernatant was removed, a solution of 20 mM TrisCl, 1 mM EDTA, 200 g/l sucrose, pH 8.0 was added to the cell pellet in the volume of 1000 ml, and the mixture was stirred thoroughly to a homogenised suspension. Then egg lysozyme solution was added to the final concentration of 100 µg/ml. The mixture was incubated for 20 minutes on ice while stirring gently. Then 2500 ml of 0.2M NaOH, 10 g/l sodium dodecyl sulphate (SDS) was added, the mixture was incubated for 10 minutes on ice while stirring gently, then 3500 ml of 3M sodium acetate, 2M acetic acid, pH 5-5.5 was added, and the mixture was incubated for 10 minutes on ice while stirring gently. The resulting sample was centrifuged for 20-30 minutes at 15,000 g or a greater value. The solution was decanted delicately, and residual precipitate was removed by passing through a coarse filter (filter paper). Then RNase A (Sigma) was added to the final concentration of 20 µg/ml, and the solution was incubated overnight for 16 hours at room temperature. The solution was then centrifuged for 20-30 minutes at 15,000 g and passed through a 0.45 µm membrane filter (Millipore). Then ultrafiltration was performed with a membrane of 100 kDa (Millipore) and the mixture was diluted to the initial volume with a buffer solution of 25 mM TrisCl, pH 7.0. This manipulation was performed three to four times. The solution was applied to the column with 250 ml of DEAE SEPHAROSE HP (GE, USA), equilibrated with 25 mM TrisCl, pH 7.0. After the application of the sample, the column was washed with three volumes of the same solution and then gene therapy DNA vector VTvaf17-COL1A1 was eluted using a linear gradient of 25 mM TrisCl, pH 7.0, to obtain a solution of 25 mM TrisCl, pH 7.0, 1M NaCl, five times the volume of the column. The elution process was controlled by measuring optical density of the run-off solution at 260 nm. Chromatographic fractions containing gene therapy DNA vector VTvaf17-COL1A1 were joined together and subjected to gel filtration using SUPERDEX 200 (GE, USA). The column was equilibrated with phosphate buffered saline. The elution process was controlled by measuring optical density of the run-off solution at 260 nm, and the fractions were analysed by agarose gel electrophoresis. The fractions containing gene therapy DNA vector VTvaf17-COL1A1 were joined together and stored at −20° C. To assess the process reproducibility, the indicated processing operations were repeated five times. All processing operations for *Escherichia coli* strain SCS110-AF/VTvaf17-COL1A2, or *Escherichia coli* strain SCS110-AF/VTvaf17-BMP2, or *Escherichia coli* strain SCS110-AF/VTvaf17-BMP7 were performed in a similar way.

The process reproducibility and quantitative characteristics of final product yield confirm the producibility and constructability of gene therapy DNA vector VTvaf17-COL1A1, or VTvaf17-COL1A2, or VTvaf17-BMP2, or VTvaf17-BMP7 on an industrial scale.

Therefore, the purpose of this invention, namely the construction of a gene therapy DNA vector carrying the therapeutic human genes based on gene therapy DNA vector VTvaf17 for the treatment of diseases associated with the need to increase the expression level of these therapeutic genes that would reasonably combine:

possibility of safe use in the gene therapy of human beings and animals due to the absence of antibiotic resistance genes in the gene therapy DNA vector, length that ensures efficient gene delivery to the target cell, presence of regulatory elements that ensure efficient expression of the therapeutic genes while not being represented by nucleotide sequences of viral genomes, producibility and constructability on an industrial scale, as well as the purpose of construction of strains carrying these gene therapy DNA vectors for the production of these gene therapy DNA vectors on an industrial scale has been achieved, which is supported by the following examples: for Item I—Example 1, 2, 3, 4, 5; for Item II—Examples 1, 2, 3, 4, 5, 6, 7, 8, 9, 10, 11, 12, 13, 14, 15, 16, 17; for Item III—Example 1, 2, 3, 4, 5, 6, 7, 8, 9, 10, 11, 12, 13, 14, 15, 16, 17; for Item IV—Example 18, 19.

List of Oligonucleotide Sequences

1. Oligonucleotide BMP2_F ACAGCTAGCCTCCTAAAGGTCCACCATGGT
2. Oligonucleotide BMP2_R TATAAGCTTCTAGCGACACCCACAACCCT
3. Oligonucleotide BMP2_SF ATGCAAGCAGGTGGGAAAGT
4. Oligonucleotide BMP2_SR GGGAGCCACAATCCAGTCAT
5. Oligonucleotide BMP7_F TCAGCTAGCGTAGAGCCGGCGCGATGCA
6. Oligonucleotide BMP7_R TATAAGCTTCTAGTGGCAGCCACAGGC
7. Oligonucleotide BMP7_SF GCTGGCTGGTGTTTGACATC
8. Oligonucleotide BMP7_SR TGGTGGCGTTCATGTAGGAG
9. Oligonucleotide COL1A1_F CCAGCTAGCGTCTAGGGTCTAGACATGTTC
10. Oligonucleotide COL1A1_R TATAAGCTTCTACAGGAAGCAGACAGGGCCAAC
11. Oligonucleotide COL1A1_SF TGACGAGACCAAGAACTGCC
12. Oligonucleotide COL1A1_SR GCACCATCATTTCCACGAGC
13. Oligonucleotide COL1A2_F CCAGCTAGCGTCTAAGTGCTAGACATGCTC
14. Oligonucleotide COL1A2_R CGAAGCTTTTATTTGAAACAGACTGGGCCA
15. Oligonucleotide COL1A2_SF CTGGTGAPkGCTGGTCGTGAT
16. Oligonucleotide COL1A2_SR CGGATACAGGTTTCGCCAGT List of Abbreviations VTvaf17-Gene therapy vector devoid of sequences of viral genomes and antibiotic resistance markers (vector therapeutic virus-antibiotic-free)

DNA-Deoxyribonucleic acid cDNA-Complementary deoxyribonucleic acid

RNA-Ribonucleic acid mRNA-Messenger ribonucleic acid bp-base pair

PCR-Polymerase chain reaction

RT-PCR-real-time PCR ml-millilitre, μl-microlitre mm3-cubic millimetre l-litre

μg-microgram mg-milligram g-gram

μM-micromol mM-millimol min-minute s-second rpm-rotations per minute nm-nanometre cm-centimetre

```
mW—milliwatt

RFU—Relative fluorescence unit

PBS—Phosphate buffered saline
```

List of Abbreviations

VTvaf17—Gene therapy vector devoid of sequences of viral genomes and antibiotic resistance markers (vector therapeutic virus-antibiotic-free)
DNA—Deoxyribonucleic acid
cDNA—Complementary deoxyribonucleic acid
RNA—Ribonucleic acid
mRNA—Messenger ribonucleic acid
bp—base pair
PCR—Polymerase chain reaction
RT-PCR—real-time PCR
ml—millilitre, µl—microlitre
mm3—cubic millimetre
l—litre
µg—microgram
mg—milligram
g—gram
µM—micromol
mM—millimol
min—minute
s—second
rpm—rotations per minute
nm—nanometre
cm—centimetre
mW—milliwatt
RFU—Relative fluorescence unit
PBS—Phosphate buffered saline

What is claimed is:

1. A DNA vector selected from the group consisting of (i) DNA vector VTvaf17-COL1A1 that has the nucleotide sequence of SEQ ID NO: 1; (ii) DNA vector VTvaf17-COL1A2 that has the nucleotide sequence of SEQ ID NO: 2; (iii) DNA vector VTvaf17-BMP2 that has the nucleotide sequence of SEQ ID NO: 3; and (iv) DNA vector VTvaf17-BMP7 that has the nucleotide sequence of SEQ ID NO: 4.

2. A gene therapy DNA vector selected from the group consisting of (i) DNA vector VTvaf17-BMP2 that has the nucleotide sequence of SEQ ID NO: 3, and (ii) DNA vector VTvaf17-BMP7 that has the nucleotide sequence of SEQ ID NO: 4.

3. A method of producing a DNA vector, comprising cloning a coding region of COL1A1, COL1A2, BMP2, or BMP7 into gene therapy DNA vector VTvaf17 to produce (i) DNA vector VTvaf17-COL1A1 that has the nucleotide sequence of SEQ ID NO: 1, (ii) DNA vector VTvaf17-COL1A2 that has the nucleotide sequence of SEQ ID NO: 2, (iii) DNA vector VTvaf17-BMP2 that has the nucleotide sequence of SEQ ID NO: 3, or (iv) DNA vector VTvaf17-BMP7 that has the nucleotide sequence of SEQ ID NO: 4, respectively.

4. A method of improving osteoinduction or bone formation in a patient, comprising:
(i) injecting, into a bone in need of osteoinduction or bone formation of the patient, autologous dermal fibroblasts transfected with VTvaf17-BMP2 that has the nucleotide sequence of SEQ ID NO: 3, and/or VTvaf17-BMP7 that has the nucleotide sequence of SEQ ID NO: 4; or
(ii) injecting, into a bone in need of osteoinduction or bone formation of the patient, VTvaf17-BMP2 that has the nucleotide sequence of SEQ ID NO: 3, and/or VTvaf17-BMP7 that has the nucleotide sequence of SEQ ID NO: 4.

5. An *Escherichia coli* strain selected from the group consisting of (i) SCS110-AF/VTvaf17-COL1A1, deposited at the Russian National Collection of Industrial Microorganisms (VKPM) as accession number B-13165, (ii) SCS110-AF/VTvaf17-COL1A2, deposited at the Russian National Collection of Industrial Microorganisms (VKPM) as accession number B-13164, (iii) SCS110-AF/VTvaf17-BMP2, deposited at the Russian National Collection of Industrial Microorganisms (VKPM) as accession number B-13167, and (iv) SCS110-AF/VTvaf17-BMP7, deposited at the Russian National Collection of Industrial Microorganisms (VKPM) as accession number B-13166.

* * * * *

```
                         SEQUENCE LISTING

<160> NUMBER OF SEQ ID NOS: 20

<210> SEQ ID NO 1
<211> LENGTH: 4360
<212> TYPE: DNA
<213> ORGANISM: Homo Sapiens

<400> SEQUENCE: 1
cgtgaggctc cggtgcccgt cagtgggcag agcgcacatc gcccacagtc cccgagaagt      60
tggggggagg ggtcggcaat tgaaccggtg cctagagaaa gtggcgcggg gtaaactggg     120
aaagtgatgt cgtgtactgg ctccgccttt ttcccgaggg tgggggagaa ccgtatataa     180
gtgcagtagt cgccgtgaac gttctttttc gcaacgggtt tgccgccaga acacaggtaa     240
gtgccgtgtg tggttcccgc gggcctggcc tctttacggg ttatggccct tgcgtgcctt     300
gaattacttc cacgccctg gctgcagtac gtgattcttg atcccgagct tcgggttgga      360
agtgggtggg agagttcgag gccttgcgct taaggagccc cttcgcctcg tgcttgagtt     420
gaggcctggc ttgggcgctg gggccgccgc gtgcgaatct ggtggcacct tcgcgcctgt     480
ctcgctgctt tcgataagtc tctagccatt taaaattttt gatgacctgc tgcgacgctt     540
tttttctggc aagatagtct tgtaaatgcg ggccaagatc tgcacactgg tatttcggtt     600
tttggggccg cgggcggcga cggggcccgt gcgtcccagc gcacatgttc ggcgaggcgg     660
ggcctgcgag cgcggccacc gagaatcgga cgggggtagt ctcaagctgg ccggcctgct     720
ctggtgcctg gcctcgcgcc gccgtgtatc gccccgccct gggcggcaag gctggcccgg     780
tcggcaccag ttgcgtgagc ggaaagatgg ccgcttcccg gccctgctgc agggagctca     840
aaatggagga cgcggcgctc gggagagcgg gcgggtgagt cacccacaca aaggaaaagg     900
gcctttccgt cctcagccgt cgcttcatgt gactccacgg agtaccgggc gccgtccagg     960
cacctcgatt agttctcgag cttttggagt acgtcgtctt taggttgggg ggagggggttt   1020 tatgcgatgg agtttcccca cactgagtgg gtggagactg aagttaggcc agcttggcac    1080
ttgatgtaat tctccttgga atttgccctt tttgagtttg gatcttggtt cattctcaag    1140
cctcagacag tggttcaaag ttttttttctt ccatttcagg tgtcgtgaaa actacccta    1200
```

```
aaagccagct agcctcctaa aggtccacca tggtggccgg gacccgctgt cttctagcgt   1260
tgctgcttcc ccaggtcctc ctgggcggcg cggctggcct cgttccggag ctgggccgca   1320
ggaagttcgc ggcggcgtcg tcgggccgcc cctcatccca gccctctgac gaggtcctga   1380
gcgagttcga gttgcggctg ctcagcatgt tcggcctgaa acagagaccc accccccagca   1440 gggacgccgt ggtgccccc tacatgctag acctgtatcg caggcactca ggtcagccgg     1500
gctcacccgc cccagaccac cggttggaga gggcagccag ccgagccaac actgtgcgca   1560
gcttccacca tgaagaatct ttggaagaac taccagaaac gagtgggaaa caacccgga    1620 gattcttctt taatttaagt tctatcccca cggaggagtt tatcacctca gcagagcttc   1680
aggttttccg agaacagatg caagatgctt taggaaacaa tagcagtttc catcaccgaa   1740
ttaatattta tgaaatcata aaacctgcaa cagccaactc gaaattcccc gtgaccagac   1800
ttttggacac caggttggtg aatcagaatg caagcaggtg ggaaagtttt gatgtcaccc   1860
ccgctgtgat gcggtggact gcacaggac acgccaacca tggattcgtg gtggaagtgg     1920
cccacttgga ggagaaacaa ggtgtctcca agagacatgt taggataagc aggtctttgc   1980
accaagatga acacagctgg tcacagataa ggccattgct agtaactttt ggccatgatg   2040
gaaaagggca tcctctccac aaaagagaaa aacgtcaagc caaacacaaa cagcggaaac   2100
gccttaagtc cagctgtaag agacacccctt tgtacgtgga cttcagtgac gtggggtgga    2160
atgactggat tgtggctccc ccggggtatc acgccttta ctgccacgga gaatgccctt    2220
ttcctctggc tgatcatctg aactccacta atcatgccat tgttcagacg ttggtcaact   2280
ctgttaactc taagattcct aaggcatgct gtgtcccgac agaactcagt gctatctcga   2340
tgctgtacct tgacgagaat gaaaaggttg tattaaagaa ctatcaggac atggttgtgg   2400
agggttgtgg gtgtcgctag aagcttggta ccgaattccc tgtgacccct ccccagtgcc   2460
tctcctggcc ctggaagttg ccactccagt gcccaccagc cttgtcctaa taaaattaag   2520
ttgcatcatt ttgtctgact aggtgtcctt ctataatatt atggggtgga gggggtggt    2580 atggagcaag gggcaagttg ggaagacaac ctgtagggcc tgcggggtct attgggaacc   2640
aagctggagt gcagtggcac aatcttggct cactgcaatc tccgcctcct gggttcaagc   2700
gattctcctg cctcagcctc ccgagttgtt gggattccag gcatgcatga ccaggctcag   2760 ctaattttg tttttttggt agagacgggg tttcaccata ttggccaggc tggtctccaa   2820
ctcctaatct caggtgatct acccaccttg gcctcccaaa ttgctgggat tacaggcgtg   2880
aaccactgct cccttccctg tccttacgcg tagaattggt aaagagagtc gtgtaaaata   2940
tcgagttcgc acatcttgtt gtctgattat tgattttgg cgaaaccatt tgatcatatg    3000
acaagatgtg tatctacctt aacttaatga ttttgataaa aatcattaac tagtccatgg   3060
ctgcctcgcg cgtttcggtg atgacggtga aaacctctga cacatgcagc tcccggagac   3120
ggtcacagct tgtctgtaag cggatgccgg gagcagacaa gcccgtcagg gcgcgtcagc   3180
gggtgttggc gggtgtcggg gcgcagccat gacccagtca cgtagcgata gcggagtgta   3240
tactggctta actatgcggc atcagagcag attgtactga gagtgcacca tatgcggtgt   3300
gaaataccgc acagatgcgt aaggagaaaa taccgcatca ggcgctcttc cgcttcctcg   3360
ctcactgact cgctgcgctc ggtcgttcgg ctgcggcgag cggtatcagc tcactcaaag   3420
gcggtaatac ggttatccac agaatcaggg gataacgcag gaaagaacat gtgagcaaaa   3480
ggccagcaaa aggccaggaa ccgtaaaaag gccgcgttgc tggcgttttt ccataggctc   3540
```

| | |
|---|---|
| cgcccccctg acgagcatca caaaaatcga cgctcaagtc agaggtggcg aaacccgaca | 3600 |
| ggactataaa gataccaggc gtttccccct ggaagctccc tcgtgcgctc tcctgttccg | 3660 |
| accctgccgc ttaccggata cctgtccgcc tttctccctt cgggaagcgt ggcgctttct | 3720 |
| catagctcac gctgtaggta tctcagttcg gtgtaggtcg ttcgctccaa gctgggctgt | 3780 |
| gtgcacgaac ccccgttca gcccgaccgc tgcgccttat ccggtaacta tcgtcttgag | 3840 |
| tccaacccgg taagacacga cttatcgcca ctggcagcag ccactggtaa caggattagc | 3900 |
| agagcgaggt atgtaggcgg tgctacagag ttcttgaagt ggtggcctaa ctacggctac | 3960 |
| actagaagaa cagtatttgg tatctgcgct ctgctgaagc cagttacctt cggaaaaaga | 4020 |
| gttggtagct cttgatccgg caaacaaacc accgctggta gcggtggttt ttttgtttgc | 4080 |
| aagcagcaga ttacgcgcag aaaaaaagga tctcaagaag atcctttgat cttttctacg | 4140 |
| gggtctgacg ctcagtggaa cgaaaactca cgttaaggga ttttggtcat gagattatca | 4200 |
| aaaaggatct tcacctagat ccttttaaat taaaaatgaa gttttaaatc aatctaaagt | 4260 |
| atatatgagt aaacttggtc tgacagttac caatgcttaa tcagtgaggc acctatctca | 4320 |
| gcgatctgtc tatttcgttc atccatagtt gcctgactcc | 4360 |

<210> SEQ ID NO 2
<211> LENGTH: 4463
<212> TYPE: DNA
<213> ORGANISM: Homo Sapiens

<400> SEQUENCE: 2

| | |
|---|---|
| cgtgaggctc cggtgcccgt cagtgggcag agcgcacatc gcccacagtc cccgagaagt | 60 |
| tgggggagg ggtcggcaat tgaaccggtg cctagagaaa gtggcgcggg gtaaactggg | 120 |
| aaagtgatgt cgtgtactgg ctccgccttt ttcccgaggg tggggagaa ccgtatataa | 180 |
| gtgcagtagt cgccgtgaac gttctttttc gcaacgggtt tgccgccaga acacaggtaa | 240 |
| gtgccgtgtg tggttcccgc gggcctggcc tctttacggg ttatggccct tgcgtgcctt | 300 |
| gaattacttc cacgcccctg gctgcagtac gtgattcttg atcccgagct cgggttgga | 360 |
| agtgggtggg agagttcgag gccttgcgct taaggagccc cttcgcctcg tgcttgagtt | 420 |
| gaggcctggc ttgggcgctg gggccgccgc gtgcgaatct ggtggcacct tcgcgcctgt | 480 |
| ctcgctgctt tcgataagtc tctagccatt taaaattttt gatgacctgc tgcgacgctt | 540 |
| tttttctggc aagatagtct tgtaaatgcg ggccaagatc tgcacactgg tatttcggtt | 600 |
| tttggggccg cgggcggcga cggggcccgt gcgtcccagc gcacatgttc ggcgaggcgg | 660 |
| ggcctgcgag cgcggccacc gagaatcgga cgggggtagt ctcaagctgg ccggcctgct | 720 |
| ctggtgcctg gcctcgcgcc gccgtgtatc gccccgccct gggcggcaag gctgcccgg | 780 |
| tcggcaccag ttgcgtgagc ggaaagatgg ccgcttcccg gccctgctgc agggagctca | 840 |
| aaatggagga gcggcgctc gggagagcgg gcgggtgagt cacccacaca aaggaaaagg | 900 |
| gccttccgt cctcagccgt cgcttcatgt gactccacgg agtaccgggc gccgtccagg | 960 |
| cacctcgatt agttctcgag cttttggagt acgtcgtctt taggttgggg ggaggggttt | 1020 |
| tatgcgatgg agtttcccca cactgagtgg gtggagactg aagttaggcc agcttggcac | 1080 |
| ttgatgtaat tctccttgga atttgccctt tttgagtttg gatcttggtt cattctcaag | 1140 |
| cctcagacag tggttcaaag tttttttcctt ccatttcagg tgtcgtgaaa actacccta | 1200 |
| aaagccagct agcgtagagc cggcgcgatg cacgtgcgct cactgcgagc tgcggcgccg | 1260 |
| cacagcttcg tggcgctctg ggcacccctg ttcctgctgc gctccgccct ggccgacttc | 1320 |

```
agcctggaca acgaggtgca ctcgagcttc atccaccggc gcctccgcag ccaggagcgg   1380
cgggagatgc agcgcgagat cctctccatt ttgggcttgc cccaccgccc gcgcccgcac   1440
ctccagggca agcacaactc ggcacccatg ttcatgctgg acctgtacaa cgccatggcg   1500
gtggaggagg gcggcgggcc cggcggccag ggcttctcct accectacaa ggccgtcttc   1560 agtacccagg gccccectct ggccagcctg caagatagcc atttcctcac cgacgccgac   1620
atggtcatga gcttcgtcaa cctcgtggaa catgacaagg aattcttcca cccacgctac   1680
caccatcgag agttccggtt tgatctttcc aagatcccag aaggggaagc tgtcacggca   1740
gccgaattcc ggatctacaa ggactacatc cgggaacgct cgacaatga gacgttccgg   1800 atcagcgttt atcaggtgct ccaggagcac ttgggcaggg aatcggatct cttcctgctc   1860
gacagccgta ccctctgggc ctcggaggag ggctggctgg tgtttgacat cacagccacc   1920
agcaaccact gggtggtcaa tccgcggcac aacctgggcc tgcagctctc ggtggagacg   1980
ctggatgggc agagcatcaa ccccaagttg gcgggcctga ttgggcggca cgggcccag   2040 aacaagcagc ccttcatggt ggctttcttc aaggccacgg aggtccactt ccgcagcatc   2100
cggtccacgg ggagcaaaca gcgcagccag aaccgctcca agacgcccaa gaaccaggaa   2160
gccctgcgga tggccaacgt ggcagagaac agcagcagcg accagaggca ggcctgtaag   2220
aagcacgagc tgtatgtcag cttccgagac ctgggctggc aggactggat catcgcgcct   2280
gaaggctacg ccgcctacta ctgtgagggg gagtgtgcct tccctctgaa ctcctacatg   2340
aacgccacca accacgccat cgtgcagacg ctggtccact tcatcaaccc ggaaacggtg   2400
cccaagccct gctgtgcgcc cacgcagctc aatgccatct ccgtcctcta cttcgatgac   2460
agctccaacg tcatcctgaa gaaatacaga aacatggtgg tccgggcctg tggctgccac   2520
tagaagcttg gtaccgaatt ccctgtgacc cctccccagt gcctctcctg gccctggaag   2580
ttgccactcc agtgcccacc agccttgtcc taataaaatt aagttgcatc attttgtctg   2640
actaggtgtc cttctataat attatggggt ggaggggggt ggtatggagc aaggggcaag   2700
ttgggaagac aacctgtagg gcctgcgggg tctattggga accaagctgg agtgcagtgg   2760
cacaatcttg gctcactgca atctccgcct cctgggttca agcgattctc ctgcctcagc   2820
ctcccgagtt gttgggattc caggcatgca tgaccaggct cagctaattt tgtttttttt   2880
ggtagagacg gggtttcacc atattggcca ggctggtctc caactcctaa tctcaggtga   2940
tctacccacc ttggcctccc aaattgctgg gattacaggc gtgaaccact gctcccttcc   3000
ctgtccttac gcgtagaatt ggtaaagaga gtcgtgtaaa atatcgagtt cgcacatctt   3060
gttgtctgat tattgatttt tggcgaaacc atttgatcat atgacaagat gtgtatctac   3120
cttaacttaa tgattttgat aaaaatcatt aactagtcca tggctgcctc gcgcgtttcg   3180
gtgatgacgg tgaaaacctc tgacacatgc agctcccgga gacggtcaca gcttgtctgt   3240
aagcggatgc cgggagcaga caagcccgtc agggcgcgtc agcgggtgtt ggcgggtgtc   3300
ggggcgcagc catgacccag tcacgtagcg atagcggagt gtatactggc ttaactatgc   3360
ggcatcagag cagattgtac tgagagtgca ccatatgcgg tgtgaaatac cgcacagatg   3420
cgtaaggaga aaataccgca tcaggcgctc ttccgcttcc tcgctcactg actcgctgcg   3480
ctcggtcgtt cggctgcggc gagcggtatc agctcactca aaggcggtaa tacggttatc   3540
cacagaatca ggggataacg caggaaagaa catgtgagca aaaggccagc aaaaggccag   3600
gaaccgtaaa aaggccgcgt tgctggcgtt tttccatagg ctccgccccc ctgacgagca   3660
```

| | |
|---|---|
| tcacaaaaat cgacgctcaa gtcagaggtg gcgaaacccg acaggactat aaagatacca | 3720 |
| ggcgttuccc cctggaagct ccctcgtgcg ctctcctgtt ccgaccctgc cgcttaccgg | 3780 |
| atacctgtcc gcctttctcc cttcgggaag cgtggcgctt tctcatagct cacgctgtag | 3840 |
| gtatctcagt tcggtgtagg tcgttcgctc caagctgggc tgtgtgcacg aaccccccgt | 3900 |
| tcagcccgac cgctgcgcct tatccggtaa ctatcgtctt gagtccaacc cggtaagaca | 3960 |
| cgacttatcg ccactggcag cagccactgg taacaggatt agcagagcga ggtatgtagg | 4020 |
| cggtgctaca gagttcttga agtggtggcc taactacggc tacactagaa gaacagtatt | 4080 |
| tggtatctgc gctctgctga agccagttac cttcggaaaa agagttggta gctcttgatc | 4140 |
| cggcaaacaa accaccgctg gtagcggtgg ttttttttgtt tgcaagcagc agattacgcg | 4200 |
| cagaaaaaaa ggatctcaag aagatccttt gatcttttct acggggtctg acgctcagtg | 4260 |
| gaacgaaaac tcacgttaag ggattttggt catgagatta tcaaaaagga tcttcaccta | 4320 |
| gatccttta aattaaaaat gaagttttaa atcaatctaa agtatatatg agtaaacttg | 4380 |
| gtctgacagt taccaatgct taatcagtga ggcacctatc tcagcgatct gtctatttcg | 4440 |
| ttcatccata gttgcctgac tcc | 4463 |

<210> SEQ ID NO 3
<211> LENGTH: 7563
<212> TYPE: DNA
<213> ORGANISM: Homo Sapiens

<400> SEQUENCE: 3

| | |
|---|---|
| cgtgaggctc cggtgcccgt cagtgggcag agcgcacatc gcccacagtc cccgagaagt | 60 |
| tgggggagg ggtcggcaat tgaaccggtg cctagagaaa gtggcgcggg gtaaactggg | 120 |
| aaagtgatgt cgtgtactgg ctccgccttt ttcccgaggg tgggggagaa ccgtatataa | 180 |
| gtgcagtagt cgccgtgaac gttctttttc gcaacgggtt tgccgccaga acacaggtaa | 240 |
| gtgccgtgtg tggttcccgc gggcctggcc tctttacggg ttatggccct tgcgtgcctt | 300 |
| gaattacttc cacgcccctg gctgcagtac gtgattcttg atcccgagct cgggttgga | 360 |
| agtgggtggg agagttcgag gccttgcgct taaggagccc cttcgcctcg tgcttgagtt | 420 |
| gaggcctggc ttgggcgctg gggccgccgc gtgcgaatct ggtggcacct tcgcgcctgt | 480 |
| ctcgctgctt tcgataagtc tctagccatt taaaattttt gatgacctgc tgcgacgctt | 540 |
| ttttctggc aagatagtct tgtaaatgcg ggccaagatc tgcacactgg tatttcggtt | 600 |
| tttgggccg cggcggcga cggggcccgt gcgtcccagc gcacatgttc ggcgaggcgg | 660 |
| ggcctgcgag cgcggccacc gagaatcgga cggggtagt ctcaagctgg ccggcctgct | 720 |
| ctggtgcctg gcctcgcgcc gccgtgtatc gccccgccct gggcggcaag gctgccccgg | 780 |
| tcggcaccag ttgcgtgagc ggaaagatgg ccgcttcccg gccctgctgc agggagctca | 840 |
| aaatggagga cgcggcgctc gggagagcgg cgggtgagt cacccacaca aaggaaaagg | 900 |
| gccttccgt cctcagccgt cgcttcatgt gactccacgg agtaccgggc gccgtccagg | 960 |
| cacctcgatt agttctcgag cttttggagt acgtcgtctt taggttgggg ggagggttt | 1020 |
| tatgcgatgt agtttcccca cactgagtgg gtggagactg aagttaggcc agcttggcac | 1080 |
| ttgatgtaat tctccttgga atttgccctt tttgagtttg gatcttggtt cattctcaag | 1140 |
| cctcagacag tggttcaaag ttttttttctt ccatttcagg tgtcgtgaaa actacccta | 1200 |
| aaagccagct agcgtctagg gtctagacat gttcagcttt gtggacctcc ggctcctgct | 1260 |
| cctcttagcg gccaccgccc tcctgacgca cggccaagag gaaggccaag tcgagggcca | 1320 |

```
agacgaagac atcccaccaa tcacctgcgt acagaacggc ctcaggtacc atgaccgaga    1380
cgtgtggaaa cccgagccct gccggatctg cgtctgcgac aacggcaagg tgttgtgcga    1440
tgacgtgatc tgtgacgaga ccaagaactg ccccggcgcc gaagtccccg agggcgagtg    1500
ctgtcccgtc tgccccgacg gctcagagtc acccaccgac aagaaaacca ccggcgtcga    1560
gggacccaag ggagacactg gcccccgagg cccaagggga cccgcaggcc cccctggccg    1620
agatggcatc cctggacagc ctggacttcc cggacccccc ggaccccccg gacctcccgg    1680
accccctggc ctcggaggaa actttgctcc ccagctgtct tatggctatg atgagaaatc    1740
aaccggagga atttccgtgc ctggcccat gggtccctct ggtcctcgtg gtctccctgg    1800 ccccctggt gcacctggtc cccaaggctt ccaaggtccc cctggtgagc tggcgagcc      1860 tggagcttca ggtcccatgg gtccccgagg tcccccaggt ccccctggaa agaatggaga    1920
tgatggggaa gctggaaaac ctggtcgtcc tggtgagcgt gggcctcctg gcctcaggg     1980 tgctcgagga ttgcccggaa cagctggcct ccctggaatg aagggacaca gaggtttcag    2040
tggtttggat ggtgccaagg gagatgctgg tcctgctggt cctaagggtg agcctggcag    2100
ccctggtgaa aatggagctc ctggtcagat gggcccccgt ggcctgcctg gtgagagagg    2160
tcgccctgga gcccctggcc ctgctggtgc tcgtggaaat gatggtgcta ctggtgctgc    2220 cgggcccct ggtcccaccg gcccgctgg tcctcctggc ttcctggtg ctgttggtgc       2280 taagggtgaa gctggtcccc aagggccccg aggctctgaa ggtccccagg gtgtgcgtgg    2340
tgagcctggc cccctggcc ctgctggtgc tgctggccct gctggaaacc ctggtgctga    2400
tggacagcct ggtgctaaag gtgccaatgg tgctcctggt attgctggtg ctcctggctt    2460
ccctggtgcc cgaggcccct ctggaccca gggcccccgc ggccctcctg gtcccaaggg    2520
taacagcggt gaacctggtg ctcctggcag caaaggagac actggtgcta agggagagcc    2580 tggcctgtt ggtgttcaag accccctgg ccctgctgga gaggaaggaa agcgaggagc     2640
tcgaggtgaa cccggaccca ctggcctgcc cggacccct ggcgagcgtg gtggacctgg    2700
tagccgtggt ttccctggcg cagatggtgt tgctggtccc aagggtcccg ctggtgaacg    2760
tggttctcct ggccccgctg gccccaaagg atctcctggt gaagctggtc gtcccggtga    2820
agctggtctg cctggtgcca agggtctgac tggaagccct ggcagccctg gtcctgatgg    2880
caaaactggc cccctggtc cgccggtca agatggtcgc cccggacccc caggcccacc     2940
tggtgcccgt ggtcaggctg gtgtgatggg attccctgga cctaaggtg ctgctggaga    3000 gcccggcaag gctggagagc gaggtgttcc cggaccccct ggcgctgtcg gtcctgctgg    3060
caaagatgga gaggctggag ctcagggacc ccctggccct gctggtcccg ctggcgagag    3120
aggtgaacaa ggccctgctg gctccccgg attccagggt ctccctggtc ctgctggtcc    3180
tccaggtgaa gcaggcaaac ctggtgaaca gggtgttcct ggagaccttg cgcccctgg    3240 ccctctgga gcaagaggcg agagaggttt cctggcgag cgtggtgtgc aaggtccccc    3300
tggtcctgct ggaccccgag gggccaacgg tgctcccggc aacgatggtg ctaagggtga    3360
tgctggtgcc cctggagctc ccggtagcca gggcgccct ggccttcagg gaatgcctgg    3420
tgaacgtggt gcagctggtc ttccaggcc taagggtgac agaggtgatg ctggtcccaa    3480
aggtgctgat ggctctcctg gcaaagatgg cgtccgtggt ctgaccggcc ccattggtcc    3540
tcctggccct gctggtgccc ctggtgacaa gggtgaaagt ggtccagcg gcctgctgg     3600 tcccactgga gctcgtggtg cccccggaga ccgtggtgag cctggtcccc ccggccctgc    3660
```

-continued

```
tggctttgct ggcccccctg gtgctgacgg ccaacctggt gctaaaggcg aacctggtga    3720
tgctggtgcc aaaggcgatg ctggtccccc tgggcctgcc ggacccgctg accccctgg     3780 ccccattggt aatgttggtg ctcctggagc caaaggtgct cgcggcagcg ctggtccccc    3840
tggtgctact ggtttccctg gtgctgctgg ccgagtcggt cctcctggcc cctctggaaa    3900
tgctggaccc cctggccctc ctggtcctgc tggcaaagaa ggcggcaaag gtccccgtgg    3960
tgagactggc cctgctggac gtcctggtga agttggtccc cctggtcccc ctggccctgc    4020
tggcgagaaa ggatcccctg gtgctgatgg tcctgctggt gctcctggta ctcccgggcc    4080
tcaaggtatt gctggacagc gtggtgtggt cggcctgcct ggtcagagag agagagagg     4140 cttccctggt cttcctggcc cctctggtga acctggcaaa caaggtccct ctggagcaag    4200
tggtgaacgt ggtccccccg gtcccatggg ccccccctgga ttggctggac cccctggtga   4260
atctggacgt gagggggctc ctgctgccga aggttcccct ggacgagacg gttctcctgg    4320
cgccaagggt gaccgtggtg agaccggccc cgctggaccc cctggtgctc ctggtgctcc    4380
tggtgcccct ggccccgttg ccctgctgg caagagtggt gatcgtggtg agactggtcc     4440
tgctggtccc gccggtcccg tcggccccgt cggcgcccgt ggccccgccg accccaagg     4500 ccccccgtggt gacaagggtg agacaggcga acagggcgac agaggcataa agggtcaccg   4560
tggcttctct ggcctccagg gtccccctgg ccctcctggc tctcctggtg aacaaggtcc    4620
ctctggagcc tctggtcctg ctggtccccg aggtcccccct ggctctgctg gtgctcctgg   4680
caaagatgga ctcaacggtc tccctggccc cattgggccc cctggtcctc gcggtcgcac    4740
tggtgatgct ggtcctgttg gtcccccgg ccctcctgga cctcctggtc ccctggtcc      4800 tcccagcgct ggtttcgact tcagcttcct gccccagcca cctcaagaga aggctcacga    4860
tggtggccgc tactaccggg ctgatgatgc caatgtggtt cgtgaccgtg acctcgaggt    4920
ggacaccacc ctcaagagcc tgagccagca gatcgagaac atccggagcc cagagggaag    4980
ccgcaagaac cccgcccgca cctgccgtga cctcaagatg tgccactctg actgaagag     5040 tggagagtac tggattgacc ccaaccaagg ctgcaacctg gatgccatca agtcttctg     5100 caacatggag actggtgaga cctgcgtgta ccccactcag cccagtgtgg cccagaagaa    5160
ctggtacatc agcaagaacc caaggacaa gaggcatgtc tggttcggcg agagcatgac     5220
cgatggattc cagttcgagt atggcggcca gggctccgac cctgccgatg tggccatcca    5280
gctgaccttc ctgcgcctga tgtccaccga ggcctcccag aacatcacct accactgcaa    5340
gaacagcgtg gcctacatgg accagcagac tggcaacctc aagaaggccc tgctcctcaa    5400
gggctccaac gagatcgaga tccgcgccga gggcaacagc cgcttcacct acagcgtcac    5460
tgtcgatggc tgcacgagtc acaccggagc tggggcaag acagtgattg aatacaaaac     5520
caccaagtcc tcccgcctgc ccatcatcga tgtggccccc ttgacgttg gtgccccaga    5580 ccaggaattc ggcttcgacg ttggccctgt ctgcttcctg tagaagcttg gtaccgaatt    5640
ccctgtgacc cctccccagt gcctctcctg gccctggaag ttgccactcc agtgcccacc   5700
agccttgtcc taataaaatt aagttgcatc attttgtctg actaggtgtc cttctataat   5760
attatggggt ggaggggggt ggtatggagc aaggggcaag ttgggaagac aacctgtagg    5820
gcctgcgggg tctattggga accaagctgg agtgcagtgg cacaatcttg gctcactgca   5880
atctccgcct cctgggttca agcgattctc ctgcctcagc ctcccgagtt gttgggattc   5940
caggcatgca tgaccaggct cagctaaattt ttgttttttt ggtagagacg gggtttcacc   6000
atattggcca ggctggtctc caactcctaa tctcaggtga tctacccacc ttggcctccc   6060
```

```
aaattgctgg gattacaggc gtgaaccact gctcccttcc ctgtccttac gcgtagaatt   6120
ggtaaagaga gtcgtgtaaa atatcgagtt cgcacatctt gttgtctgat tattgatttt   6180
tggcgaaacc atttgatcat atgacaagat gtgtatctac cttaacttaa tgattttgat   6240
aaaaatcatt aactagtcca tggctgcctc gcgcgtttcg gtgatgacgg tgaaaacctc   6300
tgacacatgc agctcccgga gacggtcaca gcttgtctgt aagcggatgc cgggagcaga   6360
caagcccgtc agggcgcgtc agcgggtgtt ggcgggtgtc ggggcgcagc catgacccag   6420
tcacgtagcg atagcggagt gtatactggc ttaactatgc ggcatcagag cagattgtac   6480
tgagagtgca ccatatgcgg tgtgaaatac cgcacagatg cgtaaggaga aaataccgca   6540
tcaggcgctc ttccgcttcc tcgctcactg actcgctgcg ctcggtcgtt cggctgcggc   6600
gagcggtatc agctcactca aaggcggtaa tacggttatc cacagaatca ggggataacg   6660
caggaaagaa catgtgagca aaaggccagc aaaaggccag gaaccgtaaa aaggccgcgt   6720
tgctggcgtt tttccatagg ctccgccccc ctgacgagca tcacaaaaat cgacgctcaa   6780
gtcagaggtg gcgaaacccg acaggactat aaagatacca ggcgtttccc cctggaagct   6840
ccctcgtgcg ctctcctgtt ccgaccctgc cgcttaccgg atacctgtcc gcctttctcc   6900
cttcgggaag cgtggcgctt tctcatagct cacgctgtag gtatctcagt tcggtgtagg   6960
tcgttcgctc caagctgggc tgtgtgcacg aaccccccgt tcagcccgac cgctgcgcct   7020
tatccggtaa ctatcgtctt gagtccaacc cggtaagaca cgacttatcg ccactggcag   7080
cagccactgg taacaggatt agcagagcga ggtatgtagg cggtgctaca gagttcttga   7140
agtggtggcc taactacggc tacactagaa gaacagtatt tggtatctgc gctctgctga   7200
agccagttac cttcggaaaa agagttggta gctcttgatc cggcaaacaa accaccgctg   7260
gtagcggtgg ttttttgtt tgcaagcagc agattacgcg cagaaaaaa ggatctcaag   7320 aagatccttt gatcttttct acggggtctg acgctcagtg gaacgaaaac tcacgttaag   7380
ggattttggt catgagatta tcaaaaagga tcttcaccta gatcctttta aattaaaaat   7440
gaagttttaa atcaatctaa agtatatatg agtaaacttg gtctgacagt taccaatgct   7500
taatcagtga ggcacctatc tcagcgatct gtctatttcg ttcatccata gttgcctgac   7560
tcc                                                                 7563
```

<210> SEQ ID NO 4
<211> LENGTH: 7269
<212> TYPE: DNA
<213> ORGANISM: Homo Sapiens

<400> SEQUENCE: 4

```
cgtgaggctc cggtgcccgt cagtgggcag agcgcacatc gcccacagtc cccgagaagt    60
tggggggagg ggtcggcaat tgaaccggtg cctagagaaa gtggcgcggg gtaaactggg   120
aaagtgatgt cgtgtactgg ctccgccttt ttcccgaggg tggggagaa ccgtatataa    180 gtgcagtagt cgccgtgaac gttctttttc gcaacgggtt tgccgccaga acacaggtaa   240
gtgccgtgtg tggttcccgc gggcctggcc tctttacggg ttatggccct tgcgtgcctt   300
gaattacttc cacgccctg gctgcagtac gtgattcttg atcccgagct cgggttgga    360 agtgggtggg agagttcgag gccttgcgct taaggagccc cttcgcctcg tgcttgagtt   420
gaggcctggc ttgggcgctg gggccgccgc gtgcgaatct ggtggcacct tcgcgcctgt   480
ctcgctgctt tcgataagtc tctagccatt taaaattttt gatgacctgc tgcgacgctt   540
```

```
tttttctggc aagatagtct tgtaaatgcg ggccaagatc tgcacactgg tatttcggtt      600 tttgggccg cggcggcga cggggcccgt gcgtcccagc gcacatgttc ggcgaggcgg       660
ggcctgcgag cgcggccacc gagaatcgga cgggggtagt ctcaagctgg ccggcctgct    720
ctggtgcctg gccctcgcgcc gccgtgtatc gccccgccct gggcggcaag gctggccgg     780 tcggcaccag ttgcgtgagc ggaaagatgg ccgcttcccg gccctgctgc agggagctca    840
aaatggagga cgcggcgctc gggagagcgg gcgggtgagt cacccacaca aaggaaaagg   900
gcctttccgt cctcagccgt cgcttcatgt gactccacgg agtaccgggc gccgtccagg    960
cacctcgatt agttctcgag cttttggagt acgtcgtctt taggttgggg ggaggggttt      1020
tatgcgatgg agtttcccca cactgagtgg gtggagactg aagttaggcc agcttggcac    1080
ttgatgtaat tctccttgga atttgcccctt tttgagtttg gatcttggtt cattctcaag      1140
cctcagacag tggttcaaag tttttttctt ccatttcagg tgtcgtgaaa actaccccta      1200
aaagccagct agcgtctaag tgctagacat gctcagcttt gtggatacgc ggactttgtt     1260
gctgcttgca gtaaccttat gcctagcaac atgccaatct ttacaagagg aaactgtaag    1320
aaagggccca gccggagata gaggaccacg tggagaaagg ggtccaccag gccccccagg  1380
cagagatggt gaagatggtc ccacaggccc tcctggtcca cctggtcctc ctggcccccc     1440
tggtctcggt gggaactttg ctgctcagta tgatggaaaa ggagttggac ttggccctgg   1500
accaatgggc ttaatgggac ctagaggccc acctggtgca gctggagccc caggccctca   1560
aggtttccaa ggacctgctg gtgagcctgg tgaacctggt caaactggtc ctgcaggtgc    1620
tcgtggtcca gctggccctc ctggcaaggc tggtgaagat ggtcaccctg aaaacccgg    1680 acgacctggt gagagaggag ttgttggacc acagggtgct cgtggtttcc ctggaactcc      1740
tggacttcct ggcttcaaag gcattagggg acacaatggt ctggatggat gaagggaca   1800 gcccggtgct cctggtgtga agggtgaacc tggtgcccct ggtgaaaatg gaactccagg  1860
tcaaacagga gcccgtgggc ttcctggtga gagaggacg gttggtgccc ctggcccagc   1920
tggtgcccgt ggcagtgatg gaagtgtggg tccgtgggt cctgctggtc ccattgggtc      1980 tgctggcccct ccaggcttcc caggtgcccc tggccccaag ggtgaaattg gagctgttgg   2040
taacgctggt cctgctggtc ccgccggtcc ccgtggtgaa gtgggtcttc caggcctctc    2100 cggcccccgtt ggacctcctg gtaatcctgg agcaaacggc cttactgtg ccaagggtgc    2160 tgctggcctt cccggcgttg ctggggctcc cggcctccct ggaccccgcg gtattcctgg   2220
ccctgttggt gctgccggtg ctactggtgc cagaggactt gttggtgagc ctggtccagc    2280
tggctccaaa ggagagagcg gtaacaaggg tgagcccggc tctgctgggc cccaaggtcc   2340
tcctggtccc agtggtgaag aaggaaagag aggccctaat ggggaagctg gatctgccgg   2400
ccctccagga cctcctgggc tgagaggtag tcctggttct cgtggtcttc ctggagctga    2460 tgcagagct ggcgtcatgg gccctcctgg tagtcgtggt gcaagtgcc ctgctggagt       2520 ccgaggacct aatggagatg ctggtcgccc tgggagcct ggtctcatgg gacccagagg    2580
tcttcctggt tcccctggaa atatcggccc cgctggaaaa gaaggtcctg tcggcctccc     2640
tggcatcgac ggcaggcctg gcccaattgg ccccgctgga gcaagaggag agcctggcaa  2700
cattggattc cctggaccca aaggccccac tggtgatcct ggcaaaaacg gtgataaagg   2760
tcatgctggt cttgctggtg ctcggggtgc tccaggtcct gatggaaaca atggtgctca  2820
gggacctcct ggaccacagg gtgttcaagg tggaaaaggt gaacagggtc ccgctggtcc   2880
tccaggcttc cagggtctgc ctggcccctc aggtcccgct ggtgaagttg gcaaaccagg   2940
```

```
agaaagggt ctccatggtg agtttggtct ccctggtcct gctggtccaa gaggggaacg    3000
cggtccccca ggtgagagtg gtgctgccgg tcctactggt cctattggaa gccgaggtcc    3060
ttctggaccc ccagggcctg atggaaacaa gggtgaacct ggtgtggttg tgctgtggg     3120
cactgctggt ccatctggtc ctagtggact cccaggagag aggggtgctg ctggcatacc    3180
tggaggcaag ggagaaaagg gtgaacctgg tctcagaggt gaaattggta accctggcag    3240
agatggtgct cgtggtgctc ctggtgctgt aggtgcccct ggtcctgctg gagccacagg    3300
tgaccggggc gaagctgggg ctgctggtcc tgctggtcct gctggtcctc ggggaagccc    3360
tggtgaacgt ggtgaggtcg gtcctgctgg ccccaatgga tttgctggtc ctgctggtgc    3420
tgctggtcaa cctggtgcta aaggagaaag aggagccaaa gggcctaagg gtgaaaacgg    3480
tgttgttggt cccacaggcc ccgttggagc tgctggccca gctggtccaa atggtccccc    3540
cggtcctgct ggaagtcgtg gtgatggagg ccccctggt atgactggtt ccctggtgc      3600
tgctggacgg actggtcccc caggaccctc tggtatttct ggccctcctg gtccccctgg    3660
tcctgctggg aaagaagggc ttcgtggtcc tcgtggtgac caaggtccag ttggccgaac    3720
tggagaagta ggtgcagttg gtcccccgg cttcgctggt gagaagggtc cctctggaga     3780
ggctggtact gctggacctc ctggcactcc aggtcctcag ggtcttcttg gtgctcctgg    3840
tattctgggt ctccctggct cgagaggtga acgtggtcta ccaggtgttg ctggtgctgt    3900
gggtgaacct ggtcctcttg gcattgccgg ccctcctggg gcccgtggtc ctcctggtgc    3960
tgtgggtagt cctggagtca acggtgctcc tggtgaagct ggtcgtgatg gcaaccctgg    4020
gaacgatggt ccccaggtc gcgatggtca acccggacac aagggagagc gcggttaccc     4080
tggcaatatt ggtccgttg gtgctgcagg tgcacctggt cctcatgcc ccgtgggtcc      4140
tgctggcaaa catggaaacc gtggtgaaac tggtcctttct ggtcctgttg gtcctgctgg   4200
tgctgttggc ccaagaggtc ctagtgggcc acaaggcatt cgtggcgata agggagagcc    4260
cggtgaaaag gggcccagag gtcttcctgg cttaaaggga cacaatggat tgcaaggtct    4320
gcctggtatc gctggtcacc atggtgatca aggtgctcct ggctccgtgg gtcctgctgg    4380
tcctagggg cctgctggtc cttctggccc tgctggaaaa gatggtcgca ctggacatcc     4440
tggtacagtt ggacctgctg gcattcgagg ccctcagggt caccaaggcc ctgctggccc    4500
ccctggtccc cctggccctc ctggacctcc aggtgtaagc ggtggtggtt atgactttgg    4560
ttacgatgga gacttctaca gggctgacca gcctcgctca gcaccttctc tcagacccaa    4620
ggactatgaa gttgatgcta ctctgaagtc tctcaacaac cagattgaga cccttcttac    4680
tcctgaaggc tctagaaaga acccagctcg cacatgccgt gacttgagac tcagccaccc    4740
agagtggagc agtggttact actggattga ccctaaccaa ggatgcacta tggatgctat    4800
caaagtatac tgtgatttct ctactggcga acctgtatc cgggcccaac ctgaaaacat     4860
cccagccaag aactggtata ggagctccaa ggacaagaaa cacgtctggc taggagaaac    4920
tatcaatgct ggcagccagt ttgaatataa tgtagaagga gtgacttcca aggaaatggc    4980
tacccaactt gccttcatgc gcctgctggc caactatgcc tctcagaaca tcacctacca    5040
ctgcaagaac agcattgcat acatggatga ggagactgga aacctgaaaa aggctgtcat    5100
tctacagggc tctaatgatg ttgaacttgt tgctgagggc aacagcaggt tcacttacac    5160
tgttcttgta gatggctgct ctaaaaagac aaatgaatgg ggaaagacaa tcattgaata    5220
caaaacaaat aagccatcac gcctgcccct ccttgatatt gcacctttgg acatcggtgg    5280
```

```
tgctgaccag gaattctttg tggacattgg cccagtctgt ttcaaataaa agcttggtac    5340
cgaattccct gtgacccctc cccagtgcct ctcctggccc tggaagttgc cactccagtg    5400
cccaccagcc ttgtcctaat aaaattaagt tgcatcattt tgtctgacta ggtgtccttc    5460
tataatatta tggggtggag gggggtggta tggagcaagg ggcaagttgg gaagacaacc    5520
tgtagggcct gcggggtcta ttgggaacca agctggagtg cagtggcaca atcttggctc    5580
actgcaatct ccgcctcctg ggttcaagcg attctcctgc ctcagcctcc cgagttgttg    5640
ggattccagg catgcatgac caggctcagc taattttttgt tttttttggta gagacggggt    5700
ttcaccatat tggccaggct ggtctccaac tcctaatctc aggtgatcta cccaccttgg    5760
cctcccaaat tgctgggatt acaggcgtga accactgctc ccttccctgt ccttacgcgt    5820
agaattggta agagagtcg tgtaaaatat cgagttcgca catcttgttg tctgattatt    5880
gattttttggc gaaaccattt gatcatatga caagatgtgt atctacctta acttaatgat    5940
tttgataaaa atcattaact agtccatggc tgcctcgcgc gtttcggtga tgacggtgaa    6000
aacctctgac acatgcagct cccggagacg gtcacagctt gtctgtaagc ggatgccggg    6060
agcagacaag cccgtcaggg cgcgtcagcg ggtgttggcg ggtgtcgggg cgcagccatg    6120
acccagtcac gtagcgatag cggagtgtat actggcttaa ctatgcggca tcagagcaga    6180
ttgtactgag agtgcaccat atgcggtgtg aaataccgca cagatgcgta aggagaaaat    6240
accgcatcag cgctcttcc gcttcctcgc tcactgactc gctgcgctcg tcgttcggc     6300
tgcggcgagc ggtatcagct cactcaaagg cggtaatacg ttatccaca gaatcagggg    6360
ataacgcagg aaagaacatg tgagcaaaag gccagcaaaa ggccaggaac cgtaaaaagg    6420
ccgcgttgct ggcgtttttc cataggctcc gcccccctga cgagcatcac aaaaatcgac    6480
gctcaagtca gaggtggcga aacccgacag gactataaag ataccaggcg tttccccctg    6540
gaagctccct cgtgcgctct cctgttccga ccctgccgct taccggatac ctgtccgcct    6600
ttctcccttc gggaagcgtg gcgctttctc atagctcacg ctgtaggtat ctcagttcgg    6660
tgtaggtcgt tcgctccaag ctgggctgtg tgcacgaacc cccgttcag cccgaccgct    6720
gcgccttatc cggtaactat cgtcttgagt ccaacccgt aagacacgac ttatcgccac    6780
tggcagcagc cactggtaac aggattagca gagcgaggta tgtaggcggt gctacagagt    6840
tcttgaagtg gtggcctaac tacgctaca ctagaagaac agtatttggt atctgcgctc    6900
tgctgaagcc agttaccttc ggaaaaagag ttggtagctc ttgatccggc aaacaaacca    6960
ccgctggtag cggtggtttt tttgtttgca agcagcagat tacgcgcaga aaaaaggat    7020
ctcaagaaga tcctttgatc ttttctacgg ggtctgacgc tcagtggaac gaaaactcac    7080
gttaagggat tttggtcatg agattatcaa aaaggatctt cacctagatc cttttaaatt    7140
aaaaatgaag ttttaaatca atctaaagta tatatgagta aacttggtct gacagttacc    7200
aatgcttaat cagtgaggca cctatctcag cgatctgtct atttcgttca tccatagttg    7260
cctgactcc                                                           7269
```

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide BMP2_F

<400> SEQUENCE: 5
acagctagcc tcctaaaggt ccaccatggt                                      30

<210> SEQ ID NO 6
<211> LENGTH: 29
<212> TYPE: DNA
<213> ORGANISM: Artificial Sequence
<220> FEATURE:
<223> OTHER INFORMATION: Oligonucleotide BMP2_R

<400> SEQUENCE: 6
tataagcttc tagcgacacc cacaaccct                              29

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide BMP2_SF

<400> SEQUENCE: 7
atgcaagcag gtgggaaagt                                        20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide BMP2_SR

<400> SEQUENCE: 8
gggagccaca atccagtcat                                        20

<210> SEQ ID NO 9
<211> LENGTH: 28
<212> TYPE: DNA
<213> ORGANISM: Artificial Sequence
<220> FEATURE:
<223> OTHER INFORMATION: Oligonucleotide BMP7_F

<400> SEQUENCE: 9
tcagctagcg tagagccggc gcgatgca                               28

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide BMP7_R

<400> SEQUENCE: 10
tataagcttc tagtggcagc cacaggc                                27

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide BMP7_SF

<400> SEQUENCE: 11
gctggctggt gtttgacatc                                        20

<210> SEQ ID NO 12
<211> LENGTH: 20
<212> TYPE: DNA
<213> ORGANISM: Artificial Sequence
<220> FEATURE:

<223> OTHER INFORMATION: Oligonucleotide BMP7_SR

<400> SEQUENCE: 12
tggtggcgtt catgtaggag                                          20

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide COL1A1_F

<400> SEQUENCE: 13
ccagctagcg tctagggtct agacatgttc                               30

<210> SEQ ID NO 14
<211> LENGTH: 33
<212> TYPE: DNA
<213> ORGANISM: Artificial Sequence
<220> FEATURE:
<223> OTHER INFORMATION: Oligonucleotide COL1A1_R

<400> SEQUENCE: 14
tataagcttc tacaggaagc agacagggcc aac                           33

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide COL1A1_SF

<400> SEQUENCE: 15
tgacgagacc aagaactgcc                                          20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide COL1A1_SR

<400> SEQUENCE: 16
gcaccatcat ttccacgagc                                          20

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide COL1A2_F

<400> SEQUENCE: 17
ccagctagcg tctaagtgct agacatgctc                               30

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide COL1A2_R

<400> SEQUENCE: 18
cgaagctttt atttgaaaca gactgggcca                               30

```
<210> SEQ ID NO 19
<211> LENGTH: 20
<212> TYPE: DNA
<213> ORGANISM: Artificial Sequence
<220> FEATURE:
<223> OTHER INFORMATION: Oligonucleotide COL1A2_SF

<400> SEQUENCE: 19
ctggtgaagc tggtcgtgat                                          20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide COL1A2_SR

<400> SEQUENCE: 20
cggatacagg tttcgccagt                                          20
```